(12) United States Patent
Bitting et al.

(10) Patent No.: US 12,326,865 B2
(45) Date of Patent: *Jun. 10, 2025

(54) CHEMICAL RECYCLING OF PLASTIC-DERIVED STREAMS TO A CRACKER SEPARATION ZONE

(71) Applicant: Eastman Chemical Company, Kingsport, TN (US)

(72) Inventors: Daryl Bitting, Longview, TX (US); David Eugene Slivensky, Tatum, TX (US); Xianchun Wu, Longview, TX (US); Michael Paul Ekart, Kingsport, TN (US); Bruce Roger DeBruin, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/760,371

(22) PCT Filed: Feb. 10, 2021

(86) PCT No.: PCT/US2021/017352
§ 371 (c)(1),
(2) Date: Aug. 9, 2022

(87) PCT Pub. No.: WO2021/163113
PCT Pub. Date: Aug. 19, 2021

(65) Prior Publication Data
US 2023/0116183 A1 Apr. 13, 2023

Related U.S. Application Data

(60) Provisional application No. 62/972,291, filed on Feb. 10, 2020.

(51) Int. Cl.
*C07C 7/09* (2006.01)
*B01D 5/00* (2006.01)
(Continued)

(52) U.S. Cl.
CPC ..... *G06F 16/24558* (2019.01); *B01D 5/0036* (2013.01); *C07C 7/09* (2013.01);
(Continued)

(58) Field of Classification Search
None
See application file for complete search history.

(56) References Cited

U.S. PATENT DOCUMENTS 3,175,968 A 3/1965 Berger
3,544,291 A 12/1970 Schlinger et al.
(Continued)

FOREIGN PATENT DOCUMENTS

EP 467860 A1 7/1991
JP 2000176403 A 6/2000
(Continued)

OTHER PUBLICATIONS

Co-pending U.S. Appl. No. 17/755,320, filed Apr. 27, 2022; Bitting et al.
(Continued)

Primary Examiner — Tam M Nguyen
(74) Attorney, Agent, or Firm — Steven A. Owen

(57) ABSTRACT

Methods and systems are provided for the conversion of waste plastics into various useful downstream recycle-content products. More particularly, the present system and method involves integrating a pyrolysis facility with a cracker facility by introducing at least a stream of r-pyrolysis gas into the cracker facility. In the cracker facility, the
(Continued)

r-pyrolysis gas may be separated to form one or more recycle content products, and can enhance the operation of the facility.

9 Claims, 15 Drawing Sheets

(51) Int. Cl.
| | |
|---|---|
| *C10B 53/07* | (2006.01) |
| *C10G 1/00* | (2006.01) |
| *C10G 1/10* | (2006.01) |
| *G06F 16/2455* | (2019.01) |
| *G06F 16/25* | (2019.01) |

(52) U.S. Cl.
CPC .............. *C10B 53/07* (2013.01); *C10G 1/002* (2013.01); *C10G 1/10* (2013.01); *G06F 16/254* (2019.01); *C10G 2300/1003* (2013.01)

(56) References Cited

U.S. PATENT DOCUMENTS

| | | | |
|---|---|---|---|
| 4,364,905 | A | 12/1982 | Fahrig et al. |
| 5,253,479 | A | 10/1993 | Cintio et al. |
| 5,744,668 | A | 4/1998 | Zhou et al. |
| 6,184,427 | B1 | 2/2001 | Klepfer et al. |
| 7,261,807 | B2 | 8/2007 | Henry et al. |
| 2004/0182001 | A1 | 9/2004 | Masemore et al. |
| 2006/0287561 | A1* | 12/2006 | Choi ................ C10G 45/64 585/324 |
| 2008/0230444 | A1 | 9/2008 | Iwadate et al. |
| 2008/0277314 | A1 | 11/2008 | Halsey |
| 2012/0053383 | A1 | 3/2012 | Malaty et al. |
| 2012/0160741 | A1 | 6/2012 | Gong et al. |
| 2012/0266532 | A1 | 10/2012 | Bergmann et al. |
| 2014/0303339 | A1 | 10/2014 | Keusenkothen et al. |
| 2016/0264874 | A1 | 9/2016 | Narayanaswamy et al. |
| 2016/0264885 | A1 | 9/2016 | Narayanaswamy et al. |
| 2017/0283714 | A1 | 10/2017 | Combs |
| 2019/0055483 | A1 | 2/2019 | Bafna et al. |
| 2019/0161683 | A1 | 5/2019 | Narayanaswamy et al. |
| 2019/0177626 | A1 | 6/2019 | Ramamurthy et al. |
| 2019/0270939 | A1 | 9/2019 | Javeed et al. |
| 2019/0275486 | A1 | 9/2019 | Peltekis et al. |
| 2020/0017772 | A1 | 1/2020 | Ramamurthy et al. |
| 2020/0024524 | A1 | 1/2020 | Barrai et al. |
| 2022/0127209 | A1 | 4/2022 | Ward et al. |
| 2022/0380685 | A1 | 12/2022 | Wu et al. |
| 2022/0403259 | A1 | 12/2022 | Bitting et al. |
| 2022/0403260 | A1 | 12/2022 | Bitting et al. |
| 2023/0072869 | A1* | 3/2023 | Bitting ................ C10K 3/008 |
| 2023/0081980 | A1* | 3/2023 | Bitting ................ C10G 1/10 252/373 |
| 2023/0116183 | A1* | 4/2023 | Bitting ................ C07C 7/09 585/241 |
| 2023/0117658 | A1 | 4/2023 | Bitting et al. |
| 2023/0211394 | A1* | 7/2023 | DeBruin ............. C10G 3/40 521/41 |

FOREIGN PATENT DOCUMENTS

| | | |
|---|---|---|
| WO | WO 2005/021686 A1 | 3/2005 |
| WO | WO 2010/051013 A1 | 5/2010 |
| WO | WO 2012/061005 A2 | 5/2012 |
| WO | WO 2018/069794 A1 | 4/2018 |
| WO | WO 2018/127813 A1 | 7/2018 |
| WO | WO 2019/019539 A | 1/2019 |
| WO | WO 2021/087066 A1 | 5/2021 |
| WO | WO 2021/163113 A1 | 8/2021 |

OTHER PUBLICATIONS

Co-pending U.S. Appl. No. 17/755,321, filed Apr. 27, 2022; Bitting et al.
Co-pending U.S. Appl. No. 17/755,346, filed Apr. 27, 2022; Wu et al.
Co-pending U.S. Appl. No. 17/760,374, filed Aug. 9, 2022; Bitting et al.
Co-pending U.S. Appl. No. 17/760,372, filed Aug. 9, 2022; Bitting et al.
Co-pending U.S. Appl. No. 17/760,375, filed Aug. 9, 2022; Bitting et al.
Notification of Transmittal of the International Search Report and the Written Opinion of the International Searching Authority with Date of Mailing Feb. 19, 2021 for International Application No. PCT/US2020/057828.
Notification of Transmittal of the International Search Report and the Written Opinion of the International Searching Authority with Date of Mailing Feb. 19, 2021 for International Application No. PCT/US2020/057832.
Notification of Transmittal of the International Search Report and the Written Opinion of the International Searching Authority with Date of Mailing Feb. 18, 2021 for International Application No. PCT/US2020/057851.
Notification of Transmittal of the International Search Report and the Written Opinion of the International Searching Authority with Date of Mailing Jun. 7, 2021 for International Application No. PCT/US2021/017345.
Notification of Transmittal of the International Search Report and the Written Opinion of the International Searching Authority with Date of Mailing Jun. 2, 2021 for International Application No. PCT/US2021/017348.
Notification of Transmittal of the International Search Report and the Written Opinion of the International Searching Authority with Date of Mailing Jun. 4, 2021 for International Application No. PCT/US2021/017352.
Notification of Transmittal of the International Search Report and the Written Opinion of the International Searching Authority with Date of Mailing Jun. 4, 2021 for International Application No. PCT/US2021/017350.
ASTM D5399; "Standard Test Method for Boiling Point Distribution of Hydrocarbon Solvents by Gas Chromatography"; Published Dec. 2017.
ASTM D2887; "Standard Test Method for Boiling Range Distribution of Petroleum Fractions by Gas Chromatrography"; Published Jan. 2020.
European Search Report dated Nov. 22, 2023 received in Application No. 20882101.7.
USPTO Office Action dated Jun. 4, 2024 received in Co-pending U.S. Appl. No. 17/755,345.
USPTO Office Action dated Feb. 2, 2024 received in Co-pending U.S. Appl. No. 17/760,372.
Notice of Allowance dated Aug. 14, 2024 received in co-pending U.S. Appl. No. 17/760,372.
Co-pending U.S. Appl. No. 18/692,904, filed Mar. 18, 2024; Anderson et al.
European Search Report dated Feb. 9, 2024 received in Application No. 21753039.3.
European Search Report dated Feb. 19, 2024 received in Application No. 21754678.7.
European Search Report dated Feb. 20, 2024 received in Application No. 21753382.7.
Notification of Transmittal of the International Search Report and the Written Opinion of the International Searching Authority with Date of Mailing Jan. 2, 2023 for International Application No. PCT/US2022/043751.
USPTO Office Action dated Jan. 24, 2025 received in Co-pending U.S. Appl. No. 17/755,345.
Co-pending U.S. Appl. No. 18/889,556, filed Sep. 19, 2024; Bitting et al.
USPTO Office Action dated Jun. 7, 2024 received in Co-pending U.S. Appl. No. 17/760,375.
Notice of Allowance dated Mar. 6, 2025 received in C-pending U.S. Appl. No. 17/760,375.

* cited by examiner

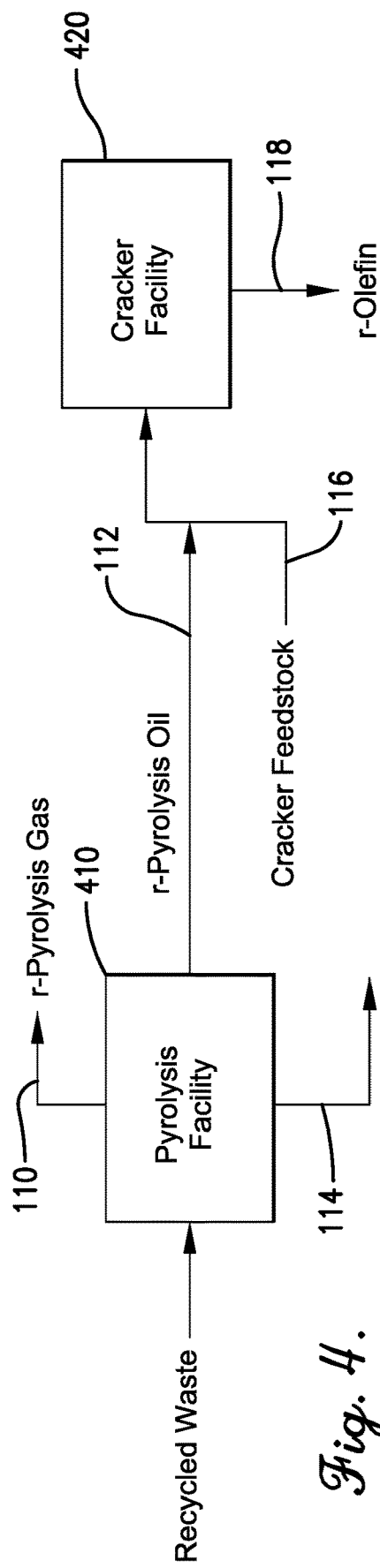
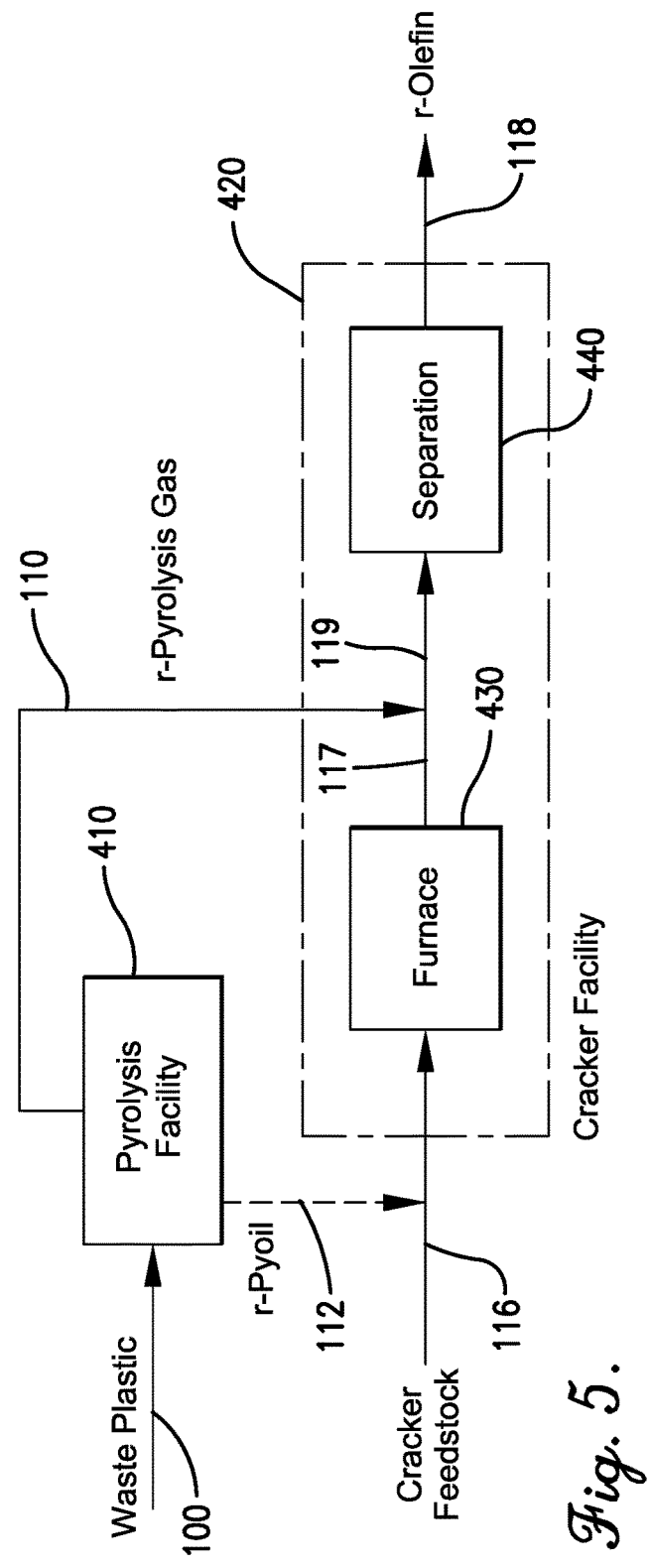

CHEMICAL RECYCLING OF PLASTIC-DERIVED STREAMS TO A CRACKER SEPARATION ZONE

CROSS-REFERENCE TO RELATED APPLICATION(S)

This application is a national stage filing under 35 USC § 371 of International Application Number PCT/US2021/017352, filed on, Feb. 10, 2021 which claims the benefit of the filing date to U.S. Provisional Application No. 62/972,291, filed on Feb. 10, 2020, the entire disclosures of which are incorporated by reference herein.

BACKGROUND

Waste materials, especially non-biodegradable waste materials, can negatively impact the environment when disposed of in landfills after a single use. Thus, from an environmental standpoint, it is desirable to recycle as much waste materials as possible. However, recycling waste materials can be challenging from an economic standpoint.

While some waste materials are relatively easy and inexpensive to recycle, other waste materials require significant and expensive processing in order to be reused. Further, different types of waste materials often require different types of recycling processes. In many cases, expensive physical sorting of waste materials into relatively pure, single-composition waste volumes is required.

To maximize recycling efficiency, it would be desirable for large-scale production facilities to be able to process feedstocks having recycle content originating from a variety of waste materials. Commercial facilities involved in the production of non-biodegradable products could benefit greatly from using recycle content feedstocks because the positive environmental impact of using recycle content feeds could offset the negative environmental impact of making non-biodegradable products.

SUMMARY

In one aspect, the present technology concerns a method for forming a recycled-content syngas that comprises: (a) introducing a pyrolysis feed into a pyrolysis unit, wherein the pyrolysis feed comprises at least one recycled waste plastic; (b) pyrolyzing at least a portion of the pyrolysis feed to thereby form a pyrolysis effluent comprising a pyrolysis gas; and (c) feeding at least a portion of the pyrolysis gas into a partial oxidation gasifier.

In one aspect, the present technology concerns a method for forming a recycled-content syngas that comprises: (a) pyrolyzing at least a portion of a pyrolysis feed comprising at least one recycled waste plastic in a pyrolysis unit to thereby form a pyrolysis effluent comprising a pyrolysis gas; (b) compressing at least a portion of the pyrolysis gas in a compression unit to thereby form a compressed pyrolysis gas; and (c) feeding at least a portion of the compressed pyrolysis gas into a partial oxidation gasifier.

In one aspect, the present technology concerns a method for forming a recycled-content syngas that comprises: (a) pyrolyzing at least a portion of a pyrolysis feed comprising at least one recycled waste plastic in a pyrolysis unit to thereby form a pyrolysis effluent comprising a pyrolysis gas; (b) removing at least a portion of halogens from the pyrolysis gas in a dehalogenation unit to thereby form a dehalogenated pyrolysis gas; and (c) feeding at least a portion of the dehalogenated pyrolysis gas into a partial oxidation gasifier.

In one aspect, the present technology concerns a method for forming a recycled-content syngas that comprises: (a) providing a pyrolysis feed comprising at least one recycled waste plastic; (b) removing at least a portion of halogens from the pyrolysis feed to thereby form a halogen waste stream and a dehalogenated feed; (c) pyrolyzing at least a portion of the dehalogenated feed in a pyrolysis unit to thereby form a pyrolysis effluent comprising a pyrolysis gas; and (d) feeding at least a portion of the pyrolysis gas into a partial oxidation gasifier.

In one aspect, the present technology concerns a method for forming a recycled-content syngas that comprises: (a) introducing a pyrolysis feed into a pyrolysis unit, wherein the pyrolysis feed comprises at least one recycled waste plastic; (b) pyrolyzing at least a portion of the pyrolysis feed to thereby form a pyrolysis effluent comprising a pyrolysis gas and a pyrolysis residue stream, wherein the pyrolysis residue stream comprises a carbon-containing solids content of at least 1 weight percent and/or a C20+ hydrocarbon content of at least 20 weight percent; and (c) feeding at least a portion of the pyrolysis residue stream into a partial oxidation gasifier.

In one aspect, the present technology concerns a method for forming a recycled-content syngas that comprises: (a) pyrolyzing a pyrolysis feed in a pyrolysis unit, wherein the pyrolysis feed comprises at least one recycled waste plastic; (b) removing a pyrolysis bottoms stream from a first position in the pyrolysis unit and a pyrolysis gaseous stream from a second position in the pyrolysis unit, wherein the first position is positioned lower than the second position; and (c) feeding at least a portion of the pyrolysis bottoms stream into a partial oxidation gasifier.

In one aspect, the present technology concerns a method for making an olefin product, the method comprising separating a feed stream comprising a recycle content pyrolysis gas (r-pyrolysis gas) in at least one fractionator downstream of a cracker furnace.

In one aspect, the present technology concerns a method for making an olefin product, the method comprising (a) introducing a column feed stream comprising alkanes and olefins into a dealkanizer column, wherein the column feed stream comprises a recycle content pyrolysis gas (r-pyrolysis gas); and (b) separating the column feed stream into an overhead stream enriched in a target alkane and a bottoms stream depleted in the target alkane, wherein at least one of the overhead stream and the bottom stream comprises at least 5 weight percent olefin, based on the total weight of the stream.

In one aspect, the present technology concerns a method for making an olefin product, the method comprising (a) introducing a column feed stream comprising alkanes and olefins into an olefin-alkane fractionator, wherein the column feed stream comprises a recycle content pyrolysis gas (r-pyrolysis gas); and (b) separating the column feed stream into an olefin-enriched overhead stream and an alkane-enriched bottoms stream in the olefin-alkane fractionator.

In one aspect, the present technology concerns a method of making an olefin product, the method comprising (a) pyrolyzing a feed stream comprising recycled waste material in a pyrolysis facility to provide a recycle content pyrolysis gas (r-pyrolysis gas) stream; and (b) separating a column feed stream in at least one fractionator of a fractionation section downstream of a cracker furnace in a cracking facility to provide an olefin product, wherein the column feed stream comprises at least a portion of the r-pyrolysis gas, wherein prior to at least a portion of the pyrolyzing of step (a), the cracker furnace was operated to form an olefin-containing effluent stream that was separated in the fractionation section of the cracker facility.

In one aspect, the present technology concerns a method of making an olefin product, the method comprising (a) pyrolyzing a feed stream comprising recycled waste material in a pyrolysis facility to provide a recycle content pyrolysis gas (r-pyrolysis gas) stream; (b) exchanging energy between at least a portion of the r-pyrolysis gas stream and one or more heat transfer streams in an energy exchange zone; and (c) introducing at least a portion of the r-pyrolysis gas from the energy exchange zone into a cracker facility.

In one aspect, the present technology concerns a recycle content pyrolysis gas (r-pyrolysis gas), wherein the r-pyrolysis gas comprises: at least 20 and/or not more than 75 weight percent of ethylene and/or propylene, at least 5 and/or not more than 50 weight percent of ethane and/or propane, at least 5 and/or not more than 60 weight percent of methane, an ethylene to ethane weight ratio or propylene to propane weight ratio of at least 1:1 and/or not more than 3:1, and at least one of the following properties (i) through (ix): (i) C4 hydrocarbons in an amount of not more than 20 weight percent; (ii) hydrogen in an amount of not more than 10 weight percent; (iii) C3+ diolefins in an amount of not more than 10 weight percent; (iv) C4+ olefins in an amount of not more than 10 weight percent; (v) C4 paraffins in an amount of not more than 5 weight percent; (vi) halogens in an amount of not more than 1 ppm; (v) carbonyls in an amount of not more than 100 ppm; (vi) carbon dioxide in an amount of not more than 100 ppm; (vii) carbon monoxide in an amount of not more than 2500 ppm; (viii) arsine and/or phosphine in an amount of not more than 15 ppb; and (ix) sulfur-containing compounds in an amount of not more than 100 ppm, wherein each of the above quantities are in amounts by weight, based on the total weight of the composition, and wherein the r-pyrolysis gas is formed by the pyrolysis of recycle waste plastic or materials derived therefrom.

In one aspect, the present technology concerns a process for separating an olefin-containing stream to form one or more product streams, wherein the process comprises introducing a stream comprising a recycle content pyrolysis gas (r-pyrolysis gas) into a cracker facility at a location downstream of an outlet of a cracker furnace.

In one aspect, the present technology concerns a process for separating an olefin-containing stream to form one or more product streams, wherein the process comprises (a) pyrolyzing a pyrolysis feed stream comprising recycled waste material to form a recycle content pyrolysis gas (r-pyrolysis gas); and (b) introducing at least a portion of the r-pyrolysis gas into a cracker facility in at least one location downstream of an outlet of a cracker furnace.

In one aspect, the present technology concerns a process for separating an olefin-containing stream to form one or more product streams, wherein the process comprises (a) introducing a column feed stream to in an olefin fractionator, wherein the column feed stream comprises a recycle content pyrolysis gas (r-pyrolysis gas); (b) separating the column feed stream in the olefin fractionator into an overhead stream enriched in a least one olefin and a bottoms stream depleted in at least one olefin, wherein at least one of the following conditions (i) through (vi) is met—(i) the mole ratio of the at least one olefin to its corresponding alkane in the column feed stream is at least 0.1% higher than if the column feed stream did not include the r-pyrolysis gas but had the same mass flow rate; (ii) the mass flow rate of a corresponding alkane of the at least one olefin in the overhead stream is at least 0.1% lower than if the column feed stream did not include the r-pyrolysis gas but had the same mass flow rate; (iii) the reflux ratio used during the separating is at least 0.1% lower than the reflux ratio used if the column feed stream did not include the r-pyrolysis gas but had the same mass flow rate; (iv) the pressure drop across the column is at least 0.1% lower than if the column feed stream did not include the r-pyrolysis gas but had the same mass flow rate; (v) the mass flow rate of liquid within the column is at least 0.1 wt % lower than if the column feed stream did not include the r-pyrolysis gas but had the same mass flow rate; and (vi) the energy input into the column is at least 0.1% lower than if the column feed stream did not include the r-pyrolysis gas but had the same mass flow rate.

BRIEF DESCRIPTION OF THE FIGURES

FIG. 4 depicts an exemplary system for processing waste plastic that includes a pyrolysis facility, a partial oxidation (PDX) gasification facility, and a cracker facility;

FIG. 5 depicts an exemplary system for processing waste plastic that includes a pyrolysis facility and a cracker facility, particularly illustrating embodiments of an integration strategy;

FIG. 11b depicts an exemplary system suitable for use in a quench zone as illustrated in FIG. 11a;

DETAILED DESCRIPTION

When a numerical sequence is indicated, it is to be understood that each number is modified the same as the first number or last number and is in an "or" relationship, i.e. each number is "at least," or "up to" or "not more than" as the case may be. For example, "at least 10 wt. %, 20, 30, 40, 50, 75 . . ." means the same as "at least 10 wt. %, or at least 20 wt. %, or at least 30 wt. %, or at least 40 wt. %, or at least 50 wt. %, or at least 75 wt. %, etc.

All concentrations or amounts are by weight unless otherwise stated.

As used herein, "PET" includes a homopolymer of polyethylene terephthalate, or polyethylene terephthalate modified with modifiers or containing residues or moieties of other than ethylene glycol and terephthalic acid, such as isophthalic acid, diethylene glycol, TMCD (2,2,4,4-tetramethyl-1,3-cyclobutanediol), CHDM (cyclohexanedimethanol), propylene glycol, isosorbide, 1,4-butanediol, 1,3-propane diol, and/or NPG (neopentyl glycol), or polyesters having repeating terephthalate units (and whether or not they contain repeating ethylene glycol based units) and one or more residues or moieties of TMCD (2,2,4,4-tetramethyl-1,3-cyclobutanediol), CHDM (cyclohexanedimethanol), propylene glycol, or NPG (neopentyl glycol), isosorbide, isophthalic acid, 1,4-butanediol, 1,3-propane diol, and/or diethylene glycol, or combinations thereof.

According to one embodiment or in combination with any of the mentioned embodiments, there is provided a chemical recycling facility that includes a pyrolysis facility and a cracker facility configured to produce at least one recycle content product. As used herein, "chemical recycling" refers to a waste plastic recycling process that includes a step of chemically converting waste plastic polymers into lower molecular weight polymers, oligomers, monomers, and/or non-polymeric molecules (e.g., hydrogen and carbon monoxide) that are useful by themselves and/or are useful as feedstocks to another chemical production process(es). Chemical recycling facilities as described herein may be used to convert mixed plastic waste to recycle content products or chemical intermediates used to form a variety of end use materials.

Chemical recycling facilities are not physical recycling facilities. As used herein, the term "physical recycling" (also known as mechanical recycling) refers to a recycling process that includes a step of melting waste plastic and forming the molten plastic into a new intermediate product (e.g., pellets or sheets) and/or a new end product (e.g., bottles). Generally, physical recycling does not change the chemical structure of the plastic being recycled. In one embodiment or in combination with any of the mentioned embodiments, the chemical recycling facilities described herein may be configured to receive and process waste streams from and/or that are not typically processable by a physical recycling facility.

Pyrolysis Facility

Figure 1:
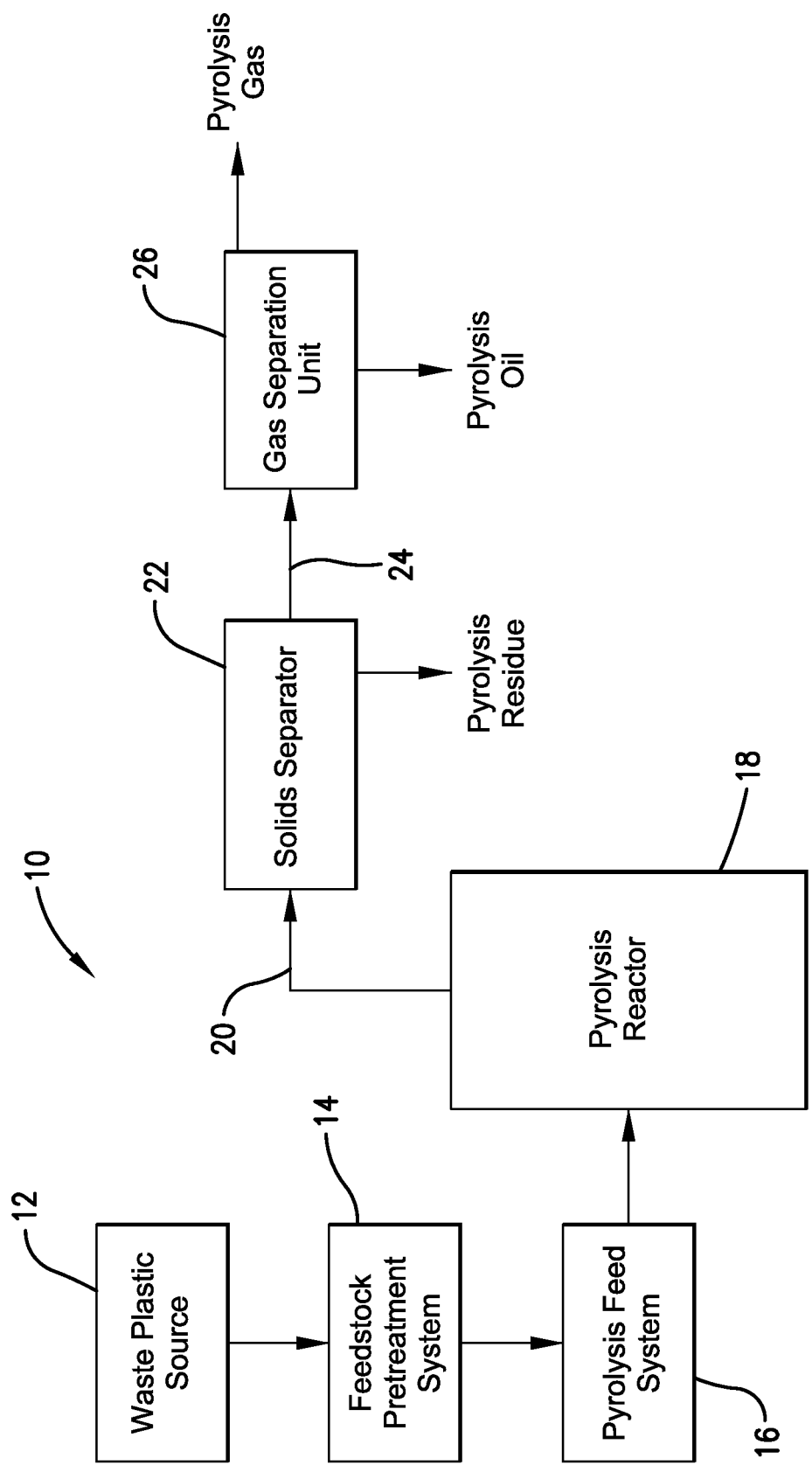
FIG. 1 depicts an exemplary pyrolysis facility that may at least partially convert one or more waste plastics into various pyrolysis-derived products.

FIG. 1 depicts an exemplary pyrolysis facility 10 that may be employed to at least partially convert one or more recycled wastes, particularly recycled waste plastics, into various useful pyrolysis-derived products, such as a pyrolysis residue, a pyrolysis oil, and a pyrolysis gas. As used herein, a "pyrolysis facility" refers to a facility that includes all equipment, lines, and controls necessary to carry out pyrolysis of a waste plastic. It should be understood that the pyrolysis facility shown in FIG. 1 is just one example of a system within which the present disclosure can be embodied. The present disclosure may find application in a wide variety of other systems where it is desirable to efficiently and effectively pyrolyze waste plastic into various desirable end products. The exemplary pyrolysis facility illustrated in FIG. 1 will now be described in greater detail.

As shown in FIG. 1, the pyrolysis facility 10 may include a waste plastic source 12 for supplying a mixed plastic waste ("MPW") and/or one or more waste plastics to the system 10. As used herein, a "mixed plastic waste," or MPW, refers to a post-industrial (or pre-consumer) plastic, a post-consumer plastic, or a mixture thereof. Examples of plastic materials include, but are not limited to, polyesters, one or more polyolefins (PO), and polyvinylchloride (PVC). Furthermore, as used herein, a "waste plastic" refers to any post-industrial (or pre-consumer) and post-consumer plastics, such as but not limited to polyesters, polyolefins (PO), and/or polyvinylchloride (PVC). In one embodiment or more embodiments, the waste plastic may also include a number of minor plastic components (other than PET and polyolefins) that total less than 50, not more than 40, not more than 30, not more than 20, not more than 15, or not more than 10 weight percent, and optionally can individually represent less than 30, not more than 20, not more than 15, not more than 10, or not more than 1 weight percent, of the waste plastic content.

In one embodiment or in combination with any of the mentioned embodiments, the MPW and/or waste plastics supplied by the plastic source 12 can be derived from or be supplied as a municipal solid waste stream ("MSW").

The plastic source 12 can comprise a hopper, storage bin, railcar, over-the-road trailer, or any other device that may hold or store waste plastics. In one embodiment or in combination with any of the mentioned embodiments, the plastic source 12 can comprise a municipal reclaimer facility, an industrial facility, a recycling facility, a commercial facility, a manufacturing facility, or combinations thereof.

In one embodiment or in combination with any of the mentioned embodiments, the MPW and/or waste plastics supplied by the plastic source 12 can be in the form of solid particles, such as chips, flakes, or a powder. The MPW supplied by the plastic source 12 may comprise MPW particulates. As used herein, "MPW particulates" refers to an MPW having an average particle diameter of less than one inch. MPW particulates can be include, for example, shredded plastic particles, chopped plastic particles, or plastic pellets.

In one embodiment or in combination with any of the mentioned embodiments, the MPW and/or waste plastics supplied by the plastic source 12 can comprise at least 50, at least 55, at least 60, at least 65, at least 70, at least 75, at least 80, at least 85, at least 95, or at least 99 weight percent of any one of, or in combination, polyolefins (e.g., low density polyethylene, high density polyethylene, low density polypropylene, high density polypropylene, crosslinked polyethylene, amorphous polyolefins, and the copolymers of any one of the aforementioned polyolefins), polystyrene, polyvinyl chloride (PVC), polyvinylidene chloride (PVDC), polyesters including those having repeating aromatic or cyclic units such as those containing a repeating terephthalate or naphthalate units such as PET and PEN, or those containing repeating furanate repeating units, and although within the definition of PET, it is worth mentioning also those polyesters having repeating terephthalate units and one or more residues or moieties of TMCD (2,2,4,4-tetramethyl-1,3-cyclobutanediol), CHDM (cyclohexanedimethanol), propylene glycol, or NPG (neopentyl glycol), isosorbide, isophthalic acid, 1,4-butanediol, 1,3-propane diol, and/or diethylene glycol, or combinations thereof and aliphatic polyesters such as PLA, polyglycolic acid, polycaprolactones, and polyethylene adipates, polyamides, poly(methyl methacrylate), polytetrafluoroethylene, acrylobutadienestyrene (ABS), polyurethanes, cellulosics and derivates thereof (e.g., cellulose acetate, cellulose diacetate, cellulose triacetate, cellulose acetate propionate, cellulose acetate butyrate, and regenerated cellulose such as viscose), epoxides, polyamides, phenolic resins, polyacetal, polycarbonates, polyurethane, polyphenylene-based alloys, polystyrene, styrenic compounds, vinyl based compounds, poly(methyl methacrylate), styrene acrylonitrile, thermoplastic elastomers, polyvinyl acetals (e.g., PVB), urea based polymers, melamine containing polymers, or combinations thereof.

The waste plastics supplied by the waste plastic source 12 can be any organic synthetic polymer that is solid at 25° C. at 1 atm. In one embodiment or in combination with any of the mentioned embodiments, the waste plastics can comprise thermosetting, thermoplastic, and/or elastomeric plastics. The polymer number average molecular weight can be at least 300, or at least 500, or at least 1000, or at least 5,000, or at least 10,000, or at least 20,000, or at least 30,000, or at least 50,000 or at least 70,000 or at least 90,000 or at least 100,000 or at least 130,000. The weight average molecular weight of the polymers can be at least 300, or at least 500, or at least 1000, or at least 5,000, or at least 10,000, or at least 20,000, or at least 30,000 or at least 50,000, or at least 70,000, or at least 90,000, or at least 100,000, or at least 130,000, or at least 150,000, or at least 300,000.

In one embodiment or in combination with any of the mentioned embodiments, the MPW and/or waste plastics supplied by the plastic source 12 can comprise at least 50, at least 55, at least 60, at least 65, at least 70, at least 75, at least 80, at least 85, at least 95, or at least 99 weight percent of any polyolefins (e.g. high density polyethylene, low density polyethylene, polypropylene, other polyolefins), polyethylene terephthalate (PET), polystyrene, polyamides, poly(methyl methacrylate), polytetrafluoroethylene, or combinations thereof. Moreover, in certain embodiments, the MPW and/or waste plastics supplied by the plastic source 12 may include high density polyethylene, low density polyethylene, polypropylene, other polyolefins, or combinations thereof.

In one embodiment or in combination with any of the mentioned embodiments, the MPW and/or waste plastics supplied by the plastic source 12 can comprise at least 35, at least 40, at least 45, at least 50, at least 55, at least 60, at least 65, at least 70, at least 75, at least 80, at least 85, at least 95, or at least 99 weight percent of any polyolefins (e.g. high density polyethylene, low density polyethylene, polypropylene, other polyolefins) and polyethylene terephthalate (PET).

In one embodiment or in combination with any of the mentioned embodiments, the MPW and/or waste plastics supplied by the plastic source 12 can comprise at least 50, at least 55, at least 60, at least 65, at least 70, at least 75, at least 80, at least 85, at least 95, or at least 99 weight percent of any plastics having a resin ID code numbered 1-7 within the chasing arrow triangle established by the SPI. In one embodiment or in combination with any of the mentioned embodiments, the MPW and/or waste plastics supplied by the plastic source 12 may include not more than 50, not more than 45, not more than 40, not more than 35, not more than 30, not more than 25, not more than 20, not more than 15, not more than 10, not more than 5, not more than 3, not more than 2, not more than 1, or not more than 0.5 weight percent of any plastics having a resin ID code numbered 1-7.

In one embodiment or in combination with any of the mentioned embodiments, the MPW and/or waste plastics supplied by the plastic source may comprise both plastics having a resin ID code from #1-7 and plastics not having a resin ID code from #1-7. In one embodiment or in combination with any of the mentioned embodiments, the MPW and/or waste plastics supplied by the plastic source 12 can comprise at least 10, at least 20, at least 30, at least 35, at least 40, at least 45, at least 50, at least 55, at least 60, at least 65, at least 70, at least 75, at least 80, at least 85, at least 95, or at least 99 weight percent of any plastics having or corresponding to a resin ID code numbered 3-7, or 4-7, within the chasing arrow triangle established by the SPI.

In one embodiment or in combination with any of the mentioned embodiments, the MPW includes, but is not limited to, plastic components, such as polyesters, including those having repeating aromatic or cyclic units such as those containing a repeating terephthalate or naphthalate units such as PET and PEN, or those containing repeating furanate repeating units, and although within the definition of PET, it is worth mentioning also those polyesters having repeating terephthalate units and one or more residues or moieties of TMCD (2,2,4,4-tetramethyl-1,3-cyclobutanediol), CHDM (cyclohexanedimethanol), propylene glycol, or NPG (neopentyl glycol), isosorbide, isophthalic acid, 1,4-butanediol, 1,3-propane diol, and/or diethylene glycol, or combinations thereof and aliphatic polyesters such as PLA, polyglycolic acid, polycaprolactones, and polyethylene adipates; polyolefins (e.g., low density polyethylene, high density polyethylene, low density polypropylene, high density polypropylene, crosslinked polyethylene, amorphous polyolefins, and the copolymers of any one of the aforementioned polyolefins), polyvinyl chloride (PVC), polystyrene, polytetrafluoroethylene, acrylobutadienestyrene (ABS), cellulosics such as cellulose acetate, cellulose diacetate, cellulose triacetate, cellulose acetate propionate, cellulose acetate butyrate, and regenerated cellulose such as viscose; epoxides, polyamides, phenolic resins, polyacetal, polycarbonates, polyphenylene-based alloys, poly(methyl methacrylate), styrenic containing polymers, polyurethane, vinyl-based polymers, styrene acrylonitrile, thermoplastic elastomers other than tires, and urea containing polymers and melamines.

In one embodiment or in combination with any of the mentioned embodiments, the MPW contains thermosetting polymers. Examples of the amounts of thermosetting polymers present in the MPW can be at least 1 wt. %, or at least 2 wt. %, or at least 5 wt. %, or at least 10 wt. %, or at least 15 wt. %, or at least 20 wt. %, or at least 25 wt. %, or at least 30 wt. %, or at least 40 wt. %, based on the weight of the MPW.

In one embodiment or in combination with any of the mentioned embodiments, the MPW contains plastics at least a portion of which are obtained from cellulosics, such as cellulose derivates having an acyl degree of substitution of less than 3, or 1.8 to 2.8, such as cellulose acetate, cellulose diacetate, cellulose triacetate, cellulose acetate propionate, cellulose acetate butyrate.

In one embodiment or in combination with any of the mentioned embodiments, the MPW contains plastics at least a portion of which are obtained from polymers having repeating terephthalate units, such as polyethylene terephthalate, polypropylene terephthalate, polybutylene terephthalate, and copolyesters thereof.

In one embodiment or in combination with any of the mentioned embodiments, the MPW contains plastics at least a portion of which are obtained from copolyesters having multiple dicyclohexane dimethanol moieties, 2,2,4,4-tetramethyl-1,3-cyclobutanediol moieties, or combinations thereof.

In one embodiment or in combination with any of the mentioned embodiments, the MPW contains plastics at least a portion of which are obtained from low density polyethylene, high density polyethylene, linear low-density polyethylene, polypropylene, polymethylpentene, polybutene-1, and copolymers thereof.

In one embodiment or in combination with any of the mentioned embodiments, the MPW contains plastics at least a portion of which are obtained from eyeglass frames, or crosslinked polyethylene.

In one embodiment or in combination with any of the mentioned embodiments, the MPW contains plastics at least a portion of which are obtained from plastic bottles.

In one embodiment or in combination with any of the mentioned embodiments, the MPW contains plastics at least a portion of which are obtained from diapers.

In one embodiment or in combination with any of the mentioned embodiments, the MPW contains plastics at least a portion of which are obtained from Styrofoam, or expanded polystyrene.

In one embodiment or in combination with any of the mentioned embodiments, the MPW contains plastics at least a portion of which are obtained from flashspun high density polyethylene.

In one embodiment or in combination with any of the mentioned embodiments, the MPW contains plastics having or obtained from plastics having a resin ID code numbered 1-7 within the chasing arrow triangle established by the SPI. In one embodiment or in combination with any of the mentioned embodiments, at least a portion of the MPW contains one or more plastics that are not generally mechanically recycled. These would include plastics having numbers 3 (polyvinyl chloride), 5 (polypropylene), 6 (polystyrene), and 7 (other). In one embodiment or in combination with any of the mentioned embodiments, the MPW contains at least 0.1 wt. %, or at least 0.5 wt. %, or at least 1 wt. %, or at least 2 wt. %, or at least 3 wt. %, or at least 5 wt. %, or at least 7 wt. %, or at least 10 wt. %, or at least 12 wt. %, or at least 15 wt. %, or at least 20 wt. %, or at least 25 wt. %, or at least 30 wt. %, or at least 40 wt. %, or at least or more than 50 wt. %, or at least 65 wt. %, or at least 85 wt. %, or at least 90 wt. % plastics having or corresponding to a number 3, 5, 6, 7, or a combination thereof, based on the weight of the plastics in the MPW.

In one embodiment or in combination with any of the mentioned embodiments, the MPW comprises plastics having or obtained from plastics having at least 30, at least 35, at least 40, at least 45, at least 50, at least 55, at least 60, at least 65, at least 70, at least 75, at least 80, at least 85, at least 90, at least 95, or at least 99 weight percent of at least one, two, three, or four different kinds of resin ID codes.

In one embodiment or in combination with any of the mentioned embodiments, the MPW and/or waste plastics supplied by the plastic source 12 can comprise at least 50, at least 55, at least 60, at least 65, at least 70, at least 75, at least 80, at least 85, at least 95, or at least 99 weight percent of at least one post-consumer plastic and/or at least one post-industrial (pre-consumer) plastic. As used herein, a "post-consumer plastic" is one that has been used at least once for its intended application for any duration of time regardless of wear, has been sold to an end use customer, or has been discarded into a recycle bin by any person or entity other than a manufacturer or business engaged in the manufacture or sale of the material.

Furthermore, a "post-industrial plastic" (or "pre-consumer plastic") includes all manufactured recyclable organic plastics that are not post-consumer plastics, such as a material that has been created or processed by a manufacturer and has not been used for its intended application, has not been sold to the end use customer, or has been discarded or transferred by a manufacturer or any other entity engaged in the sale or disposal of the material. Examples of post-industrial (pre-consumer) plastics include rework, regrind, scrap, trim, out of specification materials, and finished materials transferred from a manufacturer to any downstream customer (e.g., manufacturer to wholesaler to distributor) but not yet used or sold to the end use customer.

The form of the MPW and/or waste plastics supplied by the plastic source 12 is not limited, and can include any of the forms of articles, products, materials, or portions thereof. A portion of an article can take the form of sheets, extruded shapes, moldings, films, carpet, laminates, foam pieces, chips, flakes, particles, agglomerates, briquettes, powder, shredded pieces, long strips, randomly shaped pieces having a wide variety of shapes, or any other form other than the original form of the article and adapted to feed a pyrolysis unit.

In one embodiment or in combination with any of the mentioned embodiments, the MPW and/or waste plastics supplied by the plastic source 12 can comprise at least 50, at least 55, at least 60, at least 65, at least 70, at least 75, at least 80, at least 85, at least 95, or at least 99 weight percent of recycled textiles and/or recycled carpet, such as synthetic fibers, rovings, yarns, nonwoven webs, cloth, fabrics and products made from or containing any of the aforementioned plastics. The textiles can comprise woven, knitted, knotted, stitched, tufted, felted, embroidered, laced, crocheted, braided, or nonwoven webs and materials. The textiles may include fabrics, fibers separated from a textile or other product containing fibers, scrap or off spec fibers or yarns or fabrics, or any other source of loose fibers and yarns. Furthermore, the textiles may also include staple fibers, continuous fibers, threads, tow bands, twisted and/or spun yarns, grey fabrics made from yarns, finished fabrics produced by wet processing gray fabrics, garments made from the finished fabrics, or any other fabrics.

Examples of recycled textiles in the apparel industry that may be used include sports coats, suits, trousers and casual or work pants, shirts, socks, sportswear, dresses, intimate apparel, outerwear such as rain jackets, cold temperature jackets and coats, sweaters, protective clothing, uniforms, and accessories such as scarves, hats, and gloves. Examples of textiles in the interior furnishing category that may be used include furniture upholstery and slipcovers, carpets and rugs, curtains, bedding such as sheets, pillow covers, duvets, comforters, mattress covers, linens, tablecloths, towels, washcloths, and blankets. Examples of industrial textiles that may be used include transportation seats, floor mats, trunk liners, and headliners, outdoor furniture and cushions, tents, backpacks, luggage, ropes, conveyor belts, calendar roll felts, polishing cloths, rags, soil erosion fabrics and geotextiles, agricultural mats and screens, personal protective equipment, bullet proof vests, medical bandages, sutures, tapes, and the like.

The MPW may contain recycle (post-consumer or post-industrial (or pre-consumer) textiles. Textiles may contain natural and/or synthetic fibers, rovings, yarns, nonwoven webs, cloth, fabrics and products made from or containing any of the aforementioned items, Textiles can be woven, knitted, knotted, stitched, tufted, pressing of fibers together such as would be done in a felting operation, embroidered, laced, crocheted, braided, or nonwoven webs and materials. Textiles as used herein include fabrics, and fibers separated from a textile or other product containing fibers, scrap or off spec fibers or yarns or fabrics, or any other source of loose fibers and yarns. A textile also includes staple fibers, continuous fibers, threads, tow bands, twisted and/or spun yarns, grey fabrics made from yarns, finished fabrics produced by wet processing gray fabrics, and garments made from the finished fabrics or any other fabrics. Textiles include apparels, interior furnishings, and industrial types of textiles. Textiles also include post-industrial textiles or post-consumer textiles or both.

Examples of textiles in the apparel category (things humans wear or made for the body) include sports coats, suits, trousers and casual or work pants, shirts, socks, sportswear, dresses, intimate apparel, outerwear such as rain jackets, cold temperature jackets and coats, sweaters, protective clothing, uniforms, and accessories such as scarves, hats, and gloves. Examples of textiles in the interior furnishing category include furniture upholstery and slipcovers, carpets and rugs, curtains, bedding such as sheets, pillow covers, duvets, comforters, mattress covers; linens, table cloths, towels, washcloths, and blankets. Examples of industrial textiles include transportation (auto, airplanes, trains, buses) seats, floor mats, trunk liners, and headliners; outdoor furniture and cushions, tents, backpacks, luggage, ropes, conveyor belts, calendar roll felts, polishing cloths, rags, soil erosion fabrics and geotextiles, agricultural mats and screens, personal protective equipment, bullet proof vests, medical bandages, sutures, tapes, and the like.

The nonwoven webs that are classified as textiles do not include the category of wet laid nonwoven webs and articles made therefrom. While a variety of articles having the same function can be made from a dry or wet laid process, the article made from the dry laid nonwoven web is classified as a textile. Examples of suitable articles that may be formed from dry laid nonwoven webs as described herein can include those for personal, consumer, industrial, food service, medical, and other types of end uses. Specific examples can include, but are not limited to, baby wipes, flushable wipes, disposable diapers, training pants, feminine hygiene products such as sanitary napkins and tampons, adult incontinence pads, underwear, or briefs, and pet training pads.

Other examples include a variety of different dry or wet wipes, including those for consumer (such as personal care or household) and industrial (such as food service, health care, or specialty) use. Nonwoven webs can also be used as padding for pillows, mattresses, and upholstery, batting for quilts and comforters. In the medical and industrial fields, nonwoven webs of the present invention may be used for medical and industrial face masks, protective clothing, caps, and shoe covers, disposable sheets, surgical gowns, drapes, bandages, and medical dressings.

Additionally, nonwoven webs as described herein may be used for environmental fabrics such as geotextiles and tarps, oil and chemical absorbent pads, as well as building materials such as acoustic or thermal insulation, tents, lumber and soil covers and sheeting. Nonwoven webs may also be used for other consumer end use applications, such as for, carpet backing, packaging for consumer, industrial, and agricultural goods, thermal or acoustic insulation, and in various types of apparel. The dry laid nonwoven webs as described herein may also be used for a variety of filtration applications, including transportation (e.g., automotive or aeronautical), commercial, residential, industrial, or other specialty applications. Examples can include filter elements for consumer or industrial air or liquid filters (e.g., gasoline, oil, water), including nanofiber webs used for microfiltration, as well as end uses like tea bags, coffee filters, and dryer sheets. Further, nonwoven webs as described herein may be used to form a variety of components for use in automobiles, including, but not limited to, brake pads, trunk liners, carpet tufting, and under padding.

The textiles can include single type or multiple type of natural fibers and/or single type or multiple type of synthetic fibers. Examples of textile fiber combinations include all natural, all synthetic, two or more type of natural fibers, two or more types of synthetic fibers, one type of natural fiber and one type of synthetic fiber, one type of natural fibers and two or more types of synthetic fibers, two or more types of natural fibers and one type of synthetic fibers, and two or more types of natural fibers and two or more types of synthetic fibers.

Natural fibers include those that are plant derived or animal derived. Natural fibers can be cellulosics, hemicellulosics, and lignins. Examples of plant derived natural fibers include hardwood pulp, softwood pulp, and wood flour; and other plant fibers including those in wheat straw, rice straw, abaca, coir, cotton, flax, hemp, jute, bagasse, kapok, papyrus, ramie, rattan, vine, kenaf, abaca, henequen, sisal, soy, cereal straw, bamboo, reeds, esparto grass, bagasse, Sabai grass, milkweed floss fibers, pineapple leaf fibers, switch grass, lignin-containing plants, and the like. Examples of animal derived fibers include wool, silk, mohair, cashmere, goat hair, horse hair, avian fibers, camel hair, angora wool, and alpaca wool.

Synthetic fibers are those fibers that are, at least in part, synthesized or derivatized through chemical reactions, or regenerated, and include, but are not limited to, rayon, viscose, mercerized fibers or other types of regenerated cellulose (conversion of natural cellulose to a soluble cellulosic derivative and subsequent regeneration) such as lyocell (also known as Tencel), Cupro, Modal, acetates such as polyvinyl acetate, polyamides including nylon, polyesters such as PET, olefinic polymers such as polypropylene and polyethylene, polycarbonates, poly sulfates, poly sulfones, polyethers such as polyether-urea known as Spandex or elastane, polyacrylates, acrylonitrile copolymers, polyvinylchloride (PVC), polylactic acid, polyglycolic acid, sulfopolyester fibers, and combinations thereof.

The textiles can be in any of the forms mentioned above, such as size reduction via chopping, shredding, harrowing, confrication, pulverizing, or cutting a feedstock of textiles to make size reduced textiles. The textiles can also be densified. Examples of processes that densify include those that agglomerate the textiles through heat generated by frictional forces or particles made by extrusion or other external heat applied to the textile to soften or melt a portion or all of the textile.

In one embodiment or in combination with any of the mentioned embodiments, the amount of textiles (including textile fibers) in the MPW is at least 0.1 wt. %, or at least 0.5 wt. %, or at least 1 wt. %, or at least 2 wt. %, or at least 5 wt. %, or at least 8 wt. %, or at least 10 wt. %, or at least 15 wt. %, or at least 20 wt. % material obtained from textiles or textile fibers, based on the weight of the MPW. In one embodiment or in combination with any of the mentioned embodiments, the amount of textiles (including textile fibers) in the MPW is not more than 50, not more than 40, not more than 30, not more than 20, not more than 15, not more than 10, not more than 8, not more than 5, not more than 2, not more than 1, not more than 0.5, not more than 0.1, not more than 0.05, not more than 0.01, or not more than 0.001 wt. %, based on the weight of the MPW.

Turning back to FIG. 1, the MPW and/or waste plastics supplied by the plastic source 12 may be introduced into a feedstock pretreatment system 14. In one embodiment or in combination with any of the mentioned embodiments, the MPW and/or waste plastics introduced into the feedstock pretreatment system 14 may comprise a solids content of at least 50, at least 55, at least 60, at least 65, at least 70, at least 75, at least 80, at least 85, at least 90, at least 95, or at least 99 weight percent.

While in the feedstock pretreatment system 14, the introduced MPW and/or waste plastics may undergo one or more pretreatments to facilitate the subsequent pyrolysis reaction and/or enrich the resulting pyrolysis products. In one embodiment or in combination with any of the mentioned embodiments, the introduced MPW and/or waste plastics may undergo preprocessing while in the pretreatment system 14. As used herein, "preprocessing" refers to preparing waste plastic for chemical modification using one or more of the following steps: (i) comminuting, (ii) particulating, (iii) washing, (iv) drying, and/or (v) separating. Furthermore, in one embodiment or in combination with any of the mentioned embodiments, the feedstock pretreatment system 14 can comprise a preprocessing facility. As used herein, a "preprocessing facility" refers to a facility that includes all equipment, lines, and controls necessary to carry out preprocessing of waste plastic.

Exemplary pretreatments may include, for example, comminuting, particulating, washing, drying, mechanical agitation, flotation, size reduction, separation, dehalogenation, or any combination thereof. In one embodiment or in combination with any of the mentioned embodiments, the introduced MPW and/or waste plastic may be subjected to comminuting, mechanical agitation, and/or particulating to reduce the particle size of the waste plastic.

For example, this may occur by chopping, shredding, harrowing, confrication, pulverizing, cutting, molding, compression, or dissolution in a solvent. The comminuting, mechanical agitation, and/or particulating can be conducted by any mixing, shearing, or grinding device known in the art and may reduce the average particle size of the introduced plastics by at least 10, at least 25, at least 50, at least 60, at least 70, at least 80, at least 90, or at least 95 percent. For instance, after comminuting, mechanical agitation, and/or particulating, the ground MPW and/or waste plastic may have an average particle size of at least 0.1, at least 0.2, at least 0.3, or at least 0.4 and/or not more than 0.9, not more than 0.8, not more than 0.7, not more than 0.6, or not more than 0.5 inches.

In one embodiment or in combination with any of the mentioned embodiments, the feedstock pretreatment system 14 may comprise at least one separator unit, optionally in fluid communication with the aforementioned mixing, shearing, or grinding device, configured to further purify the MPW and/or waste plastics by removing undesirable components and plastics. The separator unit may comprise a filter, a hydrocyclone separator, a fractionator, a centrifuge, a floatation tank, or combinations thereof. In one embodiment or in combination with any of the mentioned embodiments, the pretreatment system 14 may comprise at least one grinding unit and at least one separator unit, the order of which may be modified as necessary according to the plastic feedstock being introduced into the feedstock pretreatment system 14. Generally, in one embodiment or in combination with any of the mentioned embodiments, the separator may be placed downstream of the grinding unit.

The feedstock pretreatment system 14, via the separator, may remove at a least a portion of undesirable plastics, such as polyvinyl chloride (PVC) and polyethylene terephthalate (PET), from the MPW and/or waste plastics introduced into the pretreatment system 14. In one embodiment or in combination with any of the mentioned embodiments, the feedstock pretreatment system 14 may remove at least 5, at least 10, at least 15, at least 20, at least 25, at least 30, at least 35, at least 40, at least 45, at least 50, at least 60, at least 65, at least 70, at least 75, at least 80, at least 85, at least 90, at least 95, or at least 99 percent of the polyvinyl chloride (PVC) and/or polyethylene terephthalate (PET) originally present in the MPW and/or waste plastics supplied by the waste plastic source 12.

In one embodiment or in combination with any of the mentioned embodiments, the feedstock pretreatment system 14 may comprise a floatation tank and/or a hydrocyclone that is capable of separating the undesirable plastics from the desired plastics in the MPW and/or waste plastics based on the densities of the plastics in a liquid medium, such as water. In other words, these floatation tanks and hydrocyclones can use a density separation process to separate out the undesirable plastics from the MPW and/or waste plastics from the waste plastic source 12. As used herein, a "density separation process" refers to a process for separating materials based, at least in part, upon the respective densities of the materials.

In the floatation tank, the MPW and/or the waste plastics from the waste plastic source 12 can be introduced into a liquid medium, such as saltwater, in order to separate the desirable plastics from the undesirable plastics via a sink-float density separation based on the target separation density. As used herein, a "sink-float density separation" refers to a density separation process where the separation of materials is primarily caused by floating or sinking in a selected liquid medium. Furthermore, as used herein, the "target separation density" refers to density above which materials subjected to a density separation process are preferentially separated into the higher-density output and below which materials are separated in the lower-density output. In such embodiments, undesirable plastics (e.g., PET and/or PVC) may be removed from the MPW and/or the waste plastics.

In one embodiment or in combination with any of the mentioned embodiments, the liquid medium comprises water. Salts, saccharides, and/or other additives can be added to the liquid medium, for example to increase the density of the liquid medium and adjust the target separation density of the sink-float separation stage. In one embodiment or in combination with any of the mentioned embodiments, the liquid medium comprises a concentrated salt solution.

In one or more such embodiments, the salt is sodium chloride. In one or more other embodiments, however, the salt is a non-halogenated salt, such as acetates, carbonates, citrates, nitrates, nitrites, phosphates, and/or sulfates. The liquid medium can comprise a concentrated salt solution comprising sodium bromide, sodium dihydrogen phosphate, sodium hydroxide, sodium iodide, sodium nitrate, sodium thiosulfate, potassium acetate, potassium bromide, potassium carbonate, potassium hydroxide, potassium iodide, calcium chloride, cesium chloride, iron chloride, strontium chloride, zinc chloride, manganese sulfate, zinc sulfate, and/or silver nitrate. The liquid medium can comprise a saccharide, such as sucrose. The liquid medium can comprise carbon tetrachloride, chloroform, dichlorobenzene, dimethyl sulfate, and/or trichloro ethylene. The particular components and concentrations of the liquid medium may be selected depending on the desired target separation density of the separation stage.

In the hydrocyclone, the MPW and/or the waste plastics from the waste plastic source 12 can be introduced into a liquid medium, such as saltwater, in order to separate the desirable plastics from the undesirable plastics based on centrifugal density separation. As used herein, the "centrifugal density separation" refers to a density separation process where the separation of particles is primarily caused by centrifugal forces. In such embodiments, undesirable plastics (e.g., PET and/or PVC) may be removed from the MPW and/or the waste plastics.

In one embodiment or in combination with any of the mentioned embodiments, the feedstock pretreatment system 14 may comprise one or more systems or components capable of at least partially dehalogenating the MPW and/or the waste plastics introduced into the feedstock pretreatment system 14. More particularly, the pretreatment system 14 can remove at least a portion of the halogen-containing (e.g., chlorine-containing) compounds from the MPW and/or the waste plastics introduced into the pretreatment system 14 to thereby form a dehalogenated feedstock. The removed halogen waste comprising the removed halogen-containing compounds (e.g., chlorine-containing plastics and compounds such as HCl) may be discarded from the pyrolysis facility 10.

In one embodiment or in combination with any of the mentioned embodiments, the dehalogenating process within the pretreatment system 14 may comprise one or more of the following steps: (i) physically separating solid halogen-containing waste plastic from at least one other type of waste plastic (e.g., by use of at least one floatation tank and/or at least one hydrocyclone); (ii) melting at least a portion of the MPW and/or waste plastics from the waste plastic source 12 and physically separating the melted halogen-containing waste plastic from at least one other type of melted waste plastic; or (iii) heating the waste halogen-containing plastic in the MPW and/or waste plastics from the waste plastic source 12 to a temperature sufficient enough to crack at least a portion of the waste halogen-containing plastic to release a halogen-containing gas, such as gaseous hydrogen chloride, and then venting off the halogen-containing gas. The melting of step (ii) and/or the heating of step (iii) may occur at a temperature of at least 150° C., at least 175° C., at least 200° C., at least 225° C., at least 250° C., at least 275° C., or at least 300° C. and/or not more than 400° C., not more than 375° C., or not more than 350° C.

More particularly, the melting of step (ii) and/or the heating of step (iii) may occur at a temperature in the range of 150° C. to 400° C., 175° C. to 375° C., or 250° C. to 375° C. The venting can be carried out using a column with a venting system, a piping system, a polycondensation reactor, a wiped film reactor, an agitated reactor, a vacuum, or a separator that is capable of venting off at least a portion of the gaseous halogen-containing byproducts, such as gaseous HCl.

Furthermore, in one embodiment or in combination with any of the mentioned embodiments, the gaseous halogen-containing byproducts producing during the melting of step (ii) and/or the heating of step (iii) may be subsequently contacted with a halogen scavenger in an absorbent bed in order to remove it from the system. The halogen scavenger may comprise a metal oxide, a metal hydroxide, a carbon composite, or a combination thereof. For example, the halogen scavenger may comprise a porous alumina, a modified porous alumina, a slaked lime, a calcium carbonate, or combinations thereof.

In one embodiment or in combination with any of the mentioned embodiments, the pretreatment system 14 may remove at least 5, at least 10, at least 15, at least 20, at least 25, at least 30, at least 35, at least 40, at least 45, at least 50, at least 60, at least 65, at least 70, at least 75, at least 80, at least 85, at least 90, at least 95, or at least 99 percent of the halogen originally present in the MPW and/or waste plastics derived from the waste plastic source 12.

In one embodiment or in combination with any of the mentioned embodiments, the resulting dehalogenated feedstock leaving the pretreatment system 14 may comprise a halogen content, such as a chlorine content, of not more than 1,000, not more than 500, not more than 400, not more than 300, not more than 250, not more than 200, not more than 150, not more than 100, not more than 90, not more than 80, not more than 70, not more than 60, not more than 50, not more than 40, not more than 30, not more than 20, not more than 10, or not more than 5 ppm.

Turning back to FIG. 1, the pretreated plastic feedstock exiting the pretreatment system 14 can be introduced into a plastic feed system 16. The plastic feed system 16 may be configured to introduce the plastic feed into the pyrolysis reactor 18. The plastic feed system 16 can comprise any system known in the art that is capable of feeding the solid plastic feed into the pyrolysis reactor 18. In an embodiment or in combination with any of the embodiments mentioned herein, the plastic feed system 16 can comprise one or more of a screw feeder, a hopper, a paddle feeder, a rotary airlock, a pneumatic conveyance system, a mechanic metal train or chain, or combinations thereof.

In one embodiment or in combination with any of the mentioned embodiments, the plastic-containing feedstock exiting the pretreatment system 14 and introduced into the pyrolysis reactor 18 can comprise at least 30, at least 35, at least 40, at least 45, at least 50, at least 55, at least 60, at least 65, at least 70, at least 75, at least 80, at least 85, at least 90, at least 95, or at least 99 weight percent of at least one, two, three, four, five, or six different kinds of recycled waste plastics. Reference to a "kind" may be determined by resin ID code 1-7 or a specific type of waste plastics (e.g., high density polyethylene).

In one embodiment or in combination with any of the mentioned embodiments, the plastic-containing feedstock exiting the pretreatment system 14 and introduced into the pyrolysis reactor 18 can comprise at least 25, at least 30, at least 35, at least 40, at least 45, at least 50, at least 55, at least 60, at least 65, at least 70, at least 75, at least 80, at least 85, at least 90, at least 95, or at least 99 weight percent of any polyolefin, such as a high density polyethylene, low density polyethylene, polypropylene, other polyolefins, or combinations thereof.

In one embodiment or in combination with any of the mentioned embodiments, the plastic-containing feedstock exiting the pretreatment system 14 and introduced into the pyrolysis reactor 18 can comprise not more than 90, not more than 80, not more than 70, not more than 60, not more than 50, not more than 40, not more than 30, not more than 20, not more than 10, not more than 9, not more than 8, not more than 7, not more than 6, not more than 5, not more than 4, not more than 3, not more than 2, or not more than 1 weight percent of polyethylene terephthalate (PET) and/or polyvinyl chloride (PVC).

While in the pyrolysis reactor 18, at least a portion of the plastic feed may be subjected to a pyrolysis reaction that produces a pyrolysis effluent comprising a pyrolysis oil, a pyrolysis gas, and a pyrolysis residue. As used herein, "pyrolysis" refers to the thermal decomposition of one or more organic materials at elevated temperatures in an inert (i.e., substantially oxygen free) atmosphere. While not wishing to be bound by any particular theory, pyrolysis of waste plastic can function as a form of chemical recycling.

Generally, pyrolysis is a process that involves the chemical and thermal decomposition of the introduced feed. Although all pyrolysis processes may be generally characterized by a reaction environment that is substantially free of oxygen, pyrolysis processes may be further defined, for example, by the pyrolysis reaction temperature within the reactor, the residence time in the pyrolysis reactor, the reactor type, the pressure within the pyrolysis reactor, and the presence or absence of pyrolysis catalysts.

In one embodiment or in combination with any of the mentioned embodiments, the pyrolysis reactor 18 can be, for example, a screw extruder, a tubular reactor, a tank, a stirred tank reactor, a riser reactor, a fixed bed reactor, a fluidized bed reactor, a rotary kiln, a vacuum reactor, a microwave reactor, or an autoclave.

In one embodiment or in combination with any of the mentioned embodiments, the pyrolysis reaction can involve heating and converting the plastic feedstock in an atmosphere that is substantially free of oxygen or in an atmosphere that contains less oxygen relative to ambient air. For example, the atmosphere within the pyrolysis reactor 18 may comprise not more than 5, not more than 4, not more than 3, not more than 2, not more than 1, or not more than 0.5 percent of oxygen gas based on the interior volume of the reactor 18.

In one embodiment or in combination with any of the mentioned embodiments, a lift gas and/or a feed gas may be used to introduce the plastic feedstock into the pyrolysis reactor 18 and/or facilitate various reactions within the pyrolysis reactor 18. For instance, the lift gas and/or the feed gas may comprise, consist essentially of, or consist of nitrogen, carbon dioxide, and/or steam. The lift gas and/or feed gas may be added with the plastic waste prior to introduction into the pyrolysis reactor 18 and/or may be added directly to the pyrolysis reactor.

In one embodiment or in combination with any of the mentioned embodiments, the pyrolysis process may be carried out in the presence of a lift gas and/or a feed gas comprising, consisting essentially of, or consisting of steam. For example, the pyrolysis process may be carried out in the presence of a feed gas and/or lift gas comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 weight percent of steam.

Additionally, or alternatively, in one embodiment or in combination with any of the mentioned embodiments, the pyrolysis process is carried out in the presence of a feed gas and/or a lift gas comprising not more than 99, not more than 90, not more than 80, not more than 70, not more than 60, not more than 50, not more than 40, not more than 30, or not more than 20 weight percent of steam. Although not wishing to be bound by theory, it is believed that the presence of steam in the pyrolysis reactor 18 can facilitate the water-gas shift reaction, which can facilitate the removal of any halogen compounds that may be produced during the pyrolysis reaction. The steam may be added with the plastic waste prior to introduction into the pyrolysis reactor 18 and/or may be added directly to the pyrolysis reactor.

Additionally or alternatively, in one embodiment or in combination with any of the mentioned embodiments, the pyrolysis process may be carried out in the presence of a lift gas and/or a feed gas comprising, consisting essentially of, or consisting of a reducing gas, such as hydrogen, carbon monoxide, or a combination thereof. The reducing gas may function as a feed gas and/or a lift gas and may facilitate the introduction of the plastic feed into the pyrolysis reactor 18. The reducing gas may be added with the plastic waste prior to introduction into the pyrolysis reactor 18 and/or may be added directly to the pyrolysis reactor.

In one embodiment or in combination with any of the mentioned embodiments, the pyrolysis process may be carried out in the presence of a feed gas and/or lift gas comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 weight percent of at least one reducing gas. Additionally or alternatively, in, the pyrolysis process can be carried out in the presence of a feed gas and/or a lift gas comprising not more than 99, not more than 90, not more than 80, not more than 70, not more than 60, not more than 50, not more than 40, not more than 30, or not more than 20 weight percent of at least one reducing gas.

In one embodiment or in combination with any of the mentioned embodiments, the pyrolysis process may be carried out in the presence of a feed gas and/or lift gas comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 weight percent of hydrogen. Additionally, or alternatively, the pyrolysis process is carried out in the presence of a feed gas and/or a lift gas comprising not more than 99, not more than 90, not more than 80, not more than 70, not more than 60, not more than 50, not more than 40, not more than 30, or not more than 20 weight percent of hydrogen.

In one embodiment or in combination with any of the mentioned embodiments, the pyrolysis process may be carried out in the presence of a feed gas and/or lift gas comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 weight percent of carbon monoxide. Additionally or alternatively, the pyrolysis process is carried out in the presence of a feed gas and/or a lift gas comprising not more than 99, not more than 90, not more than 80, not more than 70, not more than 60, not more than 50, not more than 40, not more than 30, or not more than 20 weight percent of carbon monoxide.

Furthermore, the temperature in the pyrolysis reactor 18 can be adjusted so as to facilitate the production of certain end products. In one embodiment or in combination with any of the mentioned embodiments, the pyrolysis temperature in the pyrolysis reactor 18 can be at least 325° C., at least 350° C., at least 375° C., at least 400° C., at least 425° C., at least 450° C., at least 475° C., at least 500° C., at least 525° C., at least 550° C., at least 575° C., at least 600° C., at least 625° C., at least 650° C., at least 675° C., at least 700° C., at least 725° C., at least 750° C., at least 775° C., or at least 800° C.

Additionally or alternatively, the pyrolysis temperature in the pyrolysis reactor 18 can be not more than 1,100° C., not more than 1,050° C., not more than 1,000° C., not more than 950° C., not more than 900° C., not more than 850° C., not more than 800° C., not more than 750° C., not more than 700° C., not more than 650° C., not more than 600° C., not more than 550° C., not more than 525° C., not more than 500° C., not more than 475° C., not more than 450° C., not more than 425° C., or not more than 400° C. More particularly, the pyrolysis temperature in the pyrolysis reactor 18 can range from 325 to 1,100° C., 350 to 900° C., 350 to 700° C., 350 to 550° C., 350 to 475° C., 425 to 1,100° C., 425 to 800° C., 500 to 1,100° C., 500 to 800° C., 600 to 1,100° C., 600 to 800° C., 650 to 1,000° C., or 650 to 800° C.

In one embodiment or in combination with any of the mentioned embodiments, the residence times of the plastic feedstocks within the pyrolysis reactor 18 can be at least 0.1, at least 0.2, at least 0.3, at least 0.5, at least 1, at least 1.2, at least 1.3, at least 2, at least 3, or at least 4 seconds. Alternatively, in the residence times of the plastic feedstocks within the pyrolysis reactor 18 can be at least 1, at least 2, at least 3, at least 4, at least 5, at least 6, at least 7, at least 8, at least 9, at least 10, at least 20, at least 30, at least 45, at least 60, at least 75, or at least 90 minutes. Additionally, or alternatively, the residence times of the plastic feedstocks within the pyrolysis reactor 18 can be not more than 6, not more than 5, not more than 4, not more than 3, not more than 2, not more than 1, or not more than 0.5 hours.

Furthermore, the residence times of the plastic feedstocks within the pyrolysis reactor 18 can be not more than 100, not more than 90, not more than 80, not more than 70, not more than 60, not more than 50, not more than 40, not more than 30, not more than 20, not more than 10, not more than 9, not more than 8, not more than 7, not more than 6, not more than 5, not more than 4, not more than 3, not more than 2, or not more than 1 seconds. More particularly, in one embodiment or in combination with any of the mentioned embodiments, the residence times of the plastic feedstocks within the pyrolysis reactor 18 can range from 0.1 to 10 seconds, 0.5 to 10 seconds, 30 minutes to 4 hours, or 30 minutes to 3 hours, or 1 hour to 3 hours, or 1 hour to 2 hours.

In one embodiment or in combination with any of the mentioned embodiments, the pressure within the pyrolysis reactor 18 can be maintained at a pressure of at least 0.1, at least 0.2, or at least 0.3 bar and/or not more than 60, not more than 50, not more than 40, not more than 30, not more than 20, not more than 10, not more than 8, not more than 5, not more than 2, not more than 1.5, or not more than 1.1 bar. In an embodiment or in combination with any of the embodiments mentioned herein, the pressure within the pyrolysis reactor 18 can be maintained at about atmospheric pressure or within the range of 0.1 to 100 bar, or 0.1 to 60 bar, or 0.1 to 30 bar, or 0.1 to 10 bar, or 1.5 bar, 0.2 to 1.5 bar, or 0.3 to 1.1 bar.

In one embodiment or in combination with any of the mentioned embodiments, a pyrolysis catalyst may be introduced into the plastic feedstock prior to introduction into the pyrolysis reactor 18 and/or introduced directly into the pyrolysis reactor 18. Furthermore, the catalyst can comprise: (i) a solid acid, such as a zeolite (e.g., ZSM-5, Mordenite, Beta, Ferrierite, and/or zeolite-Y); (ii) a super acid, such as sulfonated, phosphated, or fluorinated forms of zirconia, titania, alumina, silica-alumina, and/or clays; (iii) a solid base, such as metal oxides, mixed metal oxides, metal hydroxides, and/or metal carbonates, particularly those of alkali metals, alkaline earth metals, transition metals, and/or rare earth metals; (iv) hydrotalcite and other clays; (v) a metal hydride, particularly those of alkali metals, alkaline earth metals, transition metals, and/or rare earth metals; (vi) an alumina and/or a silica-alumina; (vii) a homogeneous catalyst, such as a Lewis acid, a metal tetrachloroaluminate, or an organic ionic liquid; (viii) activated carbon; or (ix) combinations thereof.

In one embodiment or in combination with any of the mentioned embodiments, the pyrolysis catalyst can comprise a homogeneous catalyst or a heterogeneous catalyst.

In one embodiment or in combination with any of the mentioned embodiments, the pyrolysis catalyst can comprise a mesostructured catalyst, such as MCM-41, FSM-16, Al-SBA-15, or combinations thereof.

In one embodiment or in combination with any of the mentioned embodiments, the pyrolysis catalyst can comprise a silica-alumina, an alumina, a mordenite, a zeolite, a microporous catalyst, a macroporous catalyst, or a combination thereof.

In one embodiment or in combination with any of the mentioned embodiments, the pyrolysis reaction in the pyrolysis reactor 18 occurs in the substantial absence of a catalyst. In such embodiments, a non-catalytic, heat-retaining inert additive may still be introduced into the pyrolysis reactor 18, such as sand, in order to facilitate the heat transfer within the reactor 18. Such catalyst-free pyrolysis processes may be referred to as "thermal pyrolysis."

In one embodiment or in combination with any of the mentioned embodiments, the pyrolysis reaction in the pyrolysis reactor 18 may occur in the substantial absence of a pyrolysis catalyst, at a temperature in the range of 350 to 550° C., at a pressure ranging from 0.1 to 60 bar, and at a residence time of 0.2 seconds to 4 hours, or 0.5 hours to 3 hours.

Referring again to FIG. 1, the pyrolysis effluent 20 exiting the pyrolysis reactor 18 generally comprises the pyrolysis gas, pyrolysis oil, and pyrolysis residue. Upon exiting the pyrolysis reactor 18, the pyrolysis oil may be in the form of a vapor due to the heat of the pyrolysis reactor 18.

As used herein, a "pyrolysis oil" or "pyoil" refers to a composition obtained from pyrolysis that is liquid at 25° C. and 1 atm.

As used herein, a "pyrolysis gas" refers to a composition obtained from pyrolysis that is gaseous at 25° C.

As used herein, a "pyrolysis residue" refers to a composition obtained from pyrolysis that is not pyrolysis gas or pyrolysis oil and that comprises predominantly pyrolysis char and pyrolysis heavy waxes. Generally, the pyrolysis residue may comprise particles of char, ash, heavy waxes, unconverted plastic solids, and/or spent catalyst (if a catalyst is utilized). As used herein, "pyrolysis char" refers to a carbon-containing composition obtained from pyrolysis that is solid at 200° C. and 1 atm. As used herein, "pyrolysis heavy waxes" refer to C20+ hydrocarbons obtained from pyrolysis that are not pyrolysis char, pyrolysis gas, or pyrolysis oil.

For example, as shown in FIG. 1, the pyrolysis oil fraction may be included in the pyrolysis effluent 20 exiting pyrolysis reactor 18, in line 36 exiting the fractionator 34, line 40 exiting from the quench system, or line 42 exiting the hydroprocessing unit. In one embodiment or in combination with any of the mentioned embodiments, the solids in the pyrolysis effluent 20 may comprise particles of char, ash, unconverted plastic solids, and/or spent catalyst (if a catalyst is utilized).

In one embodiment or in combination with any of the mentioned embodiments, the pyrolysis effluent 20 may comprise at least 1, at least 5, at least 10, at least 15, at least 20, at least 25, at least 30, at least 35, at least 40, at least 45, at least 50, at least 55, at least 60, at least 65, at least 70, or at least 75 weight percent of the pyrolysis oil, which may be in the form of vapors in the pyrolysis effluent 20 upon exiting the heated reactor 18; however, these vapors may be subsequently condensed into the resulting pyrolysis oil. Additionally or alternatively, the pyrolysis effluent 20 may comprise not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, or not more than 25 weight percent of the pyrolysis oil, which may be in the form of vapors in the pyrolysis effluent 20 upon exiting the heated reactor 18. In one embodiment or in combination with any of the mentioned embodiments, the pyrolysis effluent 20 may comprise in the range of 20 to 99 weight percent, 25 to 80 weight percent, 30 to 85, 30 to 80, 30 to 75, 30 to 70, or 30 to 65 weight percent of the pyrolysis oil.

In one embodiment or in combination with any of the mentioned embodiments, the pyrolysis effluent 20 may comprise at least 1, at least 5, at least 10, at least 15, at least 20, at least 25, at least 30, at least 35, at least 40, at least 45, at least 50, at least 55, at least 60, at least 65, at least 70, at least 75, or at least 80 weight percent of the pyrolysis gas. Additionally, or alternatively, the pyrolysis effluent 20 may comprise not more than 99, not more than 95, not more than 90, not more than 85, not more than 80, not more than 75, not more than 70, not more than 65, not more than 60, not more than 55, not more than 50, or not more than 45 weight percent of the pyrolysis gas. The pyrolysis effluent 20 may comprise 1 to 90, 10 to 85, 15 to 85, 20 to 80, 25 to 80, 30 to 75, or 35 to 75 weight percent of the pyrolysis gas.

In one embodiment or in combination with any of the mentioned embodiments, the pyrolysis effluent 20 may comprise at least 0.5, at least 1, at least 2, at least 3, at least 4, at least 5, at least 6, at least 7, at least 8, at least 9, or at least 10 weight percent of the pyrolysis residue. Additionally, or alternatively, the pyrolysis effluent 20 may comprise not more than 60, not more than 50, not more than 40, not more than 30, not more than 25, not more than 20, not more than 15, not more than 10, not more than 9, not more than 8, not more than 7, not more than 6, or not more than 5 weight percent of the pyrolysis residue. The pyrolysis effluent 20 may comprise in the range of 0.1 to 25, 1 to 15, 1 to 8, or 1 to 5 weight percent of the pyrolysis residue.

In one embodiment or in combination with any of the mentioned embodiments, the pyrolysis effluent 20 may comprise not more than 15, not more than 14, not more than 13, not more than 12, not more than 11, not more than 10, not more than 9, not more than 8, not more than 7, not more than 6, not more than 5, not more than 4, not more than 3, not more than 2, not more than 1, or not more than 0.5 weight percent of free water. As used herein, "free water" refers to water previously added to the pyrolysis unit and water generated in the pyrolysis unit.

As depicted in FIG. 1, the conversion effluent 20 from the pyrolysis reactor 18 can be introduced into a solids separator 22. The solids separator 22 can be any conventional device capable of separating solids and heavier waxes from gas and vapors such as, for example, a cyclone separator, a multi-stage separator, a detrainment separator, or a gas filter. In one embodiment or in combination with any of the mentioned embodiments, the solids separator 22 removes a substantial portion of the solids and heavier waxes from the conversion effluent 20.

Turning back to FIG. 1, the remaining gas and vapor conversion products 24 from the solids separator 22 may be introduced into gas separation unit 26. In the gas separation unit 26, at least a portion of the pyrolysis oil vapors may be separated from the pyrolysis gas to thereby form a pyrolysis gas stream and a pyrolysis oil stream. Suitable systems to be used as the gas separation unit 26 may include, for example, a distillation column, a membrane separation unit, a filter, a quench tower, a condenser, or any other known separation unit known in the art. If necessary, after removal from the gas separation unit 26, the pyrolysis oil stream may be further quenched in a condenser in order to quench the pyrolysis vapors into their liquid form (i.e., the pyrolysis oil). The resulting pyrolysis oil stream and pyrolysis gas stream may be removed from the facility 10 and utilized in the other downstream applications described herein.

In one embodiment or in combination with any of the mentioned embodiments, the waste plastic source 12, feedstock pretreatment system 14, pyrolysis feed system 16, pyrolysis reactor 18, solids separator 22, and gas separation unit 26 may be in fluid communication between all units or some of the recited units. For example, the pyrolysis reactor 18 may be in fluid communication with the feedstock pretreatment system 14, the pyrolysis feed system 16, the solids separator 22, and the gas separation unit 26. Fluid communication can comprise jacketed piping, traced piping, and/or insulated piping.

In one embodiment or in combination with any of the mentioned embodiments, the pyrolysis reactor 18 is not in fluid communication with the waste plastic source 12.

Although not depicted in FIG. 1, the pyrolysis facility 10 depicted in FIG. 1 may be part of a chemical recycling facility. As used herein, a "chemical recycling facility" refers to a facility for producing a recycle content product via chemical recycling of waste plastic. A chemical recycling facility can employ one or more of the following steps: (i) preprocessing, (ii) solvolysis, (iii) pyrolysis, (iv) cracking, and/or (v) PDX gasification.

The pyrolysis system described herein may produce a pyrolysis oil, a pyrolysis gas, and a pyrolysis residue that may be directly used in various downstream applications based on their formulations. The various characteristics and properties of the pyrolysis oil, pyrolysis gas, and pyrolysis residue are described below. It should be noted that, while all of the following characteristics and properties may be listed separately, it is envisioned that each of the following characteristics and/or properties of the pyrolysis gas, pyrolysis oil, and/or pyrolysis residue are not mutually exclusive and may be combined and present in any combination.

In one embodiment or in combination with any of the mentioned embodiments, the pyrolysis oil may predominantly comprise hydrocarbons having from 4 to 30 carbon atoms per molecule (e.g., C4 to C30 hydrocarbons). As used herein, the term "Cx" or "Cx hydrocarbon," refers to a hydrocarbon compound including "x" total carbons per molecule, and encompasses all olefins, paraffins, aromatics, heterocyclic, and isomers having that number of carbon atoms. For example, each of normal, iso, and tert butane and butene and butadiene molecules would fall under the general description "C4."

In one embodiment or in combination with any of the mentioned embodiments, the pyrolysis oil may have a C4-C30 hydrocarbon content of at least 55, at least 60, at least 65, at least 70, at least 75, at least 80, at least 85, at least 90, or at least 95 weight percent based on the total weight of the pyrolysis oil.

In one embodiment or in combination with any of the mentioned embodiments, the pyrolysis oil can predominantly comprise C5 to C25 hydrocarbons, C5 to C22 hydrocarbons, or C5 to C20 hydrocarbons. For example, the pyrolysis oil may comprise at least 55, at least 60, at least 65, at least 70, at least 75, at least 80, at least 85, at least 90, or at least 95 weight percent of C5 to C25 hydrocarbons, C5 to C22 hydrocarbons, or C5 to C20 hydrocarbons, based on the total weight of the pyrolysis oil.

In one embodiment or in combination with any of the mentioned embodiments, the pyrolysis oil may have a C5-C12 hydrocarbon content of at least 5, at least 10, at least 15, at least 20, at least 25, at least 30, at least 35, at least 40, at least 45, at least 50, or at least 55 weight percent based on the total weight of the pyrolysis oil. Additionally, or alternatively, the pyrolysis oil may have a C5-C12 hydrocarbon content of not more than 95, not more than 90, not more than 85, not more than 80, not more than 75, not more than 70, not more than 65, not more than 60, not more than 55, or not more than 50 weight percent. The pyrolysis oil may have a C5-C12 hydrocarbon content in the range of 10 to 95 weight percent, 20 to 80 weight percent, or 35 to 80 weight percent.

In one embodiment or in combination with any of the mentioned embodiments, the pyrolysis oil may have a C13-C23 hydrocarbon content of at least 1, at least 5, at least 10, at least 15, at least 20, at least 25, or at least 30 weight percent based on the total weight of the pyrolysis oil. Additionally, or alternatively, the pyrolysis oil may have a C13-C23 hydrocarbon content of not more than 80, not more than 75, not more than 70, not more than 65, not more than 60, not more than 55, not more than 50, not more than 45, or not more than 40 weight percent. The pyrolysis oil may have a C13-C23 hydrocarbon content in the range of 1 to 80 weight percent, 5 to 65 weight percent, or 10 to 60 weight percent.

In one embodiment or in combination with any of the mentioned embodiments, the pyrolysis oil may have a C24+ hydrocarbon content of at least 1, at least 2, at least 3, at least 4, or at least 5 and/or not more than 15, not more than 10, not more than 9, not more than 8, not more than 7, or not more than 6 weight percent based on weight of the pyrolysis oil. The pyrolysis oil may have a C24+ hydrocarbon content in the range of 1 to 15 weight percent, 3 to 15 weight percent, or 5 to 10 weight percent.

In one embodiment or in combination with any of the mentioned embodiments, the two aliphatic hydrocarbons (branched or unbranched alkanes and alkenes, and alicyclics) having the highest concentration in the pyrolysis oil are in a range of C5-C18, C5-C16, C5-C14, C5-C10, or C5-C8, inclusive.

In one embodiment or in combination with any of the mentioned embodiments, the pyrolysis oil may also include various amounts of olefins and aromatics. The pyrolysis oil comprises at least 1, at least 5, at least 10, at least 15, at least 20, at least 25, at least 30, at least 35, or at least 40 weight percent of olefins and/or aromatics based on the total weight of the pyrolysis oil. Additionally, or alternatively, the pyrolysis oil may include not more than 90, not more than 80, not more than 70, not more than 60, not more than 50, not more than 45, not more than 40, not more than 35, not more than 30, not more than 25, not more than 20, not more than 15, not more than 10, not more than 5, or not more than 1 weight percent of olefins and/or aromatics.

In one embodiment or in combination with any of the mentioned embodiments, the pyrolysis oil may also include various amounts of olefins. The pyrolysis oil can comprise at least 1, at least 5, at least 10, at least 15, at least 20, at least 25, at least 30, at least 35, at least 40, at least 45, at least 50, at least 55, at least 60, or at least 65 weight percent of olefins based on the total weight of the pyrolysis oil. Additionally, or alternatively, the pyrolysis oil may include not more than 90, not more than 80, not more than 70, not more than 60, not more than 50, not more than 45, not more than 40, not more than 35, not more than 30, not more than 25, not more than 20, not more than 15, not more than 10, not more than 5, or not more than 1 weight percent of olefins.

In one embodiment or in combination with any of the mentioned embodiments, the pyrolysis oil may have an aromatic content of not more than 25, not more than 20, not more than 15, not more than 10, not more than 9, not more than 8, not more than 7, not more than 6, not more than 5, not more than 4, not more than 3, not more than 2, or not more than 1 weight percent based on the total weight of the pyrolysis oil. As used herein, the term "aromatics" refers to the total amount (in weight) of any compounds containing an aromatic moiety, such as benzene, toluene, xylene, and styrene.

In one embodiment or in combination with any of the mentioned embodiments, the pyrolysis oil may have a naphthene (e.g., cyclic aliphatic hydrocarbons) content of at least 1, at least 2, at least 3, at least 4, at least 5, at least 6, at least 7, at least 8, at least 9, at least 10, at least 11, at least 12, at least 13, at least 14, or at least 15 and/or not more than 50, not more than 45, not more than 40, not more than 35, not more than 30, not more than 25, or not more than 20 weight percent based on the total weight of the pyrolysis oil.

In one embodiment or in combination with any of the mentioned embodiments, the pyrolysis oil may have a paraffin (e.g., linear or branch alkanes) content of at least 5, at least 10, at least 15, at least 20, at least 25, at least 30, at least 35, at least 40, at least 45, at least 50, at least 55, at least 60, or at least 65 weight percent based on the total weight of the pyrolysis oil. Additionally or alternatively, the pyrolysis oil may have a paraffin content of not more than 99, not more than 97, not more than 95, not more than 93, not more than 90, not more than 85, not more than 80, not more than 75, not more than 70, not more than 65, not more than 60, not more than 55, not more than 50, not more than 45, not more than 40, not more than 35, or not more than 30 weight percent. The pyrolysis oil may have a paraffin content in the range of 25 to 90 weight percent, 35 to 90 weight percent, or 50 to 80 weight percent.

In one embodiment or in combination with any of the mentioned embodiments, the weight ratio of paraffin to naphthene can be at least 1:1, at least 1.5:1, at least 2:1, at least 2.2:1, at least 2.5:1, at least 2.7:1, at least 3:1, at least 3.3:1, at least 3.5:1, at least 3.75:1, at least 4:1, at least 4.25:1, at least 4.5:1, at least 4.75:1, at least 5:1, at least 6:1, at least 7:1, at least 8:1, at least 9:1, at least 10:1, at least 13:1, at least 15:1, or at least 17:1 based on the total weight of the pyrolysis oil.

In one embodiment or in combination with any of the mentioned embodiments, the weight ratio of paraffin and naphthene combined to aromatics can be at least 1:1, at least 1.5:1, at least 2:1, at least 2.5:1, at least 2.7:1, at least 3:1, at least 3.3:1, at least 3.5:1, at least 3.75:1, at least 4:1, at least 4.5:1, at least 5:1, at least 7:1, at least 10:1, at least 15:1, at least 20:1, at least 25:1, at least 30:1, at least 35:1, or at least 40:1 based on the total weight of the pyrolysis oil.

In one embodiment or in combination with any of the mentioned embodiments, the pyrolysis oil may have a combined paraffin and olefin content of at least 5, at least 10, at least 15, at least 20, at least 25, at least 30, at least 35, at least 40, or at least 45 and/or not more than 99, not more than 90, not more than 85, not more than 80, not more than 75, or not more than 70 weight percent based on the total weight of the pyrolysis oil. The pyrolysis oil may have a combined paraffin and olefin content in the range of 25 to 90 weight percent, 35 to 90 weight percent, or 50 to 80 weight percent.

In one embodiment or in combination with any of the mentioned embodiments, the pyrolysis oil can include oxygenated compounds or polymers in amount of at least 0.01, at least 0.1, at least 1, at least 2, or at least 5 and/or not more than 20, not more than 15, not more than 14, not more than 13, not more than 12, not more than 11, not more than 10, not more than 9, not more than 8, not more than 7, or not more than 6 weight percent based on the total weight of a pyrolysis oil. Oxygenated compounds and polymers are those containing an oxygen atom.

In one embodiment or in combination with any of the mentioned embodiments, the pyrolysis oil can include heteroatom compounds or polymers in amount of not more than 20, not more than 15, not more than 10, not more than 9, not more than 8, not more than 7, not more than 6, not more than 5, not more than 4, not more than 3, not more than 2, not more than 1, not more than 0.5, or not more than 0.1 weight percent based on the total weight of a pyrolysis oil. A heteroatom compound or polymer includes any compound or polymer containing nitrogen, sulfur, or phosphorus. Any other atom is not regarded as a heteroatom for purposes of determining the quantity of heteroatoms, heterocompounds, or heteropolymers present in the pyrolysis oil.

In one embodiment or in combination with any of the mentioned embodiments, the pyrolysis oil comprises not more than 5, not more than 4, not more than 3, not more than 2, not more than 1, or not more than 0.5 weight percent of water based on the total weight of the pyrolysis oil.

In one embodiment or in combination with any of the mentioned embodiments, the pyrolysis oil comprises less than 5, not more than 4, not more than 3, not more than 2, not more than 1, not more than 0.5, not more than 0.4, not more than 0.3, not more than 0.2, or not more than 0.1 weight percent of solids based on the total weight of the pyrolysis oil.

In one embodiment or in combination with any of the mentioned embodiments, the pyrolysis oil comprises at least 50, at least 55, at least 60, at least 65, at least 70, at least 75, at least 80, or at least 85 and/or not more than 99, not more than 95, not more than 90, not more than 85, not more than 80, not more than 75, not more than 70, not more than 65, or not more than 60 weight percent of atomic carbon based on the total weight of the pyrolysis oil.

In one embodiment or in combination with any of the mentioned embodiments, the pyrolysis oil comprises at least at least 5, at least 6, at least 7, at least 8, at least 9, or at least 10 and/or not more than 30, not more than 25, not more than 20, not more than 15, not more than 14, not more than 13, not more than 12, or not more than 11 weight percent of atomic hydrogen based on the total weight of the pyrolysis oil.

In one embodiment or in combination with any of the mentioned embodiments, the pyrolysis oil comprises not more than 10, not more than 9, not more than 8, not more than 7, not more than 6, not more than 5, not more than 4, not more than 3, not more than 2, not more than 1, or not more than 0.5 weight percent of atomic oxygen based on the total weight of the pyrolysis oil.

In one embodiment or in combination with any of the mentioned embodiments, the pyrolysis oil comprises less than 1,000, not more than 500, not more than 400, not more than 300, not more than 200, not more than 100, or not more than 50 ppm of atomic sulfur based on the total weight of the pyrolysis oil.

In one embodiment or in combination with any of the mentioned embodiments, the pyrolysis oil comprises less than 1,000, not more than 500, not more than 400, not more than 300, not more than 200, not more than 100, or not more than 50 ppm of metals based on the total weight of the pyrolysis oil.

In one embodiment or in combination with any of the mentioned embodiments, the pyrolysis oil comprises less than 1,000, not more than 500, not more than 400, not more than 300, not more than 200, not more than 100, or not more than 50 ppm of metals based on the total weight of the pyrolysis oil.

In one embodiment or in combination with any of the mentioned embodiments, the pyrolysis oil comprises less than 1,000, not more than 500, not more than 400, not more than 300, not more than 200, not more than 100, or not more than 50 ppm of alkali metals and/or alkaline earth metals based on the total weight of the pyrolysis oil.

It should be noted that all of the disclosed hydrocarbon weight percentages may be determined using gas chromatography-mass spectrometry (GC-MS).

In one embodiment or in combination with any of the mentioned embodiments, the pyrolysis oil may exhibit a density at 15° C. of at least 0.6, at least 0.65, or at least 0.7 and/or not more than 1, not more than 0.95, not more than 0.9, or not more than 0.9 g/cm$^3$. In one embodiment or in combination with any of the mentioned embodiments, the pyrolysis oil exhibits a density at 15° C. at a range of 0.6 to 1 g/cm$^3$, 0.65 to 0.95 g/cm$^3$, or 0.7 to 0.9 g/cm$^3$.

In one embodiment or in combination with any of the mentioned embodiments, the pyrolysis oil may exhibit an API gravity at 15° C. of at least 28, at least 29, at least 30, at least 31, at least 32, or at least 33 and/or not more than 50, not more than 49, not more than 48, not more than 47, not more than 46, or not more than 45. The pyrolysis oil exhibits an API gravity at 15° C. at a range of 28 to 50, 29 to 58, or 30 to 44.

In one embodiment or in combination with any of the mentioned embodiments, the pyrolysis oil may have a mid-boiling point of at least 75° C., at least 80° C., at least 85° C., at least 90° C., at least 95° C., at least 100° C., at least 105° C., at least 110° C., or at least 115° C. and/or not more than 250° C., not more than 245° C., not more than 240° C., not more than 235° C., not more than 230° C., not more than 225° C., not more than 220° C., not more than 215° C., not more than 210° C., not more than 205° C., not more than 200° C., not more than 195° C., not more than 190° C., not more than 185° C., not more than 180° C., not more than 175° C., not more than 170° C., not more than 165° C., not more than 160° C., not more than 155° C., not more than 150° C., not more than 145° C., not more than 140° C., not more than 135° C., not more than 130° C., not more than 125° C., or not more than 120° C., as measured according to ASTM D-5399. The pyrolysis oil may have a mid-boiling point in the range of 75 to 250° C., 90 to 225° C., or 115 to 190° C. As used herein, "mid-boiling point" refers to the median boiling point temperature of the pyrolysis oil, where 50 percent by volume of the pyrolysis oil boils above the mid-boiling point and 50 percent by volume boils below the mid-boiling point.

In one embodiment or in combination with any of the mentioned embodiments, the boiling point range of the pyrolysis oil may be such that not more than 10 percent of the pyrolysis oil has a final boiling point (FBP) of at least 250° C., at least 280° C., at least 290° C., at least 300° C., or at least 310° C., as measured according to ASTM D-5399.

Turning to the pyrolysis gas, the pyrolysis gas can have a methane content of at least 1, at least 2, at least 3, at least 4, at least 5, at least 6, at least 7, at least 8, at least 9, at least 10, at least 11, at least 12, at least 13, at least 14, or at least 15 and/or not more than 50, not more than 45, not more than 40, not more than 35, not more than 30, not more than 25, or not more than 20 weight percent based on the total weight of the pyrolysis gas. The pyrolysis gas can have a methane content in the range of 1 to 50 weight percent, 5 to 50 weight percent, or 15 to 45 weight percent.

In one embodiment or in combination with any of the mentioned embodiments, the pyrolysis gas can have a C3 hydrocarbon content of at least 1, at least 2, at least 3, at least 4, at least 5, at least 6, at least 7, at least 8, at least 9, at least 10, at least 15, at least 20, or at least 25 and/or not more than 50, not more than 45, not more than 40, not more than 35, or not more than 30 weight percent based on the total weight of the pyrolysis gas. The pyrolysis gas can have a C3 hydrocarbon content in the range of 1 to 50 weight percent, 5 to 50 weight percent, or 20 to 50 weight percent.

In one embodiment or in combination with any of the mentioned embodiments, the pyrolysis gas can have a C4 hydrocarbon content of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 25 and/or not more than 50, not more than 45, not more than 40, not more than 35, or not more than 30 weight percent based on the total weight of the pyrolysis gas. The pyrolysis gas can have a C4 hydrocarbon content in the range of 1 to 50 weight percent, 5 to 50 weight percent, or 20 to 50 weight percent.

In one embodiment or in combination with any of the mentioned embodiments, the pyrolysis gas can have a combined C3 and C4 hydrocarbon content (including all hydrocarbons having carbon chain lengths of C3 or C4) of at least 5, at least 10, at least 15, at least 20, at least 25, at least 30, at least 35, at least 40, at least 45, at least 50, at least 55, or at least 60 and/or not more than 99, not more than 95, not more than 90, not more than 85, not more than 80, not more than 75, not more than 70, or not more than 65 weight percent based on the total weight of the pyrolysis gas. The pyrolysis gas can have a combined C3/C4 hydrocarbon content in the range of 10 to 90 weight percent, 25 to 90 weight percent, or 25 to 80 weight percent.

In one embodiment or in combination with any of the mentioned embodiments, the pyrolysis gas comprises a sulfur content of at least 1, at least 2, at least 3, at least 4, at least 5, at least 6, at least 7, at least 8, at least 9, at least 10, at least 11, at least 12, at least 13, at least 14, or at least 15 and/or not more than 1,000, not more than 500, not more than 400, not more than 300, not more than 200, or not more than 100 ppm.

Although not wishing to be bound by theory, it is believed that the production of C3 and C4 hydrocarbons may be facilitated by higher pyrolysis temperatures (e.g., those exceeding 550° C.), the selection of specific catalyst types, or the absence of specific catalysts (e.g., ZSM-5).

Turning to the pyrolysis residue, in one embodiment or in combination with any of the mentioned embodiments, the pyrolysis residue comprises at least 20, at least 25, at least 30, at least 35, at least 40, at least 45, at least 50, at least 55, at least 60, at least 65, at least 70, at least 75, at least 80, or at least 85 weight percent of C20+ hydrocarbons based on the total weight of the pyrolysis residue. As used herein, "C20+ hydrocarbon" refers to hydrocarbon compounds containing at least 20 total carbons per molecule, and encompasses all olefins, paraffins, and isomers having that number of carbon atoms.

In one embodiment or in combination with any of the mentioned embodiments, the pyrolysis residue comprises not more than 15, not more than 14, not more than 13, not more than 12, not more than 11, not more than 10, not more than 9, not more than 8, not more than 7, not more than 6, not more than 5, not more than 4, not more than 3, not more than 2, not more than 1, or not more than 0.5 weight percent of water based on the total weight of the pyrolysis residue.

In one embodiment or in combination with any of the mentioned embodiments, the pyrolysis residue comprises at least 1, at least 2, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 weight percent of carbon-containing solids based on the total weight of the pyrolysis residue. Additionally, or alternatively, the pyrolysis residue comprises not more than 99, not more than 90, not more than 80, not more than 70, not more than 60, not more than 50, not more than 40, not more than 30, not more than 20, not more than 10, not more than 9, not more than 8, not more than 7, not more than 6, not more than 5, or not more than 4 weight percent of carbon-containing solids. As used herein, "carbon-containing solids" refer to carbon-containing compositions that are derived from pyrolysis and are solid at 25° C. and 1 atm. the carbon-containing solids can comprise at least 20, at least 30, at least 40, at least 50, at least 60, at least 70, at least 80, or at least 90 weight percent of carbon based on the total weight of the carbon-containing solids.

In one embodiment or in combination with any of the mentioned embodiments, the pyrolysis residue comprises a C:H atomic ratio that is greater than or equal to paraffins or greater than or equal to 0.25:1, 0.3:1, 0.35:1, 0.4:1, or 0.45:1.

In one embodiment or in combination with any of the mentioned embodiments, the separated pyrolysis residue comprises not more than 40, not more than 30, not more than 20, not more than 10, not more than 5, not more than 4, not more than 3, not more than 2, or not more than 1 weight percent of pyrolysis oil based on the total weight of the pyrolysis residue.

Figure 2:
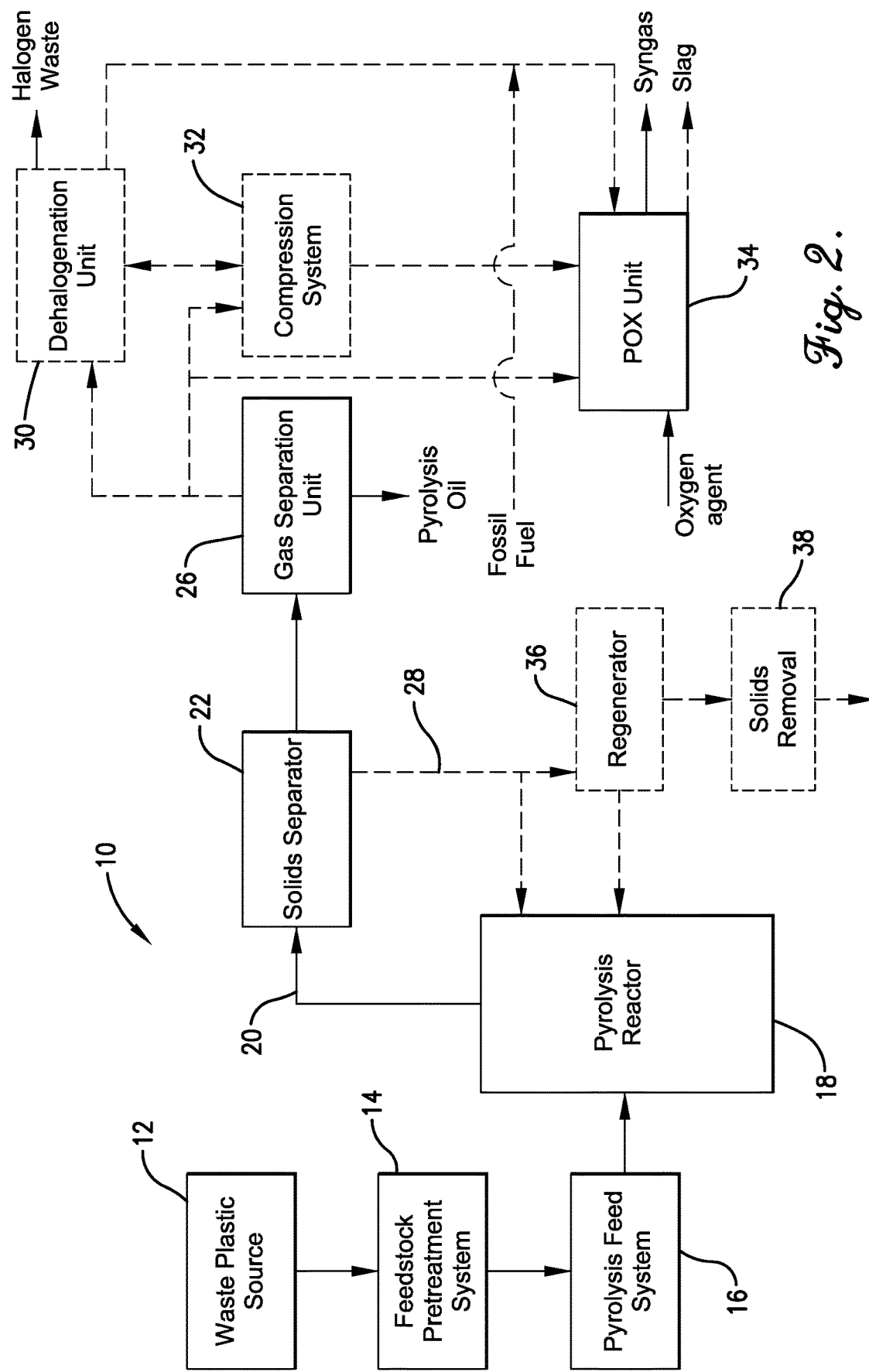
FIG. 2 depicts another exemplary system that may at least partially convert one or more waste plastics into various useful pyrolysis-derived products.

FIG. 2 depicts another exemplary system 10 that may be employed to at least partially convert one or more waste plastics, particularly recycled plastic waste, into various useful pyrolysis-derived products. It should be understood that the system shown in FIG. 2 is just one example of a system within which the present disclosure can be embodied. The present disclosure may find application in a wide variety of other systems where it is desirable to efficiently and effectively convert pyrolysis products into various desirable end products. Furthermore, the components or units depicted with dashed lines represents optional streams and/or components that may be found in the exemplary system 10. Thus, there are envisioned embodiments where the components in dashed lines may or may not be present. The exemplary system illustrated in FIG. 2 will now be described in greater detail.

The pyrolysis facility 10 as shown in FIG. 2 comprises a waste plastic source 12, a feedstock pretreatment system 14, a pyrolysis feed system 16, a pyrolysis reactor 18, a solids separator 22, and a gas separation unit 26 that function in the same manner as the components described above in regard to FIG. 1. FIG. 2 demonstrates an embodiment wherein a partial oxidation (PDX) gasification facility is incorporated into the overall system. As used herein, "partial oxidation (PDX) gasification facility" or "PDX facility" refers to a facility that includes all equipment, lines, and controls necessary to carry out PDX gasification of waste plastic. For example, the gasification facility may comprise a gasifier, a gasifier feed injector, a gasifier ball mill, a feed spray unit, and/or a solidification tank. As shown in FIG. 2, at least a portion of the pyrolysis gas stream from the gas separation unit 26 may be introduced into a dehalogenation unit 30, a compressions system 32, and/or a partial oxidation (PDX) unit 34.

In one embodiment or in combination with any of the mentioned embodiments, at least a portion of the pyrolysis gas from the gas separation unit 26 may be compressed in a compressions system 32 to form a compressed pyrolysis gas. The compressions system 32 may comprise any compressions system known in the art and may comprise a gas compressor having between 1 and 10, 2 and 8, or 2 and 6 compression stages, each with optional inter-stage cooling and liquid removal. In one embodiment or in combination with any of the mentioned embodiments, the pressure of the compressed pyrolysis gas stream at the outlet of the compression system 32 may be in the range of from 7 to 50 bar gauge, 8.5 to 40 psig, or 9.5 to 30 barg.

In one embodiment or in combination with any of the mentioned embodiments, the suction pressure of the compression system can be at least 0.01, at least 0.05, or at least 0.1 barg and/or not more than 1.1, not more than 0.95, not more than 0.90, or not more than 0.85 barg, while the outlet of the first compression stage can be at least 1.3, at least 1.4, at least 1.5, or at least 1.6 barg and/or not more than 4, not more than 3.75, not more than 3.5, not more than 3.25, not more than 3, not more than 2.9, not more than 2.8 or not more than 2.7 barg.

The outlet of the second compression stage can be at least 3.8, at least 3.9, at least 4, at least 4.5, at least 5, or at least 5.5 barg and/or not more than 11, not more than 10.5, not more than 10, not more than 9, not more than 8.5, not more than 8, not more than 7, not more than 6.5, not more than 6.4, or not more than 6.3 barg, while the outlet of the third compression stage can be at least 8.7, at least 8.8, at least 8.9, at least 9, at least 10, at least 12, or at least 14 barg and/or not more than 30, not more than 27, not more than 25, not more than 20, not more than 15, not more than 13.5, not more than 13.4, or not more than 13.25 barg. The outlet of the fourth compression stage can be at least 14.2, at least 14.3, or a. 14.4 barg, and/or not more than 23.5, not more than 23.4, not more than 23.3, or not more than 23.2 barg. The outlet of the fifth compression stage, when present, can be at least 27.5, at least 27.7, or at least 27.9 barg and/or not more than 46, not more than 45.5, not more than 45.2 barg. When no fifth compression stage is present, the outlet pressure of the fourth compression stage can be at least 30, at least 32, at least 35, at least 37, or at least 40 barg and/or not more than 65, not more than 60, or not more than 57 barg.

The suction pressure of the first stage can be in the range of from 0.1 to 0.8 barg and the outlet pressure of the first stage can be from 1.6 to 2.7 barg. The outlet pressure of the second stage can be from 4 to 6 barg, while the outlet pressure of the third stage can be from 9 to 13 barg. The fourth stage can have an outlet pressure of 14 to 23 barg, and the fifth stage (when present) can have an outlet pressure of 28 to 45 barg. The suction pressure of the first stage can be in the range of from 0.1 to 1 barg, the outlet pressure of the first stage can be in the range of from 1.5 to 3.75 barg, and the outlet pressure of the second stage can be in the range of from 14.5 to 27 barg. The outlet pressure of the fourth stage, particularly when, for example, the fourth stage is the last stage, can be in the range of from 30 to 60 barg.

In one embodiment or in combination with any of the mentioned embodiments, the compression system 32 may remove at least a portion of residual pyrolysis oil that may be present in the pyrolysis gas in the form of condensed residual pyrolysis oil.

In one embodiment or in combination with any of the mentioned embodiments, at least a portion of this removed residual pyrolysis oil may be introduced back into the pyrolysis reactor and/or a cracking unit, such as a naphtha cracker.

Additionally, or alternatively, in one embodiment or in combination with any of the mentioned embodiments, at least a portion of the removed residual pyrolysis oil may be combined with the pyrolysis oil stream from the gas separation unit 26.

Additionally, or alternatively, in one embodiment or in combination with any of the mentioned embodiments, at least a portion of the pyrolysis gas from the gas separation unit 26 and/or at least a portion of the compressed pyrolysis gas from the compression system 32 may be introduced into the dehalogenation unit 30. While in the dehalogenation unit 30, at least a portion of the halogens in the pyrolysis gas may be removed to thereby form a dehalogenated pyrolysis gas and a halogen-containing waste stream. The halogen-containing waste stream (e.g., chlorine-containing compounds such as HCl) may be in the form of gas and may be discarded from the pyrolysis system. The dehalogenation unit 30 may comprise a distillation column, a wiped film reactor, a halogen scavenger vessel, or a combination thereof.

In one embodiment or in combination with any of the mentioned embodiments, the dehalogenation unit 30 can comprise a halogen scavenger that can absorb at least a portion of the gaseous halogen-containing byproducts. The halogen scavenger may comprise a metal oxide, a metal hydroxide, a carbon composite, or a combination thereof. For example, the halogen scavenger may comprise a porous alumina, a modified porous alumina, a slaked lime, a calcium carbonate, or combinations thereof.

Generally, in one embodiment or in combination with any of the mentioned embodiments, the halogens removed by the dehalogenation unit 30 comprise the covalently-bonded halogen atoms originally present in the polymer backbone of the waste plastics used to as the pyrolysis feedstock to produce the pyrolysis gas. The dehalogenation unit 30 may remove at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 percent of the covalently-bonded halogen atoms from the pyrolysis gas.

In one embodiment or in combination with any of the mentioned embodiments, the dehalogenated pyrolysis gas may comprise a halogen content of less than 500, not more than 400, not more than 300, not more than 250, not more than 200, not more than 150, not more than 100, not more than 90, not more than 80, not more than 70, not more than 60, not more than 50, not more than 40, not more than 30, not more than 20, not more than 10, or not more than 5 ppm.

Alternatively, in one embodiment or in combination with any of the mentioned embodiments, at least a portion of the pyrolysis gas may be first introduced into the dehalogenation unit 30 and at least a portion of the resulting dehalogenated gas may be introduced into the compression system 32 to form the compressed pyrolysis gas.

Turning back to FIG. 2, at least a portion of the pyrolysis gas from the gas separation 26, at least a portion of the dehalogenated pyrolysis gas from the dehalogenation unit 30, and/or at least a portion of the compressed pyrolysis gas from the compression system 32 may be introduced into a gasifier, such as a partial oxidation (PDX) unit 34. While in the partial oxidation unit 34, at least a portion of the pyrolysis gas may be subjected to partial oxidation (PDX) gasification. As used herein, "partial oxidation (PDX) gasification" or "PDX" refers to the high temperature conversion of a hydrocarbon-containing feed into syngas (carbon monoxide, hydrogen, and carbon dioxide), where the conversion is carried out with an amount of oxygen that is less than the stoichiometric amount of oxygen needed for complete oxidation of carbon to CO2. The feed to PDX gasification can include solids, liquids, and/or gasses.

In one embodiment or in combination with any of the mentioned embodiments, the PDX gasification unit may comprise a gas-fed gasifier, a liquid-fed gasifier, a solid-fed gasifier, or a combination thereof. More particularly, the PDX gasification unit may conduct liquid-fed PDX gasification. As used herein, "liquid-fed PDX gasification" refers to a PDX gasification process where the feed to the process comprises predominately components that are liquid at 25° C. and 1 atm. Additionally, or alternatively, the PDX gasification unit may conduct gas-fed PDX gasification. As used herein, "gas-fed PDX gasification" refers to a PDX gasification process where the feed to the process comprises predominately components that are gaseous at 25° C. and 1 atm.

As shown in FIG. 2, a process is provided for the production of recycle content syngas, wherein the process comprises: (a) charging an oxygen agent and a feedstock composition comprising a pyrolysis gas to a gasification zone within a gasifier; (b) gasifying the feedstock composition together with the oxygen agent in a gasification zone to thereby produce a syngas composition; and (c) discharging at least a portion of the syngas composition from the gasifier. As shown in FIG. 2, a fossil fuel (e.g., natural gas, coal, petroleum coke, biomass, and combinations thereof) may be combined with the pyrolysis gas from the gas separation 26, dehalogenation unit 30, and/or compression system 32 to produce the gasification feedstock.

In one embodiment or in combination with any of the mentioned embodiments, the gasification feedstock comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 and/or not more than 90, not more than 85, not more than 80, not more than 75, not more than 70, not more than 65, not more than 60, not more than 55, not more than 50, not more than 40, not more than 35, or not more than 30 weight percent of the pyrolysis gas, which can be derived from the gas separation 26, dehalogenation unit 30, and/or compression system 32.

More particularly, the gasification feedstock comprises 1 to 75, 1 to 50, 1 to 40, or 1 to 30 weight percent of the pyrolysis gas, which can be derived from the gas separation 26, dehalogenation unit 30, and/or compression system 32, based on the total weight of the gasification feedstock.

As noted above, the gasification feedstock may also comprise a fossil fuel, such as a coal or PET-coke or natural gas or liquid hydrocarbons such as heavy oil. In one embodiment or in combination with any of the mentioned embodiments, the gasification feedstock may comprise at least 1, at least 10, at least 15, at least 20, at least 25, at least 30, at least 35, at least 40, at least 45, at least 50, at least 55, at least 60, at least 65, at least 70, at least 75, at least 80, or at least 85 and/or not more than 99, not more than 95, or not more than 90 weight percent of a fossil fuel, such as natural gas, based on the total weight of the gasification feedstock. More particularly, the gasification feedstock comprises 10 to 99, 40 to 99, or 75 to 99 weight percent of a fossil fuel, such as natural gas.

The gasification feedstock stream is desirably injected along with the oxygen agent into a refractory-lined combustion chamber of the synthesis gas generating gasifier. In one embodiment or in combination with any of the mentioned embodiments, the feedstock stream and the oxygen agent are sprayed through an injector into a gasification zone that is under significant pressure, typically at least 500, at least 600, at least 800, at least 1000, or at least 1250 psig. Generally, the velocity or flow rate of the feedstock and oxygen agent streams ejected from the injector nozzle into the combustion chamber will exceed the rate of flame propagation to avoid backflash.

In one embodiment or in combination with any of the mentioned embodiments, the oxygen agent comprises an oxidizing gas that can include air. More particularly, the oxygen agent comprises a gas enriched in oxygen at quantities greater than that found in air. In one embodiment or in combination with any of the mentioned embodiments, the oxygen agent comprises at least 25, at least 35, at least 40, at least 50, at least 60, at least 70, at least 80, at least 90, at least 95, at least 97, at least 99, or at least 99.5 mole percent of oxygen based on all moles in the oxygen agent stream injected into the reaction (combustion) zone of the gasifier. The particular amount of oxygen as supplied to the reaction zone is desirably sufficient to obtain near or maximum yields of carbon monoxide and hydrogen obtained from the gasification reaction relative to the components in the feedstock stream, considering the amount relative to the feedstock stream, and the amount of feedstock charged, the process conditions, and the reactor design In one embodiment or in combination with any of the mentioned embodiments, steam is not supplied to the gasification zone. Alternatively, or in addition, steam may be supplied to the gasification zone.

Other reducible oxygen-containing gases in addition to the oxygen agent may be supplied to the reaction zone, for example, carbon dioxide, nitrogen, or simply air. In one embodiment or in combination with any of the mentioned embodiments, no gas stream enriched in carbon dioxide or nitrogen (e.g., greater than the molar quantity found in air, or at least 2, at least 5, at least 10, or at least 40 mole percent) is charged to the gasifier. These gases may serve as carrier gases to propel a feedstock to a gasification zone. Due to the pressure within the gasification zone, these carrier gases may be compressed to provide the motive force for introduction into the gasification zone.

In one embodiment or in combination with any of the mentioned embodiments, no gas stream containing more than 0.01 or 0.02 mole percent of carbon dioxide is charged to the gasifier or gasification zone. Additionally, or alternatively, no gas stream containing more than 77, 70, 50, 30, 10, 5, or 3 mole percent nitrogen is charged to the gasifier or gasification zone. Furthermore, a gaseous hydrogen stream more than 0.1, 0.5, 1, or 5 mole percent hydrogen may not be charged to the gasifier or to the gasification zone. Moreover, a stream of methane gas containing more than 0.1, 0.5, 1, or 5 mole percent methane may not be charged to the gasifier or to the gasification zone. In certain embodiments, the only gaseous stream introduced to the gasification zone is the oxygen agent, which is an oxygen-rich gas stream as described above.

The gasification process desirably employed is a partial oxidation gasification reaction, which was described above. Generally, to enhance the production of hydrogen and carbon monoxide, the oxidation process involves partial, rather than complete, oxidization of the gasification feedstock and, therefore, may be operated in an oxygen-lean environment, relative to the amount needed to completely oxidize 100 percent of the carbon and hydrogen bonds. In one embodiment or in combination with any of the mentioned embodiments, the total oxygen requirements for the gasifier may be at least 5, at least 10, at least 15, or at least 20 percent in excess of the amount theoretically required to convert the carbon content of the gasification feedstock to carbon monoxide. In general, satisfactory operation may be obtained with a total oxygen supply of 10 to 80 percent in excess of the theoretical requirements. For example, examples of suitable amounts of oxygen per pound of carbon may be in the range of 0.4 to 3.0, 0.6 to 2.5, 0.9 to 2.5, or 1.2 to 2.5 pounds free oxygen per pound of carbon.

Mixing of the feedstock stream and the oxygen agent may be accomplished entirely within the reaction zone by introducing the separate streams of feedstock and oxygen agent so that they impinge upon each other within the reaction zone. In one embodiment or in combination with any of the mentioned embodiments, the oxygen agent stream is introduced into the reaction zone of the gasifier as high velocity to both exceed the rate of flame propagation and to improve mixing with the feedstock stream. The oxidant may be injected into the gasification zone in the range of 25 to 500, 50 to 400, or 100 to 400 feet per second. These values would be the velocity of the gaseous oxygen agent stream at the injector-gasification zone interface, or the injector tip velocity.

In one embodiment or in combination with any of the mentioned embodiments, the gasification feedstock stream and the oxygen agent can optionally be preheated to a temperature of at least 200° C., at least 300° C., or at least 400° C. However, the gasification process employed does not require preheating the feedstock stream to efficiently gasify the feedstock and a preheat treatment step may result in lowering the energy efficiency of the process.

In one embodiment or in combination with any of the mentioned embodiments, the type of gasification technology employed is a partial oxidation entrained flow gasifier that generates syngas. This technology is distinct from fixed bed (alternatively called moving bed) gasifiers and from fluidized bed gasifiers. In fixed bed (or moving bed gasifiers), the feedstock stream moves in a countercurrent flow with the oxidant gas, and the oxidant gas typically employed is air. The feedstock stream falls into the gasification chamber, accumulates, and forms a bed of feedstock.

Air (or alternatively oxygen) flows from the bottom of the gasifier up through the bed of feedstock material continuously while fresh feedstock continuously falls down from the top by gravity to refresh the bed as it is being combusted. The combustion temperatures are typically below the fusion temperature of the ash and are non-slagging. Whether the fixed bed operated in countercurrent flow or in some instances in co-current flow, the fixed bed reaction process generates high amount of tars, oils, and methane produced by pyrolysis of the feedstock in the bed, thereby both contaminating the syngas produced and the gasifier.

The contaminated syngas requires significant effort and cost to remove tarry residues that would condense once the syngas is cooled, and because of this, such syngas streams are generally not used to make chemicals and are instead used in direct heating applications. In a fluidized bed, the feedstock material in the gasification zone is fluidized by action of the oxidant flowing through the bed at a high enough velocity to fluidize the particles in the bed. In a fluidized bed, the homogeneous reaction temperatures and low reaction temperatures in the gasification zone also promotes the production of high amounts of unreacted feedstock material and low carbon conversion, and operating temperatures in the fluidized bed are typically between 800-1000° C. Further, in a fluidized bed it is important to operate below slagging conditions to maintain the fluidization of the feedstock particles which would otherwise stick to the slag and agglomerate. By employing an entrained flow gasification, these deficiencies present with fixed (or moving bed) and fluidized bed gasifiers that are typically used to process waste materials is overcome.

An exemplary gasifier that may be used in depicted in U.S. Pat. No. 3,544,291, the entire disclosure of which is incorporated herein by reference in its entirety.

In one embodiment or in combination with any of the mentioned embodiments, the gasifier is non-catalytic, meaning that the gasifier does not contain a catalyst bed and the gasification process is non-catalytic, meaning that a catalyst is not introduced into the gasification zone as a discrete unbound catalyst. Furthermore, the gasification process can also be a slagging gasification process; that is, operated under slagging conditions (well above the fusion temperature of ash) such that a molten slag is formed in the gasification zone and runs along and down the refractory walls.

In one embodiment or in combination with any of the mentioned embodiments, the gasification zone, and optionally all reaction zones in the gasifier, are operated at a temperature of at least 1000° C., at least 1100° C., at least 1200° C., at least 1250° C., or at least 1300° C. and/or not more than 2500° C., not more than 2000° C., not more than 1800° C., or not more than 1600° C. The reaction temperature can be autogenous. Advantageously, the gasifier operating in steady state mode can be at an autogenous temperature and does not require application of external energy sources to heat the gasification zone.

In one embodiment or in combination with any of the mentioned embodiments, the gasifier is a predominately gas fed gasifier.

In one embodiment or in combination with any of the mentioned embodiments, the gasifier is a non-slagging gasifier or operated under conditions not to form a slag.

In one embodiment or in combination with any of the mentioned embodiments, the gasifier is not under negative pressure during operations, but rather is under positive pressure during operation.

In one embodiment or in combination with any of the mentioned embodiments, the gasifier is operated at a pressure within the gasification zone (or combustion chamber) of at least 200 psig (1.38 MPa), at least 300 psig (2.06 MPa), at least 350 psig (2.41 MPa), at least 400 psig (2.76 MPa), at least 420 psig (2.89 MPa), at least 450 psig (3.10 MPa), at least 475 psig (3.27 MPa), at least 500 psig (3.44 MPa), at least 550 psig (3.79 MPa), at least 600 psig (4.13 MPa), at least 650 psig (4.48 MPa), at least 700 psig (4.82 MPa), at least 750 psig (5.17 MPa), at least 800 psig (5.51 MPa), at least 900 psig (6.2 MPa), at least 1000 psig (6.89 MPa), at least 1100 psig (7.58 MPa), or at least 1200 psig (8.2 MPa).

Additionally or alternatively, the gasifier can be operated at a pressure within the gasification zone (or combustion chamber) of not more than 1300 psig (8.96 MPa), not more than 1250 psig (8.61 MPa), not more than 1200 psig (8.27 MPa), not more than 1150 psig (7.92 MPa), not more than 1100 psig (7.58 MPa), or not more than 1050 psig (7.23 MPa), not more than 1000 psig (6.89 MPa), not more than 900 psig (6.2 MPa), not more than 800 psig (5.51 MPa), or not more than 750 psig (5.17 MPa).

Examples of suitable pressure ranges include 400 to 1000, 425 to 900, 450 to 900, 475 to 900, 500 to 900, 550 to 900, 600 to 900, 650 to 900, 400 to 800, 425 to 800, 450 to 800, 475 to 800, 500 to 800, 550 to 800, 600 to 800, 650 to 800, 400 to 750, 425 to 750, 450 to 750, 475 to 750, 500 to 750, or 550 to 750 psig.

Generally, the average residence time of gases in the gasifier reactor can be very short to increase throughput. Since the gasifier may be operated at high temperature and pressure, substantially complete conversion of the feedstock to gases can occur in a very short time frame. In one embodiment or in combination with any of the mentioned embodiments, the average residence time of the gases in the gasifier can be not more than 30, not more than 25, not more than 20, not more than 15, not more than 10, or not more than 7 seconds.

To avoid fouling downstream equipment from the gasifier (scrubbers, $CO/H_2$ shift reactors, acid gas removal, chemical synthesis), and the piping in-between, the resulting syngas may have a low or no tar content. In one embodiment or in combination with any of the mentioned embodiments, the syngas stream discharged from the gasifier may comprise not more than 4, not more than 3, not more than 2, not more than 1, not more than 0.5, not more than 0.2, not more than 0.1, or not more than 0.01 weight percent of tar based on the weight of all condensable solids in the syngas stream. For purposes of measurement, condensable solids are those compounds and elements that condense at a temperature of 15° C. and 1 atm. Examples of tar products include naphthalenes, cresols, xylenols, anthracenes, phenanthrenes, phenols, benzene, toluene, pyridine, catechols, biphenyls, benzofurans, benzaldehydes, acenaphthylenes, fluorenes, naphthofurans, benzanthracenes, pyrenes, acephenanthrylenes, benzopyrenes, and other high molecular weight aromatic polynuclear compounds. The tar content can be determined by GC-MSD.

Generally, the raw syngas stream discharged from the gasification vessel includes such gases as hydrogen, carbon monoxide, and carbon dioxide and can include other gases such as methane, hydrogen sulfide, and nitrogen depending on the fuel source and reaction conditions.

In one embodiment or in combination with any of the mentioned embodiments, the raw syngas stream (the stream discharged from the gasifier and before any further treatment by way of scrubbing, shift, or acid gas removal) can have the following composition in mole percent on a dry basis and based on the moles of all gases (elements or compounds in gaseous state at 25° C. and 1 atm) in the raw syngas stream:
 a hydrogen content in the range of 15 to 60, 18 to 50, 18 to 45, 18 to 40, 23 to 40, 25 to 40, 23 to 38, 29 to 40, 31 to 40 mole percent;
 a carbon monoxide content of 20 to 75, 20 to 65, 30 to 70, 35 to 68, 40 to 68, 40 to 60, 35 to 55, or 40 to 52 mole percent;
 a carbon dioxide content of 1.0 to 30, 2 to 25, 2 to 21, 10 to 25, or 10 to 20 mole percent;
 a water content of 2.0 to 40, 5 to 35, 5 to 30, or 10 to 30 mole percent;
 a methane content of 0.0 to 30, 0.01 to 15, 0.01 to 10, 0.01 to 8, 0.01 to 7, 0.01 to 5, 0.01 to 3, 0.1 to 1.5, or 0.1 to 1 mole percent;
 a $H_2S$ content of 0.01 to 2.0, 0.05 to 1.5, 0.1 to 1, or 0.1 to 0.5 mole percent;
 a COS content of 0.05 to 1.0, 0.05 to 0.7, or 0.05 to 0.3 mole percent;
 a sulfur content of 0.015 to 3.0, 0.02 to 2, 0.05 to 1.5, or 0.1 to 1 mole percent; and/or
 a nitrogen content of 0.0 to 5, 0.005 to 3, 0.01 to 2, 0.005 to 1, 0.005 to 0.5, or 0.005 to 0.3 mole percent.

In one embodiment or in combination with any of the mentioned embodiments, the syngas comprises a molar hydrogen/carbon monoxide ratio of at least 0.65, at least 0.68, at least 0.7, at least 0.73, at least 0.75, at least 0.78, at least 0.8, at least 0.85, at least 0.88, at least 0.9, at least 0.93, at least 0.95, at least 0.98, or at least 1.

The gas components can be determined by FID-GC and TCD-GC or any other method recognized for analyzing the components of a gas stream.

Turning back to FIG. 2, at least a portion of the pyrolysis residue 28 from the solids separator 22 may be introduced into an optional regenerator 30 for regeneration, generally by combustion. After regeneration, at least a portion of the hot regenerated solids can be reintroduced directly into the pyrolysis reactor 18. Additionally, or alternatively, at least a portion of the solid particles recovered in the solids separator 22 may be directly introduced back into the pyrolysis reactor 18, especially if the solid residue contains a notable amount of unconverted plastic waste. Furthermore, residual solids can be removed from the regenerator 26 via a solids removal unit 32 and bled out of the system.

In one embodiment or in combination with any of the mentioned embodiments, the waste plastic source 12, feedstock pretreatment system 14, pyrolysis feed system 16, pyrolysis reactor 18, solids separator 22, gas separation unit 26, dehalogenation unit 30, compression system 32, and PDX unit 34 may be in fluid communication between all units or some of the recited units. For example, the pyrolysis reactor 18 may be in fluid communication with the PDX unit 34. In one embodiment or in combination with any of the mentioned embodiments, fluid communication comprises jacketed piping, traced piping, and/or insulated piping.

In one embodiment or in combination with any of the mentioned embodiments, the pyrolysis reactor 18 is not in fluid communication with the PDX unit 34.

Figure 3:
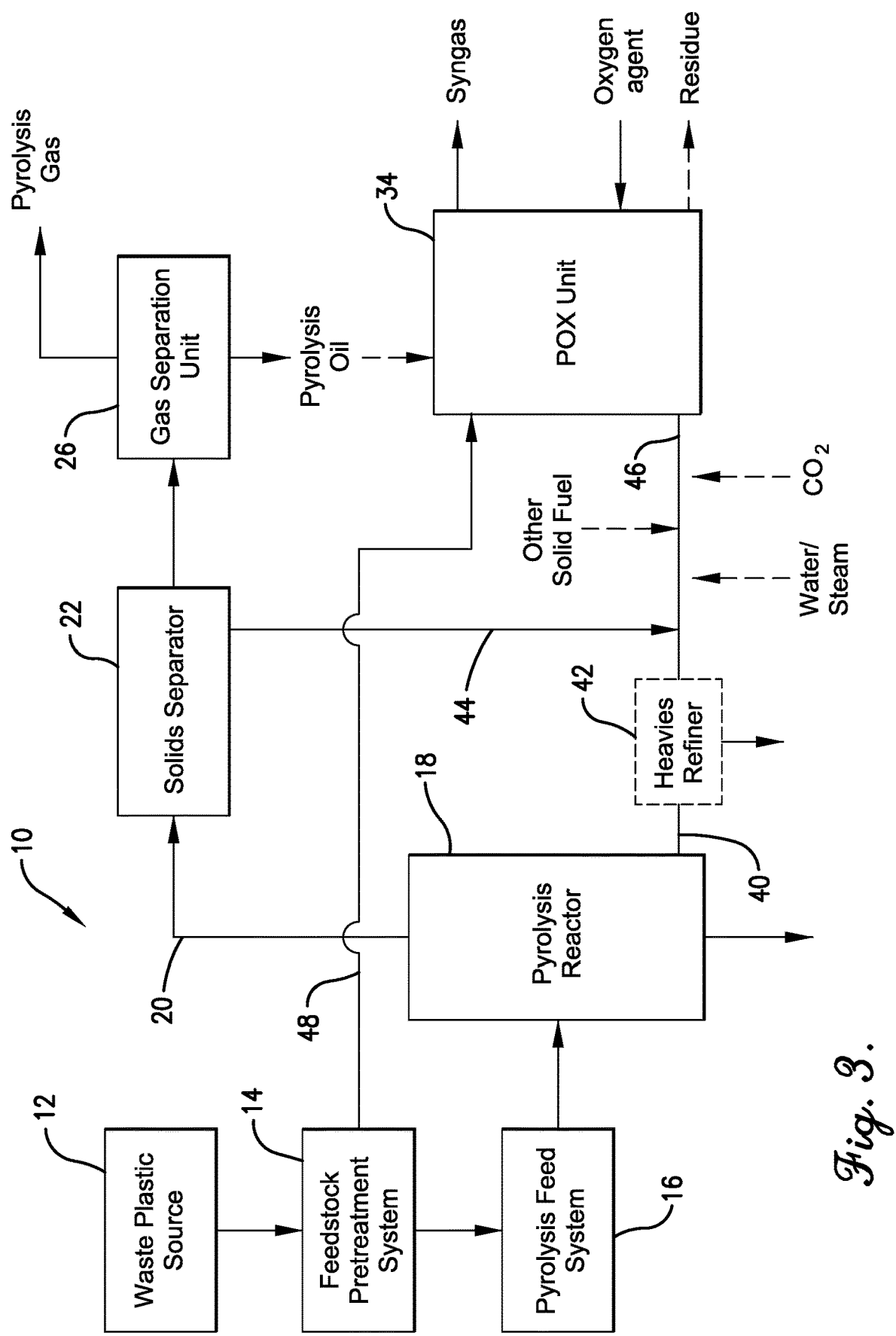
FIG. 3 depicts another exemplary system that may at least partially convert one or more waste plastics into various useful pyrolysis-derived products.

FIG. 3 depicts yet another exemplary system 10 that may be employed to at least partially convert one or more waste plastics, particularly recycled plastic waste, into various useful pyrolysis-derived products. It should be understood that the system shown in FIG. 3 is just one example of a system within which the present disclosure can be embodied. The present disclosure may find application in a wide variety of other systems where it is desirable to efficiently and effectively convert pyrolysis products into various desirable end products. Furthermore, the components or units depicted with dashed lines represents optional streams and/or components that may be found in the exemplary system 10. Thus, there are envisioned embodiments where the components in dashed lines may or may not be present. The exemplary system illustrated in FIG. 3 will now be described in greater detail.

The pyrolysis facility 10 as shown in FIG. 3 comprises a waste plastic source 12, a feedstock pretreatment system 14, a pyrolysis feed system 16, a pyrolysis reactor 18, a solids separator 22, a gas separation unit 26, and a partial oxidation (PDX) unit 34 that may function in the same manner as the same components described above in regard to FIGS. 1 and 2. FIG. 3 demonstrates an embodiment wherein at least a portion of the pyrolysis residue, in the form of a bottoms stream derived from the pyrolysis reactor 18 and/or the pyrolysis residue 44 from the solids separator 22, is introduced into a partial oxidation (PDX) gasification facility in order to produce a recycle content syngas. As shown in FIG. 2, at least a portion of the pyrolysis bottoms stream 40 from the pyrolysis reactor 18 and/or the pyrolysis residue 44 from the solids separator 22 may be introduced into the partial oxidation (PDX) unit 34. Alternatively, or in addition, at least a portion of the pyrolysis oil may also be introduced into the PDX unit, as generally shown in FIG. 3.

As shown in FIG. 3, a pyrolysis bottoms stream 40 may be discharged from the pyrolysis reactor 18. In one embodiment or in combination with any of the mentioned embodiments, this pyrolysis bottoms stream 40 predominantly comprises the pyrolysis residue described above in regard to FIG. 1. For example, the pyrolysis bottoms stream 40 may comprise at least 50, at least 60, at least 70, at least 75, at least 80, at least 85, at least 90, at least 95, at least 96, at least 97, at least 98, at least 99, or at least 99.9 weight percent of the pyrolysis residue based on the total weight of the pyrolysis bottoms stream. Generally, the pyrolysis bottoms stream 40 may be removed from the pyrolysis reactor 18 at a height position that is lower than the discharge point for the pyrolysis effluent 20 removed from the pyrolysis reactor 18.

In one embodiment or in combination with any of the mentioned embodiments, the pyrolysis bottoms stream 40 comprises at least 20, at least 25, at least 30, at least 35, at least 40, at least 45, at least 50, at least 55, at least 60, at least 65, at least 70, at least 75, at least 80, or at least 85 weight percent of C20+ hydrocarbons based on the total weight of the pyrolysis bottoms stream In one embodiment or in combination with any of the mentioned embodiments, the pyrolysis bottoms stream 40 comprises not more than 15, not more than 14, not more than 13, not more than 12, not more than 11, not more than 10, not more than 9, not more than 8, not more than 7, not more than 6, not more than 5, not more than 4, not more than 3, not more than 2, not more than 1, or not more than 0.5 weight percent of water based on the total weight of the pyrolysis bottoms stream.

In one embodiment or in combination with any of the mentioned embodiments, the pyrolysis bottoms stream 40 comprises at least 1, at least 2, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99 weight percent of carbon-containing solids based on the total weight of the pyrolysis bottoms stream. Additionally, or alternatively, in one embodiment or in combination with any of the mentioned embodiments, the pyrolysis bottoms stream comprises not more than 99, not more than 90, not more than 80, not more than 70, not more than 60, not more than 50, not more than 40, not more than 30, not more than 20, not more than 10, not more than 9, not more than 8, not more than 7, not more than 6, not more than 5, or not more than 4 weight percent of carbon-containing solids.

In one embodiment or in combination with any of the mentioned embodiments, the pyrolysis bottoms stream 40 comprises a C:H atomic ratio that is greater than or equal to paraffins or greater than or equal to 0.25:1, 0.3:1, 0.35:1, 0.4:1, or 0.45:1.

In one embodiment or in combination with any of the mentioned embodiments, the pyrolysis bottoms stream 40 comprises not more than 40, 30, 20, 10, 5, 4, 3, 2, or 1 weight percent of pyrolysis oil based on the total weight of the pyrolysis bottoms stream.

Turning back to FIG. 3, at least a portion of the pyrolysis bottoms stream 40 may be introduced into an optional heavies refiner 42 in order to remove at least a portion of the undesirable solids (e.g., metals) from the pyrolysis bottoms stream 40. In one embodiment or in combination with any of the mentioned embodiments, the heavies refiner 42 may remove at least 25, 50, 75, 80, 85, 90, 95, or 99 percent of the metal-containing compounds present in the pyrolysis bottoms stream 40. The heavies refiner 42 may comprise, for example, a cyclone separator, a filter, or any other separator known in the art capable of separating solids.

Turning back to FIG. 3, at least a portion of the pyrolysis bottoms stream 40 may be combined with at least a portion of the pyrolysis residue stream 44 from the solids separator 22. It should be noted that this combined pyrolysis residue stream (i.e., the stream containing the pyrolysis bottoms stream 40 and the pyrolysis residue stream 44) can comprise and exhibit the characteristics described above for the pyrolysis residue in regard to FIG. 1. In one embodiment or in combination with any of the mentioned embodiments, this combined pyrolysis residue stream comprises at least 80, at least 85, at least 90, at least 95, at least 99, or at least 99.9 weight percent of the pyrolysis residue based on the total weight of the combined stream. In certain embodiments, the pyrolysis bottoms stream 40 may be combined with the pyrolysis residue stream 44 after treatment in the heavies refiner 42.

As shown in FIG. 3, at least a portion of the pyrolysis bottoms stream 40 and/or the pyrolysis residue stream 44 may be introduced into a gasifier, such as a partial oxidation (PDX) unit 34. While in the partial oxidation gasifier unit 34, at least a portion of the pyrolysis bottoms stream 40 and/or the pyrolysis residue stream 44 may be subjected to partial oxidation (PDX) gasification. Additionally, or in the alternative, at least a portion of the pyrolysis oil stream from gas separation unit 26 may also be subjected to partial oxidation gasification.

In one embodiment or in combination with any of the mentioned embodiments, the PDX gasification unit may comprise a gas-fed gasifier, a liquid-fed gasifier, a solid-fed gasifier, or a combination thereof.

As shown in FIG. 3, a process is provided for the production of recycle content syngas, wherein the process comprises: (a) charging an oxygen agent and a feedstock composition comprising the pyrolysis bottoms stream 40 and/or the pyrolysis residue stream 44 to a gasification zone within a gasifier; (b) gasifying the feedstock composition together with the oxygen agent in a gasification zone to thereby produce a syngas composition; and (c) discharging at least a portion of the syngas composition and a residue from the gasifier. As shown in FIG. 3, another solid fuel (e.g., a fossil fuel, such as coal, and/or solid waste plastics) may be combined with the pyrolysis bottoms stream 40 and/or the pyrolysis residue stream 44 to produce the gasification feedstock 46.

In one embodiment or in combination with any of the mentioned embodiments, the gasification feedstock 46 comprises at least 0.1, at least 0.5, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 and/or not more than 90, not more than 85, not more than 80, not more than 75, not more than 70, not more than 65, not more than 60, not more than 55, not more than 50, not more than 40, not more than 35, not more than 30, not more than 25, not more than 20, not more than 15, not more than 10, or not more than 5 weight percent of the pyrolysis residue, which can be derived from the pyrolysis bottoms stream 40 and/or the pyrolysis residue stream 44, based on the total weight of the feedstock. More particularly, the gasification feedstock can comprise 1 to 75, 1 to 50, 1 to 40, or 1 to 30 weight percent of the pyrolysis residue, which can be derived from the pyrolysis bottoms stream 40 and/or the pyrolysis residue stream 44, based on the total weight of the gasification feedstock.

As noted above, the gasification feedstock may also comprise another carbonaceous solid fuel, such as coal and/or a solid waste plastic. In one embodiment or in combination with any of the mentioned embodiments, the gasification feedstock may comprise at least 1, at least 10, at least 15, at least 20, at least 25, at least 30, at least 35, at least 40, at least 45, at least 50, at least 55, at least 60, at least 65, at least 70, at least 75, at least 80, or at least 85 and/or not more than 99, not more than 95, or not more than 90 weight percent of a solid fossil fuel, such as coal, and/or a solid waste plastic based on the total weight of the gasification feedstock. More particularly, the gasification feedstock can comprise 10 to 99, 40 to 99, or 75 to 99 weight percent of a solid fossil fuel, such as coal, and/or a solid waste plastic.

In one embodiment or in combination with any of the mentioned embodiments, the gasification feedstock may comprise at least 1, at least 10, at least 15, at least 20, at least 25, at least 30, at least 35, at least 40, at least 45, at least 50, at least 55, at least 60, at least 65, at least 70, at least 75, at least 80, or at least 85 and/or not more than 99, not more than 95, or not more than 90 weight percent of coal based on the total weight of the gasification feedstock, or alternatively based on the weight of solids. More particularly, the gasification feedstock can comprise coal in an amount of 10 to 99, 40 to 99, or 65 to 78, or 75 to 99 weight percent, based on the weight of the gasification feedstock, or alternatively based on the weight of solids.

The quality of the coal employed is not limited. Anthracite, bituminous, sub-bituminous, brown coal, and lignite coal can be sources of coal feedstock. In one embodiment or in combination with any of the mentioned embodiments, to increase the thermal efficiency of the reactor, the coal employed has a carbon content that exceeds 35 or 42 weight percent based on the weight of the coal. Accordingly, bituminous or anthracite coal may be desirable due to their higher energy content.

In one embodiment or in combination with any of the mentioned embodiments, the coal may comprise a moisture content of not more than 25, not more than 20, not more than 15, not more than 10, or not more than 8 weight percent based on the total weight of the coal.

In one embodiment or in combination with any of the mentioned embodiments, the coal has a heat value of at least 11,000 BTU/lb, at least 11,500 BTU/lb, at least 12,500 BTU/lb, at least 13,000 BTU/lb, at least 13,500 BTU/lb, 14,000 BTU/lb, 14,250 BTU/lb, or at least 14,500 BTU/lb.

In one embodiment or in combination with any of the mentioned embodiments, water may be added to the gasification feedstock 46 prior to injection into the gasifier 34 in order to produce a slurry containing water. Thus, in such embodiments, the gasification feedstock is in the form of a slurry. The gasification feedstock 46 comprises at least 1, at least 5, at least 10, at least 15, at least 20, at least 25, at least 28, at least 30, or at least 31 and/or not more than 90, not more than 80, not more than 70, not more than 60, not more than 50, not more than 40, not more than 35, or not more than 30 weight percent of water.

In one embodiment or in combination with any of the mentioned embodiments, the solid fuel, such as the coal and/or waste plastics, may be ground to a size of 2 mm or less. The small size of the solid fuel may be important to assure a uniform suspension in the slurry, to allow sufficient motion relative to the gaseous reactants, to assure substantially complete gasification, and to provide pumpable slurries of high solids content with a minimum of grinding.

Although not pictured in FIG. 3, the gasification facility may comprise a grinding apparatus such as a ball mill, a rod mill, hammer mill, a raymond mill, or an ultrasonic mill, to grind the solid particles of the gasification feedstock, including the pyrolysis residue and additional solid fuel, into desirable particle sizes (e.g., an average diameter of less than 2 mm). It should be noted that the water can be added to the pyrolysis residue and/or the other solid fuel (e.g., coal) while these components are being ground in the grinding apparatus.

The pyrolysis bottoms stream 40 and/or the pyrolysis residue stream 44 may be ground to a suitable particle size, optionally sieved, and then combined with one or more fossil fuel components of the feedstock stream at any location prior to introducing the feedstock stream into the gasification zone within the gasifier. In one embodiment or in combination with any of the mentioned embodiments, the pyrolysis bottoms stream 40 and/or the pyrolysis residue stream 44 may be combined with the solid carbonaceous fuel (e.g., coal and/or waste plastics) in the grinding apparatus. This location may be particularly attractive for a slurry fed gasifier because it may be desirable to use a feed having the highest stable solids concentration possible, and at higher solids concentration, the viscosity of the slurry is also high. The torque and shear forces employed in fossil fuel grinding equipment is high and coupled with the shear thinning behavior of a coal slurry, good mixing of the pre-ground pyrolysis residue with the ground fossil fuel can be obtained in the fossil fuel grinding equipment.

The other solid fuel (e.g., a fossil fuel such as coal), the pyrolysis bottoms stream 40 and/or the pyrolysis residue stream 44 may be ground or milled for multiple purposes. Generally, the pyrolysis bottoms stream 40 and/or the pyrolysis residue stream 44 must be ground to a small size as does the fossil fuel source to (i) allow for faster reaction once inside the gasifier due to mass transfer limitations, (ii) to create a slurry that is stable, fluid and flowable at high concentrations of coal to water, and (iii) to pass through processing equipment such as high-pressure pumps, valves, and feed injectors that have tight clearances. Typically, this means that the solids in the feedstock may be ground to a particle size in which at least 90% of the particles have an average particle size of not more than 4, not more than 3, not more than 2, not more than 1.9, not more than 1.8, or not more than 1.7 mm.

As noted above, the gasification feedstock may in the form of a water-containing slurry. The concentration of solids (e.g., the fossil fuel and tires) in the feedstock stream should not exceed the stability limits of the slurry, or the ability to pump or feed the feedstock at the target solids concentration to the gasifier. In one embodiment or in combination with any of the mentioned embodiments, the solids content of the slurry should be at least 50, at least 55, at least 60, at least 65, at least 70, or at least 75 weight percent, the remainder being a liquid phase that can include water and liquid additives. The upper limit is not particularly limited because it is dependent upon the gasifier design.

The quantity of solids in the feedstock slurry stream and their particle size may be adjusted to maximize the solids content while maintaining a stable and pumpable slurry. In one embodiment or in combination with any of the mentioned embodiments, a pumpable slurry is one which has a viscosity of not more than 30,000 cP, not more than 25,000 cP, not more than 23,000 cP, not more than 20,000 cP, not more than 18,000 cP, not more than 15,000 cP, not more than 13,000 cP, not more than 10,000 cP, not more than 8,000 cP, or not more than 5,000 cP and/or at least 500 cP, at least 1000 cP, at least 1500 cP, at least 2000 cP, or at least 2500 cP at 25° C. and 1 atm.

At higher viscosities, the slurry may become too thick to practically pump. The viscosity measurement to determine the pumpability of the slurry is taken by mixing a sample of the slurry until a homogeneous distribution of particles is obtained, thereafter immediately submerging a Brookfield viscometer with an LV-2 spindle rotating at a rate of 0.5 rpm into the well mixed slurry and taking a reading without delay. Alternatively, a Brookfield R/S rheometer with V80-40 vane spindle operating at a shear rate of 1.83/s can be used. The method of measurement is reported since the measured values between the two rheometers at their difference shear rates will generate different values. However, the cP values stated above apply to either of the rheometer devices and procedures.

In one embodiment or in combination with any of the mentioned embodiments, the gasification feedstock stream 46 comprising the pyrolysis bottoms stream 40, the pyrolysis residue stream 44, the other solid fuel, and the water may be maintained at a temperature sufficient to maintain the stream as a pumpable liquid.

As shown in FIG. 3, the gasification feedstock stream 46 in FIG. 3 may be injected along with the oxygen agent into a refractory-lined combustion chamber of the synthesis gas generating gasifier. In one embodiment or in combination with any of the mentioned embodiments, the feedstock stream and the oxygen agent are sprayed through an injector into a gasification zone that is under significant pressure, typically at least 500, at least 600, at least 800, or at least 1,000 psig. Generally, the velocity or flow rate of the feedstock and oxygen agent streams ejected from the injector nozzle into the combustion chamber can exceed the rate of flame propagation to avoid backflash.

The operating conditions of the gasifier unit 34 and the oxygen agent are described above in regard to FIG. 2. The aforementioned description regarding the gasifier operating conditions (e.g., temperature, pressure, and residence time) and oxygen agents may also apply to the gasification system depicted in FIG. 3.

Other reducible oxygen-containing gases in addition to the oxygen agent may be supplied to the reaction zone, for example, carbon dioxide, nitrogen, or simply air. As shown in FIG. 3, a carbon dioxide stream may be introduced along with the feedstock to serve as carrier gases to propel a feedstock to a gasification zone. Due to the pressure within the gasification zone, these carrier gases may be compressed to provide the motive force for introduction into the gasification zone.

As previously noted, the gasification process desirably employed is a partial oxidation gasification reaction. Generally, to enhance the production of hydrogen and carbon monoxide, the oxidation process involves partial, rather than complete, oxidization of the gasification feedstock and, therefore, may be operated in an oxygen-lean environment, relative to the amount needed to completely oxidize 100 percent of the carbon and hydrogen bonds. In one embodiment or in combination with any of the mentioned embodiments, the total oxygen requirements for the gasifier may be at least 5, at least 10, at least 15, or at least 20 percent in excess of the amount theoretically required to convert the carbon content of the gasification feedstock to carbon monoxide. In general, satisfactory operation may be obtained with a total oxygen supply of 10 to 80 percent in excess of the theoretical requirements. For example, examples of suitable amounts of oxygen per pound of carbon may be in the range of 0.4 to 3.0, 0.6 to 2.5, 0.9 to 2.5, or 1.2 to 2.5 pounds free oxygen per pound of carbon.

Mixing of the feedstock stream and the oxygen agent may be accomplished entirely within the reaction zone by introducing the separate streams of feedstock and oxygen agent so that they impinge upon each other within the reaction zone. In one embodiment or in combination with any of the mentioned embodiments, the oxygen agent stream is introduced into the reaction zone of the gasifier as high velocity to both exceed the rate of flame propagation and to improve mixing with the feedstock stream.

In one embodiment or in combination with any of the mentioned embodiments, the gasification feedstock stream and the oxygen agent can optionally be preheated to a temperature of at least 200° C., at least 300° C., or at least 400° C. However, the gasification process employed does not require preheating the feedstock stream to efficiently gasify the feedstock and a preheat treatment step may result in lowering the energy efficiency of the process.

In one embodiment or in combination with any of the mentioned embodiments, the type of gasification technology employed is a partial oxidation entrained flow gasifier that generates syngas.

An exemplary gasifier that may be used for the gasifier in FIG. 3 is depicted in U.S. Pat. No. 3,544,291.

In one embodiment or in combination with any of the mentioned embodiments, the gasifier is non-catalytic, meaning that the gasifier does not contain a catalyst bed and the gasification process is non-catalytic, meaning that a catalyst is not introduced into the gasification zone as a discrete unbound catalyst.

To avoid fouling downstream equipment from the gasifier (scrubbers, $CO/H_2$ shift reactors, acid gas removal, chemical synthesis), and the piping in-between, the resulting syngas may have a low or no tar content. In one embodiment or in combination with any of the mentioned embodiments, the syngas stream discharged from the gasifier 34 in FIG. 3 may comprise not more than 4, not more than 3, not more than 2, not more than 1, not more than 0.5, not more than 0.2, not more than 0.1, or not more than 0.01 weight percent of tar based on the weight of all condensable solids in the syngas stream. For purposes of measurement, condensable solids are those compounds and elements that condense at a temperature of 15° C. and 1 atm. Examples of tar products include naphthalenes, cresols, xylenols, anthracenes, phenanthrenes, phenols, benzene, toluene, pyridine, catechols, biphenyls, benzofurans, benzaldehydes, acenaphthylenes, fluorenes, naphthofurans, benzanthracenes, pyrenes, acephenanthrylenes, benzopyrenes, and other high molecular weight aromatic polynuclear compounds. The tar content can be determined by GC-MSD.

Generally, the raw syngas stream discharged from the gasification vessel 34 includes such gases as hydrogen, carbon monoxide, and carbon dioxide and can include other gases such as methane, hydrogen sulfide, and nitrogen depending on the fuel source and reaction conditions.

In one embodiment or in combination with any of the mentioned embodiments, the raw syngas stream (the stream discharged from the gasifier 34 and before any further treatment by way of scrubbing, shift, or acid gas removal)

can have the following composition in mole percent on a dry basis and based on the moles of all gases (elements or compounds in gaseous state at 25° C. and 1 atm) in the raw syngas stream:

- a hydrogen content in the range of 15 to 60, 18 to 50, 18 to 45, 18 to 40, 23 to 40, 25 to 40, 23 to 38, 29 to 40, 31 to 40 mole percent;
- a carbon monoxide content of 20 to 75, 20 to 65, 30 to 70, 35 to 68, 40 to 68, 40 to 60, 35 to 55, or 40 to 52 mole percent;
- a carbon dioxide content of 1.0 to 30, 2 to 25, 2 to 21, 10 to 25, or 10 to 20 mole percent;
- a water content of 2.0 to 40, 5 to 35, 5 to 30, or 10 to 30 mole percent;
- a methane content of 0.0 to 30, 0.01 to 15, 0.01 to 10, 0.01 to 8, 0.01 to 7, 0.01 to 5, 0.01 to 3, 0.1 to 1.5, or 0.1 to 1 mole percent;
- a $H_2S$ content of 0.01 to 2.0, 0.05 to 1.5, 0.1 to 1, or 0.1 to 0.5 mole percent;
- a COS content of 0.05 to 1.0, 0.05 to 0.7, or 0.05 to 0.3 mole percent;
- a sulfur content of 0.015 to 3.0, 0.02 to 2, 0.05 to 1.5, or 0.1 to 1 mole percent; and/or
- a nitrogen content of 0.0 to 5, 0.005 to 3, 0.01 to 2, 0.005 to 1, 0.005 to 0.5, or 0.005 to 0.3 mole percent.

In one embodiment or in combination with any of the mentioned embodiments, the syngas comprises a molar hydrogen/carbon monoxide ratio of at least 0.65, at least 0.68, at least 0.7, at least 0.73, at least 0.75, at least 0.78, at least 0.8, at least 0.85, at least 0.88, at least 0.9, at least 0.93, at least 0.95, at least 0.98, or at least 1.

The remaining residue waste formed in the gasifier 34 may be removed and purged from the system.

The gas components can be determined by FID-GC and TCD-GC or any other method recognized for analyzing the components of a gas stream.

Turning back to FIG. 3, at least a portion of the pyrolysis residue 44 from the solids separator 22 may be introduced into an optional regenerator 30 for regeneration, generally by combustion. After regeneration, at least a portion of the hot regenerated solids can be reintroduced directly into the pyrolysis reactor 18. Additionally, or alternatively, at least a portion of the solid particles recovered in the solids separator 22 may be directly introduced back into the pyrolysis reactor 18, especially if the solid residue contains a notable amount of unconverted plastic waste. Furthermore, residual solids can be removed from the regenerator 26 via a solids removal unit 32 and bled out of the system.

In one embodiment or in combination with any of the mentioned embodiments, the waste plastic source 12, feedstock pretreatment system 14, pyrolysis feed system 16, pyrolysis reactor 18, solids separator 22, gas separation unit 26, and PDX unit 34 may be in fluid communication between all units or some of the recited units. For example, the pyrolysis reactor 18 may be in fluid communication with the PDX unit 34. In one embodiment or in combination with any of the mentioned embodiments, fluid communication comprises jacketed piping, traced piping, and/or insulated piping.

In one embodiment or in combination with any of the mentioned embodiments, the pyrolysis bottoms stream 44 may be in the form of a pumpable liquid and may be in fluid communication with the feed injector of the PDX gasifier unit 34. Alternatively, the pyrolysis bottoms stream 44 may be in the form of a pumpable liquid and may be in fluid communication with the gasification facility at a point prior to the feed injector of the PDX gasifier unit 34.

In one embodiment or in combination with any of the mentioned embodiments, the pyrolysis reactor 18 is not in fluid communication with the PDX unit 34.

Lastly, as shown in FIG. 3, a separate solid waste plastic stream 48 from the feedstock pretreatment system 14 may be separately introduced into the gasifier unit 34 in addition to the gasification feedstock 46.

Cracking Facility

FIG. 4 depicts another exemplary chemical recycling facility or system 400 that may be employed to at least partially convert one or more waste plastics, particularly recycled plastic waste, into various useful pyrolysis-derived products. It should be understood that the system 400 shown in FIG. 4 is just one example of a system within which the present disclosure can be embodied.

FIG. 4 illustrates a system for processing waste material that generally includes a pyrolysis facility 410 and a cracker facility 420. The pyrolysis facility 410 may utilize recycled waste, such as, for example, mixed plastic waste, to provide a stream of recycle content pyrolysis gas (r-pyrolysis gas) 110 and a stream of recycle content pyrolysis oil (r-pyoil) 112. As used herein, the term "recycle content" means being or comprising a composition that is directly and/or indirectly derived from waste plastic. As used herein, the term "directly derived" 'means having at least one physical component originating from waste plastic, while "indirectly derived" means having an assigned recycle content that i) is attributable to waste plastic, but ii) that is not based on having a physical component originating from waste plastic.

As used herein, "r-pyoil" means a composition of matter that is liquid when measured at 25° C. and 1 atm, and at least a portion of which is obtained from the pyrolysis of recycled waste. As used herein, "r-pyrolysis gas" means a composition of matter that is gaseous when measured at 25° C. and 1 atm, and at least a portion of which is obtained from the pyrolysis of recycled waste.

As shown in FIG. 4, at least a portion of the r-pyrolysis gas stream 110 and/or r-pyrolysis oil stream 112 formed in the pyrolysis facility 410 may be sent to a cracker facility 420, wherein the stream may be processed to form a stream of recycle content olefin (r-olefin). As used herein, the term "cracking" refers to the process for breaking down complex organic molecules into simpler molecules by the breaking of carbon-carbon double bonds. As used herein the terms "cracker facility," and "cracking facility" refer to a facility that includes all equipment, lines, and controls necessary to carry out cracking of a feedstock derived from waste plastic. A cracking facility can include one or more cracker furnaces, as well as downstream separation equipment used to process the effluent of the cracker furnace(s). As used herein, the term "cracker furnace" or "cracking furnace" refer to a heated enclosure having internal tubes through which are flowed streams that undergo thermal cracking.

The pyrolysis facility 410 shown in FIG. 4 may comprise one embodiment or in combination with any of the mentioned embodiments of pyrolysis facilities described herein previously. In one embodiment or in combination with any of the mentioned embodiments, the pyrolysis gas 110 and/or pyrolysis oil 120 directly from the pyrolysis unit (e.g., the raw r-pyrolysis gas and raw r-pyrolysis oil) may be subjected to one or more treatment steps prior to being introduced into downstream units, such as a cracking facility 420. Examples of suitable treatment steps can include, but are not limited to, separation of less desirable components, e.g., nitrogen-containing compounds, oxygenates, and/or olefins and aromatics), distillation to provide specific pyrolysis oil compositions, and preheating.

In one embodiment or in combination with any of the mentioned embodiments, the stream of pyrolysis gas 110 introduced into a cracker facility 420 may comprise predominantly C2 to C4 olefins and paraffins. For example, in one embodiment or in combination with any of the mentioned embodiments, the r-pyrolysis gas can comprise at least 50, at least 55, at least 60, at least 65, at least 70, at least 75, at least 80, at least 85, at least 90, or at least 95 and/or not more than 99, not more than 97, not more than 95, not more than 90, not more than 85, not more than 80, not more than 75, not more than 70, not more than 65, or not more than 60 weight percent of C2 to C4 olefins and paraffins, based on the total weight of the r-pyrolysis gas stream.

In one embodiment or in combination with any of the mentioned embodiments, the r-pyrolysis gas stream 110 may comprise at least 20, at least 25, at least 30, at least 35, at least 40, at least 45, or at least 50 weight percent and/or not more than 75, not more than 70, not more than 65, not more than 60, not more than 55, or not more than 50 weight percent of ethylene and/or propylene, based on the total weight of the r-pyrolysis gas stream 110. The r-pyrolysis gas stream 110 may also comprise ethane and/or propane in an amount of at least 5, at least 10, at least 15, at least 20, or at least 25 and/or not more than 50, not more than 45, not more than 40, not more than 35, not more than 30, or not more than 25 weight percent of ethane and/or propane, based on the total weight of the r-pyrolysis gas stream 110.

The ethylene to ethane weight ratio in the r-pyrolysis gas stream 110 can be at least 1:1, at least 1.1:1, at least 1.2:1, at least 1.25:1, at least 1.3:1, at least 1.35:1, at least 1.4:1, at least 1.45:1, at least 1.5:1 and/or not more than 3:1, not more than 2.75:1, not more than 2.5:1, not more than 2.25:1, not more than 2.1:1. Additionally, or in the alternative, the propylene to propane weight ratio in the r-pyrolysis gas stream 110 can be at least 1:1, at least 1.1:1, at least 1.2:1, at least 1.25:1, at least 1.3:1, at least 1.35:1, at least 1.4:1, at least 1.45:1, at least 1.5:1 and/or not more than 3:1, not more than 2.75:1, not more than 2.5:1, not more than 2.25:1, not more than 2.1:1.

In one embodiment or in combination with any of the mentioned embodiments, the r-pyrolysis gas stream 110 may comprise at least 20, at least 25, at least 30, at least 35, at least 40, at least 45, or at least 50 weight percent and/or not more than 75, not more than 70, not more than 65, not more than 60, not more than 55, or not more than 50 weight percent of ethylene, based on the total weight of the r-pyrolysis gas stream 110, and it may also comprise ethane in an amount of at least 5, at least 10, at least 15, at least 20, or at least 25 and/or not more than 50, 45, 40, 35, 30, or 25 weight percent, based on the total weight of the r-pyrolysis gas stream 110. The ethylene to ethane weight ratio in the r-pyrolysis gas stream 110 can be at least 1:1, at least 1.1:1, at least 1.2:1, at least 1.25:1, at least 1.3:1, at least 1.35:1, at least 1.4:1, at least 1.45:1, at least 1.5:1 and/or not more than 3:1, not more than 2.75:1, not more than 2.5:1, not more than 2.25:1, not more than 2.1:1.

In one embodiment or in combination with any of the mentioned embodiments, the r-pyrolysis gas stream 110 may comprise at least 20, at least 25, at least 30, at least 35, at least 40, at least 45, or at least 50 weight percent and/or not more than 75, not more than 70, not more than 65, not more than 60, not more than 55, or not more than 50 weight percent of propylene, based on the total weight of the r-pyrolysis gas stream 110, and it may also comprise propane in an amount of at least 5, at least 10, at least 15, at least 20, or at least 25 and/or not more than 50, 45, 40, 35, 30, or 25 weight percent, based on the total weight of the r-pyrolysis gas stream 110. The propylene to propane weight ratio in the r-pyrolysis gas stream 110 can be at least 1:1, at least 1.1:1, at least 1.2:1, at least 1.25:1, at least 1.3:1, at least 1.35:1, at least 1.4:1, at least 1.45:1, at least 1.5:1 and/or not more than 3:1, not more than 2.75:1, not more than 2.5:1, not more than 2.25:1, not more than 2.1:1.

In one embodiment or in combination with any of the mentioned embodiments, the r-pyrolysis gas stream 110 can have a methane content of at least 5, at least 10, at least 15, at least 20, at least 25, at least 30, or at least 35 and/or not more than 60, 55, 50, 45, 35, 30, 25, or 20 weight percent, based on the total weight of the r-pyrolysis gas stream 110. Additionally, or in the alternative, the r-pyrolysis gas stream 110 can comprise at least 0.5, at least 1, at least 2, at least 5, at least 8, at least 10, at least 12, at least 15 and/or not more than about 35, 30, 25, 20, 15, 10, 8, 5 weight percent of butadiene, based on the total weight of the composition.

In one embodiment or in combination with any of the mentioned embodiments, the r-pyrolysis gas stream 110 comprises not more than about 35, not more than 30, not more than 25, not more than 20, not more than 15, not more than 10, not more than 5 weight percent of C5 and heavier components, based on the total weight of the composition. The r-pyrolysis gas stream 110 may also comprise not more than about 35, not more than 30, not more than 25, not more than 20, not more than 15, not more than 10, not more than 5 weight percent of aromatics, based on the total weight of the composition. The r-pyrolysis gas stream 110 can comprise at least 0.1, at least 0.5, at least 1, at least 2, at least 3, at least 4, at least 5, at least 8, at least 10, or at least 12 and/or not more than 25, not more than 20, not more than 18, not more than 15, not more than 12, not more than 10, not more than 8, or not more than 5 weight percent of one or more nitrogen containing compounds, based on the total weight of the stream 110.

Further, in one embodiment or in combination with any of the mentioned embodiments, the r-pyrolysis gas stream 110 introduced into the cracker facility can have at least one of the following properties:
  (a) C4 hydrocarbons in an amount of not more than 20, not more than 15, not more than 10, not more than 5, not more than 2, not more than 1, not more than 0.5 weight percent;
  (b) hydrogen in an amount of not more than 10, not more than 8, not more than 6, not more than 5, not more than 2, not more than 1 weight percent;
  (c) C3+ diolefins in an amount of not more than 10, not more than 8, not more than 6, not more than 5, not more than 2, not more than 1 weight percent;
  (d) C4+ olefins in an amount of not more than 10, not more than 8, not more than 6, not more than 5, not more than 2, not more than 1 weight percent;
  (e) C4 paraffins in an amount of not more than 5, not more than 3, not more than 2, not more than 1, not more than 0.5, not more than 0.1 weight percent;
  (f) halogens in an amount of not more than 1, not more than 0.5, not more than 0.1, not more than 0.05, not more than 0.01 ppm;
  (g) carbonyls in an amount of not more than 100, not more than 75, not more than 50, not more than 25, not more than 10, not more than 5 ppm;
  (h) carbon dioxide in an amount of not more than 100, not more than 75, not more than 50, not more than 25, not more than 10, not more than 5 ppm;
  (i) carbon monoxide in an amount of not more than 2500, not more than 2000, not more than 1500, not more than 1000, not more than 750, not more than 500, not more than 250, not more than 100, not more than 50, not more than 25, not more than 10 ppm;

(j) arsine and/or phosphine in an amount of not more than 15, not more than 10, not more than 8, not more than 5, not more than 2, not more than 1 ppb; and (k) sulfur-containing compounds in an amount of not more than 100, not more than 75, not more than 50, not more than 25, not more than 10, not more than 5 ppm, wherein each of the above quantities are in amounts by weight, based on the total weight of the composition. At least two, three, four, five, six, seven, eight, or all of the properties may be present in the r-pyrolysis gas stream 110 introduced into the cracker facility.

In one embodiment or in combination with any of the mentioned embodiments, the r-pyrolysis gas stream 110 can have a pressure of at least 200 (13.8 barg), at least 250 (17.2 barg), at least 300 (20.7 barg), at least 350 (24.1 barg), at least 400 (27.6 barg), at least 450 (31.0 barg), or at least 500 (34.5 barg), all in psig. Additionally, or in the alternative, the pressure can be not more than 500 (34.5 barg), not more than 450 (31.0 barg), not more than 400 (27.6 barg), not more than 350 (24.1 barg), not more than 300 (20.7 barg), not more than 250 (17.2 barg), not more than 200 (13.78 barg), not more than 150 (10.35 barg), or not more than 100 (6.89 barg), all in psig.

The temperature of the r-pyrolysis gas stream 110 can be at least 250, at least 300, at least 350, at least 400, at least 450, at least 500, at least 550, at least 600, or at least 650° C. and/or not more than 1000, not more than 950, not more than 900, not more than 850, not more than 800, not more than 750, not more than 700, not more than 650, not more than 600, not more than 550, or not more than 500° C. The temperature and/or pressure of the r-pyrolysis gas can be measured before or after a compressor or heat exchanger, at the outlet of the pyrolysis facility or at a location of the cracker facility 420 where the pyrolysis gas is introduced.

In one embodiment or in combination with any of the mentioned embodiments, the r-pyoil stream 112 may comprise at least 55, or at least 60, or at least 65, or at least 70, or at least 75, or at least 80, or at least 85, or at least 90, or at least 95, in each case weight percent of C4 to C30 hydrocarbons, and as used herein, hydrocarbons include aliphatic, cycloaliphatic, aromatic, and heterocyclic compounds. In one embodiment or in combination with any of the mentioned embodiments, the r-pyoil stream 112 can predominantly comprise C5 to C25, C5 to C22, or C5 to C20 hydrocarbons, or may comprise at least 55, at least 60, at least 65, at least 70, at least 75, at least 80, at least 85, at least 90, or at least 95 weight percent of C5 to C25, C5 to C22, or C5 to C20 hydrocarbons.

In one embodiment or in combination with any of the mentioned embodiments, the r-pyoil stream 112 can comprise C4-C12 aliphatic compounds (branched or unbranched alkanes and alkenes including diolefins, and alicyclics) and C13-C22 aliphatic compounds in a weight ratio of more than 1:1, or at least 1.25:1, or at least 1.5:1, or at least 2:1, or at least 2.5:1, or at least 3:1, or at least 4:1, or at least 5:1, or at least 6:1, or at least 7:1, 10:1, 20:1, or at least 40:1, each by weight and based on the weight of the r-pyoil stream 112.

In one embodiment or in combination with any of the mentioned embodiments, the r-pyoil stream 112 can comprise C13-C22 aliphatic compounds (branched or unbranched alkanes and alkenes including diolefins, and alicyclics) and C4-C12 aliphatic compounds in a weight ratio of more than 1:1, or at least 1.25:1, or at least 1.5:1, or at least 2:1, or at least 2.5:1, or at least 3:1, or at least 4:1, or at least 5:1, or at least 6:1, or at least 7:1, 10:1, 20:1, or at least 40:1, each by weight and based on the weight of the r-pyoil stream 112.

In an embodiment, the two aliphatic hydrocarbons (branched or unbranched alkanes and alkenes, and alicyclics) having the highest concentration in the r-pyoil are in a range of C5-C18, or C5-C16, or C5-C14, or C5-C10, or C5-C8, inclusive.

The r-pyoil stream 112 includes one or more of paraffins, naphthenes or cyclic aliphatic hydrocarbons, aromatics, aromatic containing compounds, olefins, oxygenated compounds and polymers, heteroatom compounds or polymers, and other compounds or polymers.

For example, in one embodiment or in combination with any of the mentioned embodiments, the r-pyoil stream 112 may comprise at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent and/or not more than 99, or not more than 97, or not more than 95, or not more than 93, or not more than 90, or not more than 87, or not more than 85, or not more than 83, or not more than 80, or not more than 78, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, in each case weight percent of paraffins (or linear or branched alkanes), based on the total weight of the r-pyoil stream 112. Examples of ranges for the amount of paraffin contained in the r-pyoil stream 112 is from 5 to 50, or 5 to 40, or 5 to 35, or 10- to 35, or 10 to 30, or 5 to 25, or 5 to 20 in each case as weight percent, based on the weight of the r-pyoil composition.

In one embodiment or in combination with any of the mentioned embodiments, the r-pyoil stream 112 can include naphthenes or cyclic aliphatic hydrocarbons in amount of zero, or at least 1, or at least 2, or at least 5, or at least 8, or at least 10, or at least 15, or at least 20, in each case weight percent and/or not more than 50, or not more than 45, or not more than 40, or not more than 35, or not more than 30, or not more than 25, or not more than 20, or not more than 15, or not more than 10, or not more than 5, in each case weight percent, based on the weight of a r-pyoil. Examples of ranges for the amount of naphthenes (or cyclic aliphatic hydrocarbons) contained in the r-pyoil stream 112 is from 0-35, or 1-30, or 2 to 25, or 2 to 20, or 2 to 15, or 2 to 10, or 1 to 10, in each case as weight percent, based on the weight of the r-pyoil stream 112.

In one embodiment or in combination with any of the mentioned embodiments, the r-pyoil stream 112 comprises not more than 30, or not more than 25, or not more than 20, or not more than 15, or not more than 10, or not more than 8, or not more than 5, or not more than 2, or not more than 1, in each case weight percent of aromatics, based on the total weight of the r-pyoil stream 112. As used herein, the term "aromatics" refers to the total amount (in weight) of benzene, toluene, xylene, and styrene. The r-pyoil stream 112 may include at least 1, or at least 2, or at least 5, or at least 8, or at least 10, in each case weight percent of aromatics, based on the total weight of the r-pyoil stream 112.

In one embodiment or in combination with any of the mentioned embodiments, the r-pyoil stream 112 can include aromatic containing compounds in an amount of not more than 30, or not more than 25, or not more than 20, or not more than 15, or not more than 10, or not more than 8, or not more than 5, or not more than 2, or not more than 1, in each case weight, or not detectable, based on the total weight of the r-pyoil stream 112. Aromatic containing compounds includes the above-mentioned aromatics and any compounds containing an aromatic moiety, such as terephthalate residues and fused ring aromatics such as the naphthalenes and tetrahydronaphthalene.

In one embodiment or in combination with any of the mentioned embodiments, the r-pyoil stream 112 can include olefins in amount of at least 1, or at least 2, or at least 5, or at least 8, or at least 10, or at least 15, or at least 20, or at least 30, or at least 40, or at least 45, or at least 50, or at least 55, or at least 60, or at least or at least 65, in each case weight percent olefins and/or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, or not more than 10, in each case weight percent, based on the weight of a r-pyoil stream 112. Olefins include mono- and di-olefins. Examples of suitable ranges include olefins present in an amount ranging from 40 to 85, or 45 to 85, or 50 to 85, or 55 to 85, or 60 to 85, or 65 to 85, or 40 to 80, or 45 to 80, or 50 to 80, or 55 to 80, or 60 to 80, or 65 to 80, 45 to 80, or 50 to 80, or 55 to 80, or 60 to 80, or 65 to 80, or 40 to 75, or 45 to 75, or 50 to 75, or 55 to 75, or 60 to 75, or 65 to 75, or 40 to 70, or 45 to 70, or 50 to 70, or 55 to 70, or 60 to 70, or 65 to 70, or 40 to 65, or 45 to 65, or 50 to 65, or 55 to 65, in each case as wt. % based on the weight of the r-pyoil stream 112.

In one embodiment or in combination with any of the mentioned embodiments, the r-pyoil stream 112 can include oxygenated compounds or polymers in amount of zero or at least 0.01, or at least 0.1, or at least 1, or at least 2, or at least 5, in each case weight percent and/or not more than 20, or not more than 15, or not more than 10, or not more than 8, or not more than 6, or not more than 5, or not more than 3, or not more than 2, in each case weight percent oxygenated compounds or polymers, based on the weight of a r-pyoil stream 112. Oxygenated compounds and polymers are those containing an oxygen atom. Examples of suitable ranges include oxygenated compounds present in an amount ranging from 0-20, or 0-15, or 0-10, or 0.01-10, or 1-10, or 2-10, or 0.01-8, or 0.1-6, or 1-6, or 0.01-5, in each case as wt. % based on the weight of the r-pyoil stream 112.

In an embodiment or in combination with any embodiment mentioned herein the sulfur content of the r-pyoil stream 112 does not exceed 2.5 wt. %, or is not more than 2, or not more than 1.75, or not more than 1.5, or not more than 1.25, or not more than 1, or not more than 0.75, or not more than 0.5, or not more than 0.25, or not more than 0.1, or not more than 0.05, desirably or not more than 0.03, or not more than 0.02, or not more than 0.01, or not more than 0.008, or not more than 0.006, or not more than 0.004, or not more than 0.002, or is not more than 0.001, in each case weight percent based on the weight of the r-pyoil stream 112.

In one embodiment or in combination with any of the mentioned embodiments, the weight ratio of paraffin to naphthene can be at least 1:1, or at least 1.5:1, or at least 2:1, or at least 2.2:1, or at least 2.5:1, or at least 2.7:1, or at least 3:1, or at least 3.3:1, or at least 3.5:1, or at least 3.75:1, or at least 4:1, or at least 4.25:1, or at least 4.5:1, or at least 4.75:1, or at least 5:1, or at least 6:1, or at least 7:1, or at least 8:1, or at least 9:1, or at least 10:1, or at least 13:1, or at least 15:1, or at least 17:1, based on the weight of the r-pyoil stream 112.

In one embodiment or in combination with any of the mentioned embodiments, the weight ratio of paraffin and naphthene combined to aromatics can be at least 1:1, or at least 1.5:1, or at least 2:1, or at least 2.5:1, or at least 2.7:1, or at least 3:1, or at least 3.3:1, or at least 3.5:1, or at least 3.75:1, or at least 4:1, or at least 4.5:1, or at least 5:1, or at least 7:1, or at least 10:1, or at least 15:1, or at least 20:1, or at least 25:1, or at least 30:1, or at least 35:1, or at least 40:1, based on the weight of the r-pyoil stream 112. In one embodiment or in combination with any of the mentioned embodiments, the ratio of paraffin and naphthene combined to aromatics in the r-pyoil stream 112 can be in a range of from 1:1-7:1, or 1:1-5:1, 1:1-4:1, or 1:1-3:1.

In one embodiment or in combination with any of the mentioned embodiments, the r-pyoil stream 112 may have a boiling point curve defined by one or more of its 10%, its 50%, and its 90% boiling points, as defined below. As used herein, "boiling point" refers to the boiling point of a composition as determined by ASTM D2887-13. Additionally, as used herein, an "x % boiling point," refers to a boiling point at which x percent by weight of the composition boils per ASTM D-2887-13.

In one embodiment or in combination with any of the mentioned embodiments, the 90% boiling point of the r-pyoil stream 112 can be not more than 350, or not more than 325, or not more than 300, or not more than 295, or not more than 290, or not more than 285, or not more than 280, or not more than 275, or not more than 270, or not more than 265, or not more than 260, or not more than 255, or not more than 250, or not more than 245, or not more than 240, or not more than 235, or not more than 230, or not more than 225, or not more than 220, or not more than 215, not more than 200, not more than 190, not more than 180, not more than 170, not more than 160, not more than 150, or not more than 140, in each case ° C. and/or at least 200, or at least 205, or at least 210, or at least 215, or at least 220, or at least 225, or at least 230, in each case ° C. and/or not more than 25, 20, 15, 10, 5, or 2 weight percent of the r-pyoil stream 112 may have a boiling point of 300° C. or higher.

Turning now to FIGS. 5-8, several embodiments of the integration of pyrolysis 410 and cracker 420 facilities are shown. In each of FIGS. 5-8, systems for processing waste plastic are shown that includes a pyrolysis facility 410 and at least one cracker facility 420 configured to receive a stream of r-pyrolysis oil 112 and/or r-pyrolysis gas 110 from the pyrolysis facility.

Turning now to FIG. 5, a stream of waste plastic 100 may be introduced into a pyrolysis facility 410 to provide a stream of r-pyrolysis gas 110. The pyrolysis gas stream 110 may optionally be treated in a treatment zone (not shown), and thereafter all or a portion of the stream of r-pyrolysis gas 110 may be routed to a cracker facility 420. In one embodiment or in combination with any of the mentioned embodiments, the r-pyrolysis gas stream 110 (and, in particular, a stream of r-pyrolysis gas that has not been produced in a cracker furnace) may be introduced into a location downstream of the cracker furnace 430.

Optionally, all or a portion of the r-pyoil stream 112 may be combined with a cracker feedstock stream 116, which can be thermally cracked in the cracker furnace 430 to provide an olefin-containing effluent stream 117 from the furnace 430. As shown in FIG. 5, at least a portion of the r-pyrolysis gas stream 110 may be combined with the olefin-containing effluent stream 117 and the combined stream 119 may be introduced into the separation zone 440 of the cracker facility 420. In the separation zone 440, at least a portion of the combined stream 119 may be separated to form at least one recycle content olefin (r-olefin) stream 118.

In one embodiment or in combination with any of the mentioned embodiments, the combined stream 119 of olefin-containing effluent and r-pyrolysis gas can include at least 5, at least 10, at least 15, at least 20, at least 25, at least 30, at least 35, at least 40, at least 45, at least 50, at least 55, at least 60, at least 65, at least 70, at least 75, at least 80, at least 85, or at least 90 and/or not more than about 95, not more than 90, not more than 85, not more than 80, not more than 75, not more than 70, not more than 65, not more than 60, not more than 55, not more than 50, not more than 45, not more than 40, not more than 35, or not more than 30 weight percent of the r-pyrolysis gas, based on the total weight of the combined stream 119.

The olefin-containing effluent may be present in an amount of at least 5, at least 10, at least 15, at least 20, at least 25, at least 30, at least 35, at least 40, at least 45, at least 50, at least 55, at least 60, at least 65, at least 70, at least 75, at least 80, at least 85, or at least 90 and/or not more than about 95, not more than 90, not more than 85, not more than 80, not more than 75, not more than 70, not more than 65, not more than 60, not more than 55, not more than 50, not more than 45, not more than 40, not more than 35, or not more than 30 weight percent, based on the total weight of the combined stream 119.

In one embodiment or in combination with any of the mentioned embodiments, the weight ratio of r-pyrolysis gas to olefin-containing effluent in the combined stream 119 downstream of the furnace outlet is at least 1:10, at least 1:8, at least 1:6, at least 1:5, at least 1:4, at least 1:3, at least 1:2.5, at least 1:2, at least 1:1.5 or at least 1:1 and/or not more than about 10:1, not more than 8:1, not more than 6:1, not more than 5:1, not more than 4:1, not more than 3:1, not more than 2.5:1, not more than 2:1, not more than 1.5:1, or not more than 1:1.

Figure 6:
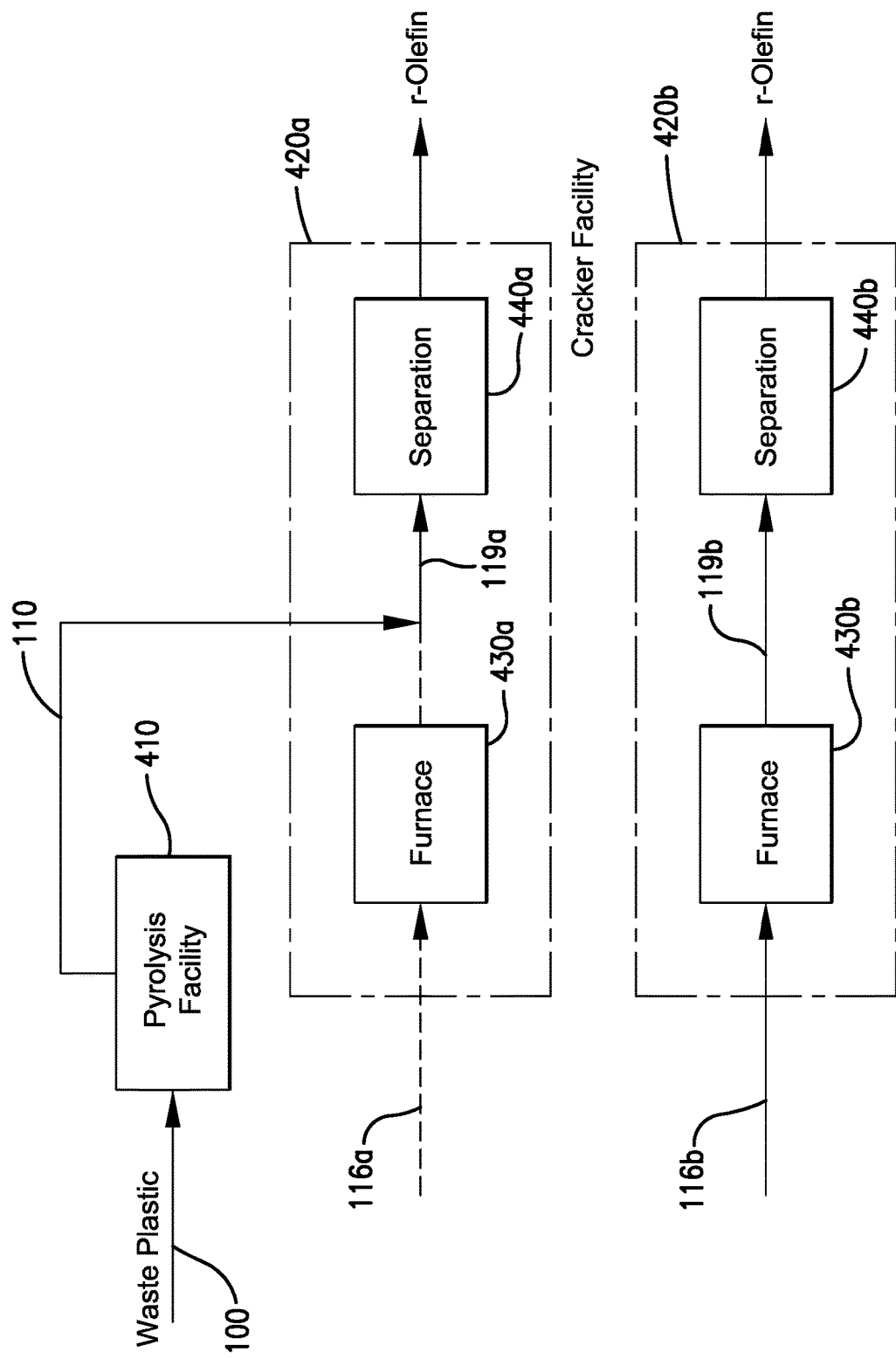
FIG. 6 depicts another exemplary system for processing waste plastic that includes a pyrolysis facility and a cracker facility, particularly illustrating other embodiments of an integration strategy.

Turning now to FIG. 6, another system for processing waste plastic is shown that comprises a pyrolysis facility 410 and two cracker facilities 420*a,b* operated in parallel. Each cracker facility 420*a,b* comprises a cracker furnace 430*a,b* and a separation zone 440*a,b* downstream of each of the cracker furnaces 430*a,b*. In one embodiment or in combination with any of the mentioned embodiments as generally shown in FIG. 6, at least a portion of the r-pyrolysis gas stream 110 formed from the pyrolysis of waste plastic feed stream 110 in the pyrolysis facility 410 can be introduced into one of the two cracker facilities 420*a* at a location downstream of the cracker furnace 430*a*.

In one embodiment or in combination with any of the mentioned embodiments, the introduction of r-pyrolysis gas stream 110 into the separation zone 430*a* may reduce the flow rate of olefin-containing effluent stream 117*a* needed from the cracker furnace 430*a* and, in some embodiments, may make it unnecessary to operate the cracker furnace 430*a*. For example, in some embodiments, the total mass flow rate of olefin-containing effluent 117*a* from the cracker furnace 430*a* outlet may be reduced by at least 5, at least 10, at least 15, at least 20, at least 25, at least 30, at least 35, at least 40, at least 45, at least 50, at least 55, at least 60, at least 65, at least 70, or at least 75 percent, as compared to when the r-pyrolysis gas stream 110 is introduced into the cracker facility. As a result, the mass flow rate of the cracker feedstock stream 116*a* may be reduced by at least 5, at least 10, at least 15, at least 20, at least 25, at least 30, at least 35, at least 40, at least 45, at least 50, at least 55, at least 60, at least 65, at least 70, or at least 75 percent, as compared to when the r-pyrolysis gas stream 110 is introduced into the cracker facility 430*a*.

In other embodiments, the cracker furnace 430*a*, which was previously used to produce an olefin-containing effluent 117*a* separated in the downstream separation zone 440*a*, may be idle so that the total mass flow rate of the olefin-containing effluent 117*a* and/or the cracker feed stock stream 116*a* can be at least 90, at least 92, at least 95, at least 97, at least 99% lower than when the r-pyrolysis gas stream 110 was not introduced into the cracker facility. In one embodiment or in combination with any of the mentioned embodiments, the feed to the fractionation section (or first column therein) of the separation facility 440*a* can comprise not more than 20, not more than 15, not more than 10, not more than 5, not more than 2, not more than 1, or not more than 0.5 weight percent of an olefin-containing effluent stream from the cracker furnace 430*a*, based on the total weight of the feed stream 117*a*.

In one embodiment or in combination with any of the mentioned embodiments, the cracker furnace 430*a* may be idle and at least 80, at least 85, at least 90, at least 95, at least 97, at least 99, or at least 100 percent of the feed to the separation zone of the cracker facility 430*a* can come from the pyrolysis facility (e.g., the r-pyrolysis gas stream 110). In other embodiments, the cracker furnace 430*a* may be operational, but make up less than 80, not more than 75, not more than 70, not more than 65, not more than 60, not more than 55, not more than 50, not more than 45, not more than 40, not more than 35, or not more than 30 weight percent of the feed to the separation zone 440*a* downstream of the cracker furnace 430*a*. In one embodiment or in combination with any of the mentioned embodiments, olefin-containing effluent from the cracker furnace of the second cracker facility can make up at least 90, at least 95, at least 99, or all of the feed to the second separation zone.

Similarly, in some embodiments wherein the cracker facility includes two or more furnaces operated in parallel that share a common separation zone, introduction of r-pyrolysis gas may result in a reduction of olefin-containing effluent from, and/or cracker feedstock to, at least one of the cracker furnaces. A schematic depiction of such a facility 600 is provided in FIG. 7.

In one embodiment or in combination with any of the mentioned embodiments, introducing of r-pyrolysis gas stream 110 into a location downstream of at least one of the furnace outlets of furnace 430*a* and 430*b* may result in a reduction of the mass flow rate of the olefin-containing effluent 117*a,b* from one or both furnaces 430*a,b* in an amount of at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95 percent, based on the total the mass flow rate of the olefin-containing effluent stream 117*a,b* from one or both furnaces 430*a,b*.

In one embodiment or in combination with any of the mentioned embodiments, one or more of the furnaces 430*a,b* may be operational at the same or a reduced feed or product rate, while one or more other furnaces 430*a,b* may be idle. Although shown as including only two furnaces 430*a,b*, it should be understood that cracking facilities 420*a,b* according to the present disclosure can include at least two, three, four, five, six, seven, eight or nine or more furnaces feeding a single separation zone 440.

In one embodiment or in combination with any of the mentioned embodiments wherein the cracker facility 420 includes two or more furnaces 430, the effluent streams 117 from the furnaces 430 may be routed to two or more separation zones 440*a,b*. One example of such a system is provided in FIG. 8.

Figure 8:
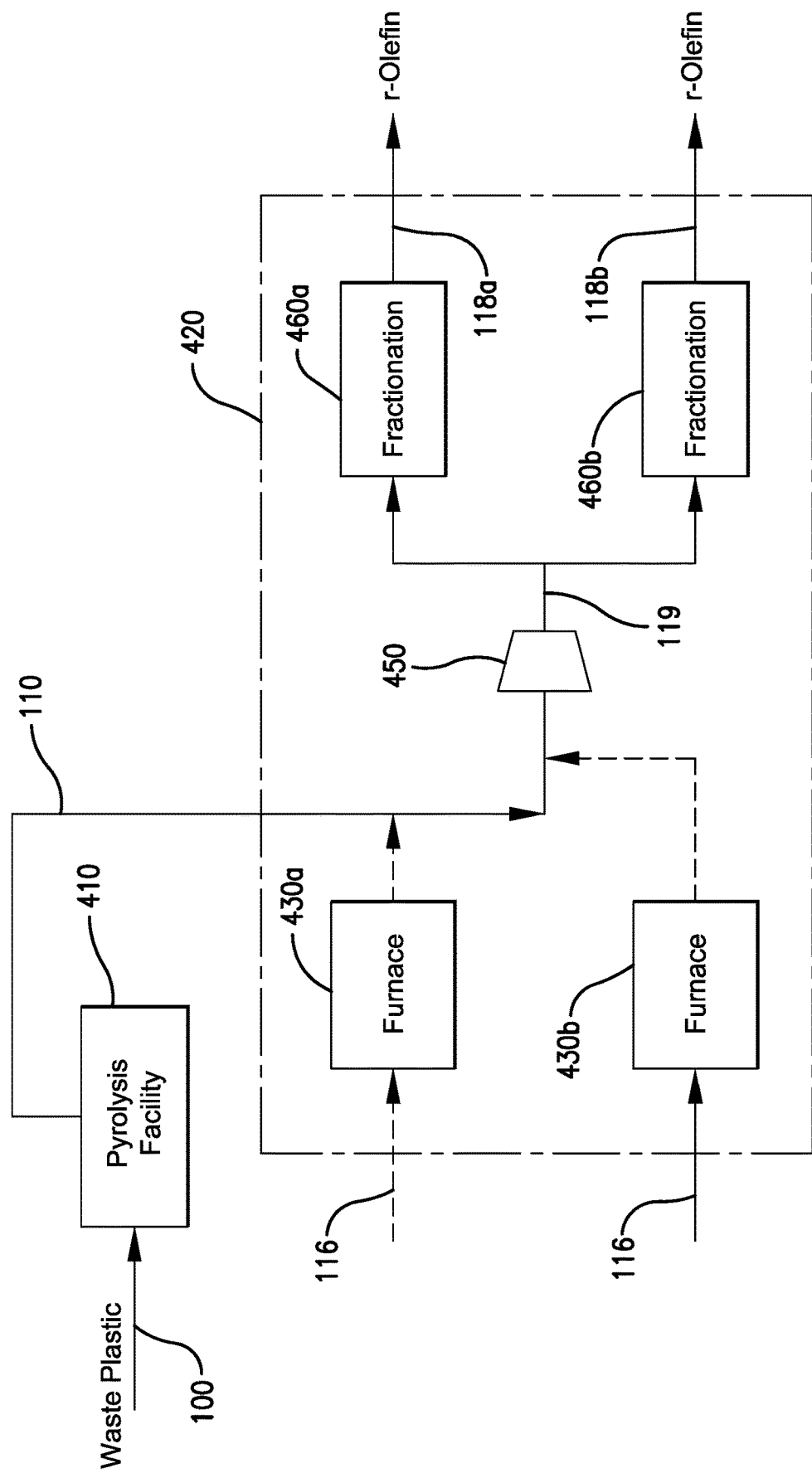
FIG. 8 depicts still another exemplary system for processing waste plastic that includes a pyrolysis facility and a cracker facility, particularly illustrating still further embodiments of an integration strategy.

As shown in FIG. 8, two or more cracker furnaces 430*a,b* (in the same or different cracker facilities) may share a common compressor 450, which can direct compressed olefin-containing stream 117 to one or more separation zones. In one embodiment or in combination with any of the mentioned embodiments when a r-pyrolysis gas stream 110 is introduced into the cracker facility, it may be added at a location upstream of the first stage of the compressor 450, and the compressed r-pyrolysis gas may be introduced into one or both of the separation zones in, for example, separate fractionation sections 460*a,b*. One or both of the cracker furnaces 430*a,b* may be idle, operational, or may be operational but at a reduced feed and/or product rate, as described in detail previously.

Figure 9:
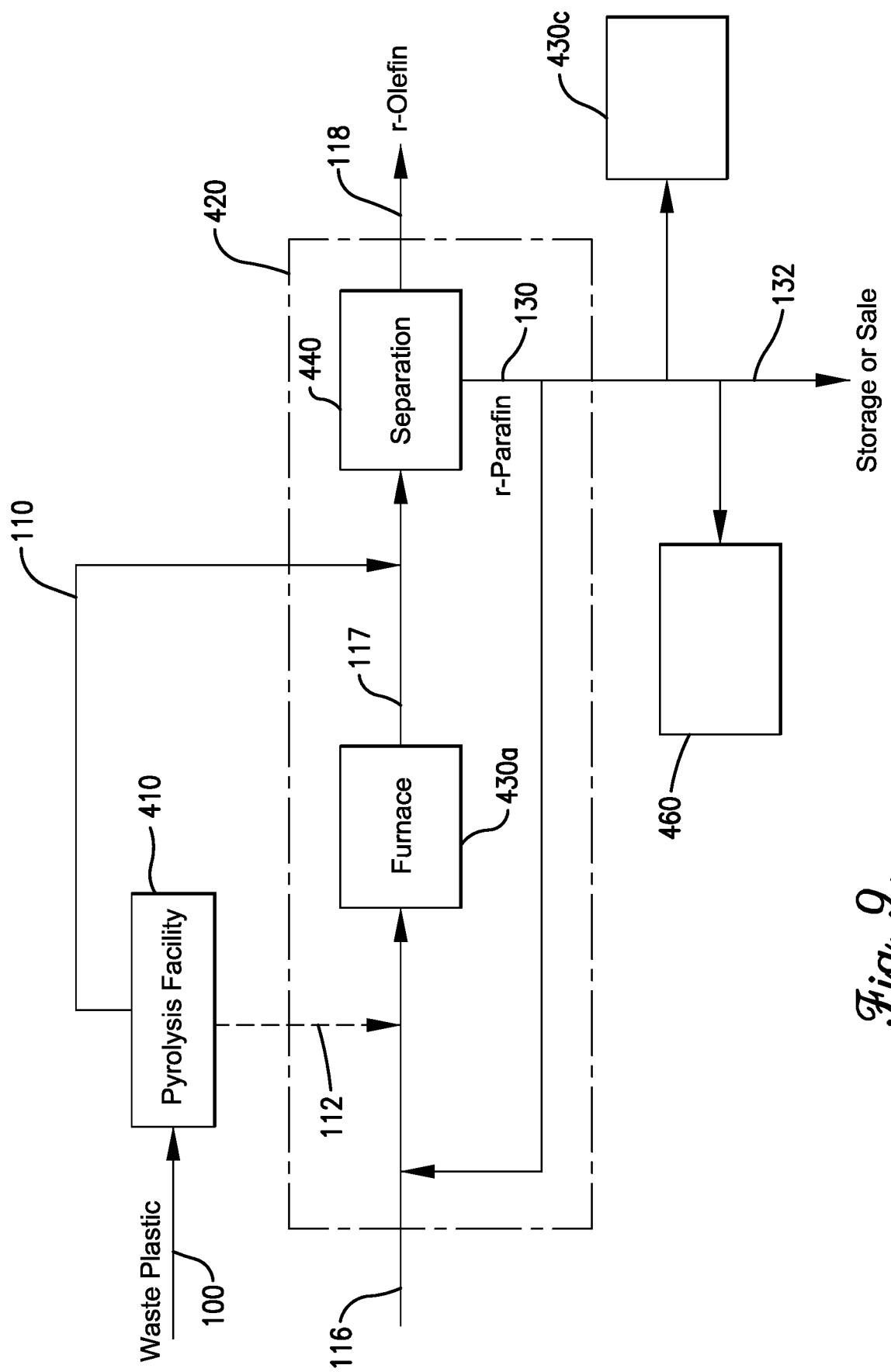
FIG. 9 depicts a further exemplary system for processing waste plastic that includes a pyrolysis facility and a cracker facility, particularly illustrating other embodiments of an integration strategy.

Turning now to FIG. 9, a system for processing waste plastic including a pyrolysis facility 410 and a cracker facility 420 is illustrated, particularly showing various aspects of the cracker facility. As shown in FIG. 9, a stream of r-pyrolysis gas 110 may be combined with an olefin-containing effluent stream 117 withdrawn a cracker furnace 430*a*, and the combined stream can then be introduced into a separation zone 440 of the cracker facility. In the separation zone 440, the stream can be separated to form one or more streams of olefin and one or more streams of paraffin. The recycle content olefin (r-olefin) may be removed from the cracker facility as a product or intermediate stream 118, while at least a portion of the recycle content paraffin (r-paraffin) stream 130 may be recycled to the inlet of at least one cracker furnace for use in the cracker feedstock. The cracker furnace may be the same cracker furnace 430*a* from which the olefin-containing stream was withdrawn, and/or it may be a separate cracker furnace, shown as 430*c* in FIG. 9. Additionally, or in the alternatively, at least a portion of the paraffin stream 130 may be sent to a downstream alkane processing facility 460 as a feedstock and/or for further storage or sale as shown by line 132.

In one embodiment or in combination with any of the mentioned embodiments, a stream of cracker feed 116 can be introduced into the cracker furnace 430. In one embodiment or in combination with any of the mentioned embodiments, the cracker feed stream 116 may comprise a predominantly C2 to C4 hydrocarbon containing composition, or a predominantly C5 to C22 hydrocarbon containing composition. As used herein, the term "predominantly C2 to C4 hydrocarbon," refers to a stream or composition containing at least 50 weight percent of C2 to C4 hydrocarbon components. Examples of specific types of C2 to C4 hydrocarbon streams or compositions include propane, ethane, butane, and LPG. In one embodiment or in combination with any of the mentioned embodiments, the cracker feed stream 116 may comprise at least 50, or at least 55, or at least 60, or at least 65, or at least 70, or at least 75, or at least 80, or at least 85, or at least 90, or at least 95, in each case wt. % based on the total weight of the feed, and/or not more than 100, or not more than 99, or not more than 95, or not more than 92, or not more than 90, or not more than 85, or not more than 80, or not more than 75, or not more than 70, or not more than 65, or not more than 60, in each case weight percent C2 to C4 hydrocarbons or linear alkanes, based on the total weight of the feed. The cracker feed stream 116 can comprise predominantly propane, predominantly ethane, predominantly butane, or a combination of two or more of these components.

In one embodiment or in combination with any of the mentioned embodiments, the cracker feed stream 116 may comprise a predominantly C5 to C22 hydrocarbon containing composition. As used herein, "predominantly C5 to C22 hydrocarbon" refers to a stream or composition comprising at least 50 weight percent of C5 to C22 hydrocarbon components.

Examples include gasoline, naphtha, middle distillates, diesel, kerosene. In one embodiment or in combination with any of the mentioned embodiments, the cracker feed stream 116 may comprise at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent and/or not more than 100, or not more than 99, or not more than 95, or not more than 92, or not more than 90, or not more than 85, or not more than 80, or not more than 75, or not more than 70, or not more than 65, or not more than 60, in each case weight percent C5 to C22, or C5 to C20 hydrocarbons, based on the total weight of the stream 116.

In one embodiment or in combination with any of the mentioned embodiments, the cracker feed stream 116 may have a C15 and heavier (C15+) content of at least 0.5, or at least 1, or at least 2, or at least 5, in each case weight percent and/or not more than 40, or not more than 35, or not more than 30, or not more than 25, or not more than 20, or not more than 18, or not more than 15, or not more than 12, or not more than 10, or not more than 5, or not more than 3, in each case weight percent, based on the total weight of the feed stream 116.

In one embodiment or in combination with any of the mentioned embodiments, the cracker feed stream 116 may have a C15 and heavier (C15+) content of at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case wt. % and/or not more than 100, or not more than 99, or not more than 95, or not more than 92, or not more than 90, or not more than 85, or not more than 80, or not more than 75, or not more than 70, or not more than 65, or not more than 60, in each case weight percent C5 to C22, or C5 to C20 hydrocarbons, based on the total weight of the stream 116. Examples of these types of hydrocarbons can include, but are not limited to, vacuum gas oil (VGO), hydrogenated vacuum gas oil (HVGO), and atmospheric gas oil (AGO).

In one embodiment or in combination with any of the mentioned embodiments, the 90% boiling point of the cracker feedstock or stream or composition can be at least 350° C., the 10% boiling point can be at least 60° C.; and the 50% boiling point can be in the range of from 95° C. to 200° C. In one embodiment or in combination with any of the mentioned embodiments, the 90% boiling point of the cracker feedstock stream 116 can be at least 150° C., the 10% boiling point can be at least 60° C., and the 50% boiling point can be in the range of from 80 to 145° C. The cracker feedstock stream 116 can have a 90% boiling point of at least 350° C., a 10% boiling point of at least 150° C., and a 50% boiling point in the range of from 220 to 280° C.

In one embodiment or in combination with any of the mentioned embodiments, the cracker furnace 430 may be a gas furnace. A gas furnace is a furnace having at least one coil which receives (or operated to receive or configured to receive), at the inlet of the coil at the entrance to the convection zone, a predominately vapor-phase feed (more than 50% of the weight of the feed is vapor) ("gas coil"). In one embodiment or in combination with any of the mentioned embodiments, the gas coil can receive a predominately C2-C4 feedstock, or a predominately a C2 and/or C3 feedstock to the inlet of the coil in the convection section, or alternatively, having at least one coil receiving more than 50 wt. % ethane and/or more than 50% propane and/or more than 50% LPG, or in any one of these cases at least 60 wt. %, or at least 70 wt. %, or at least 80 wt. %, based on the weight of the cracker feed to the coil, or alternatively based on the weight of the cracker feed to the convection zone.

The gas furnace may have more than one gas coil. In one embodiment or in combination with any of the mentioned embodiments, at least 25% of the coils, or at least 50% of the coils, or at least 60% of the coils, or all the coils in the convection zone or within a convection box of the furnace can be gas coils. The gas coil can receive, at the inlet of the coil at the entrance to the convection zone, a vapor-phase feed in which at least 60 wt. %, or at least 70 wt. %, or at least 80 wt. %, or at least 90 wt. %, or at least 95 wt. %, or at least 97 wt. %, or at least 98 wt. %, or at least 99 wt. %, or at least 99.5 wt. %, or at least 99.9 wt. % of the feed may be vapor.

In one embodiment or in combination with any of the mentioned embodiments, the furnace may be a split furnace. A split furnace is a type of gas furnace. A split furnace contains at least one gas coil and at least one liquid coil within the same furnace, or within the same convection zone, or within the same convection box. A liquid coil can be a coil which receives, at the inlet of coil at the entrance to the convection zone, a predominately liquid phase feed (more than 50% of the weight of the feed is liquid) ("liquid coil").

In one embodiment or in combination with any of the mentioned embodiments, the cracker can be a thermal gas cracker.

In one embodiment or in combination with any of the mentioned embodiments, the cracker feed may be thermally cracked a thermal steam gas cracker in the presence of steam. Steam cracking refers to the high-temperature cracking (decomposition) of hydrocarbons in the presence of steam.

When the cracker feed stream is combined with one or more other streams (such as, for example, r-pyoil), such a combination may occur upstream of, or within, the cracking furnace or within a single coil or tube. Alternatively, the r-pyoil containing feed stream and the cracker feed may be introduced separately into the furnace, and may pass through a portion, or all, of the furnace simultaneously while being isolated from one another by feeding into separate tubes within the same furnace (e.g., a split furnace).

Figure 7:
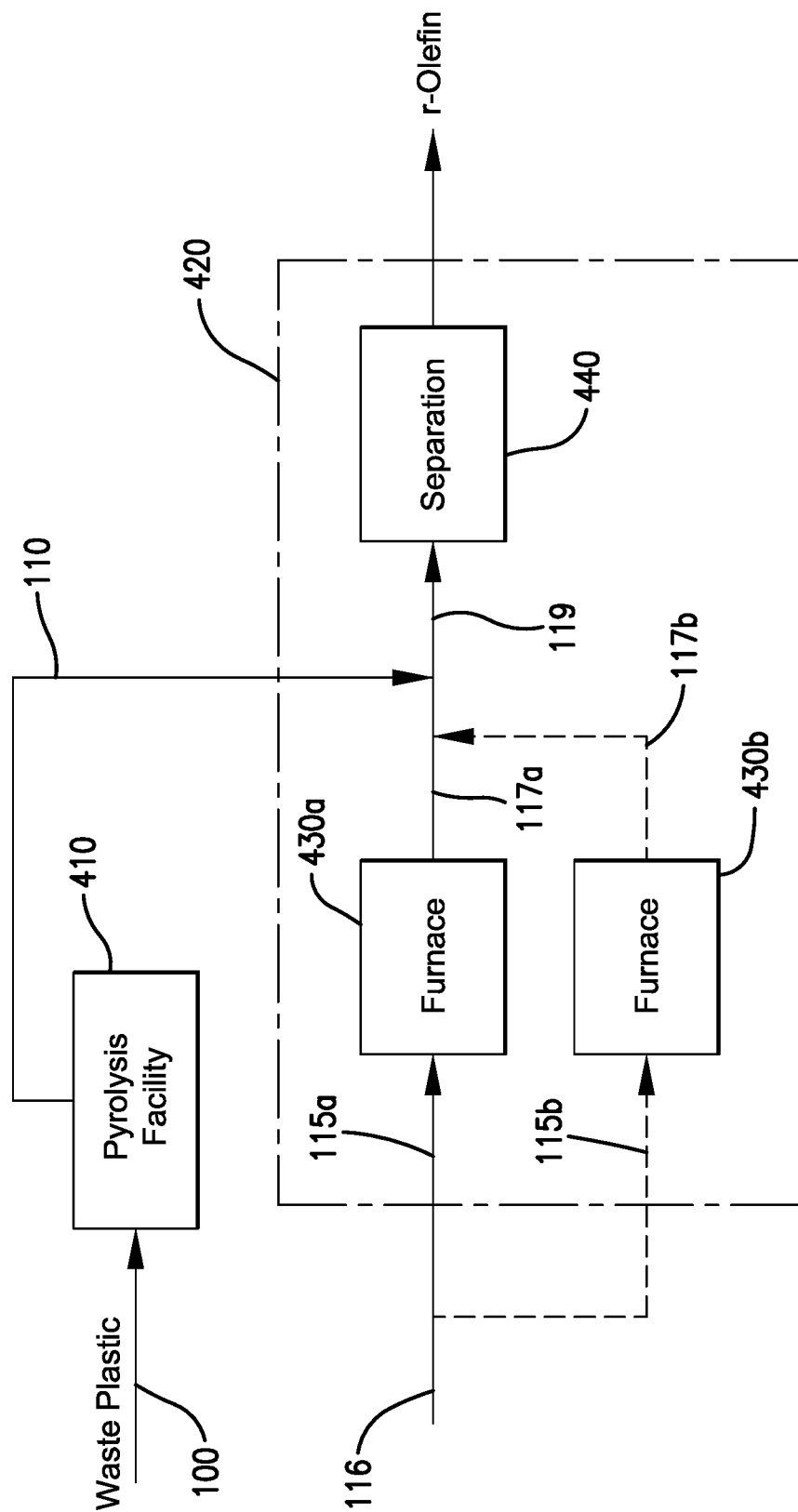
FIG. 7 depicts yet another exemplary system for processing waste plastic that includes a pyrolysis facility and a cracker facility, particularly illustrating further embodiments of an integration strategy.
Figure 10:
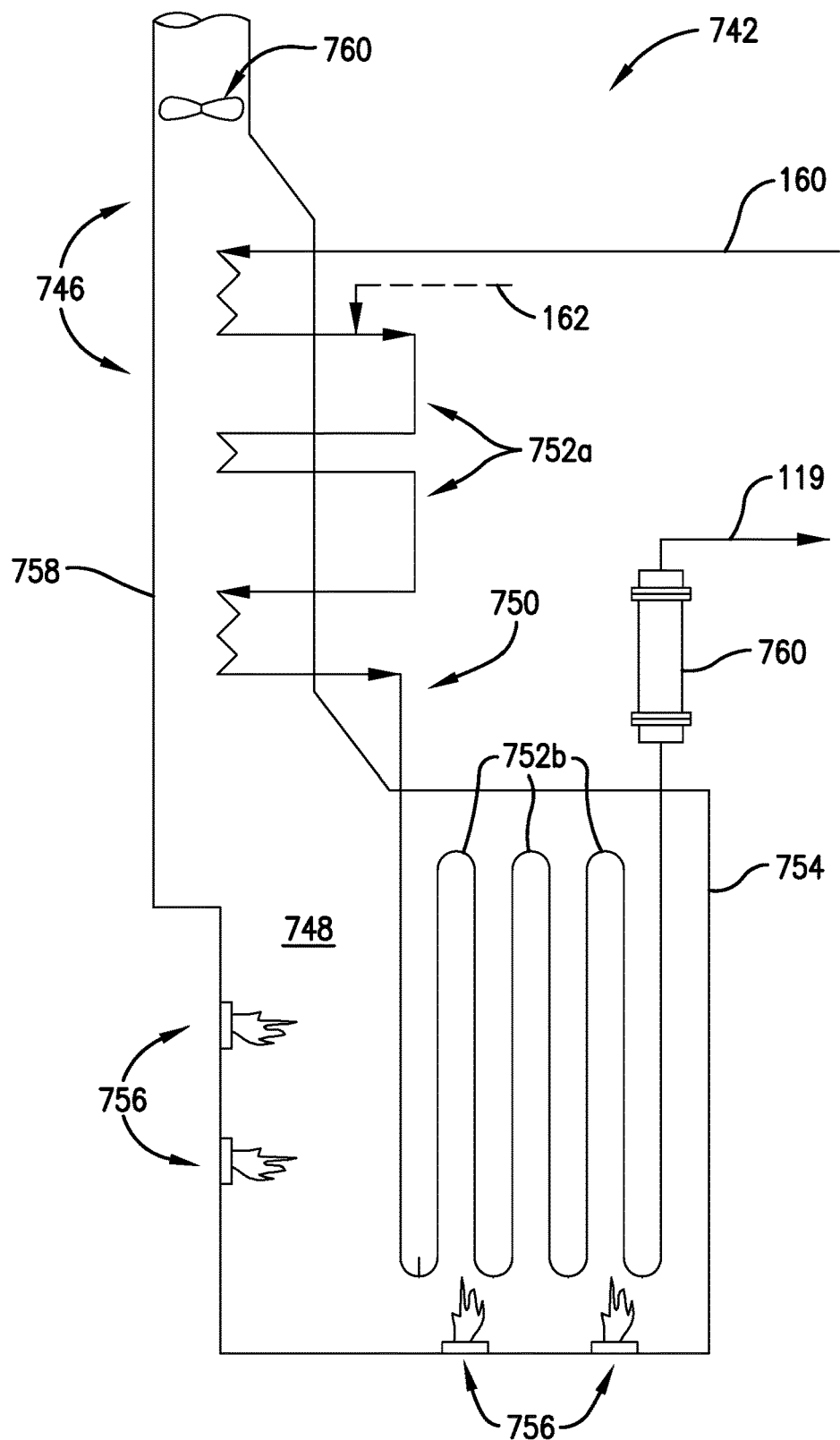
FIG. 10 provides a schematic diagram of a cracker furnace

Turning now to FIG. 10, a schematic diagram of a cracker furnace suitable for use in one or more embodiments is shown. As shown in FIG. 7, the cracking furnace can include a convection section 746, a radiant section 748, and a cross-over section 750 located between the convection section 746 and radiant section 748. The cross-over section 750 is located between and in fluid flow communication with the convection 746 section and radiant section 748.

The convection section 746 is the portion of the furnace 742 that receives heat from hot flue gases and includes a bank of tubes or coils 752a,b through which a cracker stream 160 passes. In the convection section 746, the cracker stream 160 is heated by convection from the hot flue gasses passing therethrough. Although shown in FIG. 10 as including horizontally-oriented convection section tubes 752a and vertically-oriented radiant section tubes 752b, it should be understood that the tubes 752 can be oriented in any suitable configuration. For example, in one embodiment or in combination with any of the mentioned embodiments, the convection section tubes 752a may be vertical. In one embodiment or in combination with any of the mentioned embodiments, the radiant section tubes 752b may be horizontal. Additionally, although shown as a single tube, the cracker furnace may comprise one or more tubes or coils 752 that may include at least one split, bend, U, elbow, or combinations thereof. When multiple tubes or coils are present, such may be arranged in parallel and/or in series.

The radiant section 748 is the section of the furnace 742 into which heat is transferred into the heater tubes primarily by radiation from the high-temperature gas. The radiant section 748 also includes a plurality of burners 756 for introducing heat into the lower portion of the furnace 742. The furnace 742 includes a fire box 754 which surrounds and houses the tubes 752b within the radiant section 748 and into which the burners 756 are oriented. The cross-over section 750 includes piping for connecting the convection section 746 and radiant section 748 and may transfer the heated cracker stream 160 from one section to the other within, or external to, the interior of the furnace.

As hot combustion gases ascend upwardly through the furnace stack, the gases may pass through the convection section 746, wherein at least a portion of the waste heat may be recovered and used to heat the cracker stream 116 passing through the convection section.

In one embodiment or in combination with any of the mentioned embodiments, the cracking furnace 742 may have a single convection (preheat) section and a single radiant section, while, in other embodiments, the furnace may include two or more radiant sections sharing a common convection section. At least one induced draft (I.D.) fan 760 near the stack (not shown) may control the flow of hot flue gas through the furnace 742 and thereby control its heating profile. Additionally, in one embodiment or in combination with any of the mentioned embodiments, one or more heat exchangers 760 may be used to cool the furnace effluent 119. In one or more embodiments (not shown), a liquid quench stream may be used in addition to, or alternatively with, the exchanger (e.g., transfer line heat exchanger or TLE) on the outlet of the furnace shown in FIG. 10 for cooling the cracked olefin-containing furnace effluent 119.

A cracker facility may have a single cracking furnace, or it can have at least 2, or at least 3, or at least 4, or at least 5, or at least 6, or at least 7, or at least 8 or more cracking furnaces operated in parallel. Any one or each furnace(s) may be gas cracker, or a liquid cracker, or a split furnace. In an embodiment or in combination with any embodiment mentioned herein or in combination with any of the mentioned embodiments, the furnace is a gas cracker receiving a cracker feed stream containing at least 50 wt. %, or at least 75 wt. %, or at least 85 wt. % or at least 90 wt. % ethane, propane, LPG, or a combination thereof through the furnace, or through at least one coil in a furnace, or through at least one tube in the furnace, based on the weight of all cracker feed to the furnace.

In one embodiment or in combination with any of the mentioned embodiments, the furnace can be a liquid or naphtha cracker receiving a cracker feed stream containing at least 50 wt. %, or at least 75 wt. %, or at least 85 wt. % liquid (when measured at 25° C. and 1 atm) hydrocarbons having a carbon number from C5-C22 through the furnace, or through at least one coil in a furnace, or through at least one tube in the furnace, based on the weight of all cracker feed to the furnace.

In one embodiment or in combination with any of the mentioned embodiments, the furnace may be a split furnace receiving a cracker feed stream containing at least 50 wt. %, or at least 75 wt. %, or at least 85 wt. % or at least 90 wt. % ethane, propane, LPG, or a combination thereof through the furnace, or through at least one coil in a furnace, or through at least one tube in the furnace, and receiving a cracker feed stream containing at least 0.5 wt. %, or at least 0.1 wt. %, or at least 1 wt. %, or at least 2 wt. %, or at least 5 wt. %, or at least 7 wt. %, or at least 10 wt. %, or at least 13 wt. %, or at least 15 wt. %, or at least 20 wt. % liquid and/or r-pyoil (when measured at 25° C. and 1 atm), each based on the weight of all cracker feed to the furnace.

When the cracker furnace feed comprises r-pyoil, the r-pyoil may be introduced into a cracking furnace or coil or tube of the furnace alone (e.g., in a stream comprising at least 85, or at least 90, or at least 95, or at least 99, or 100, in each case wt. % percent pyrolysis oil based on the weight of the cracker feed stream), or combined with one or more other cracker feed streams.

When introduced into a cracker furnace, coil, or tube with a non-recycle cracker feed stream, the r-pyoil may be present in an amount of at least 1, or at least 2, or at least 5, or at least 8, or at least 10, or at least 12, or at least 15, or at least 20, or at least 25, or at least 30, in each case wt. % and/or not more than 40, or not more than 35, or not more than 30, or not more than 25, or not more than 20, or not more than 15, or not more than 10, or not more than 8, or not more than 5, or not more than 2, in each case weight percent based on the total weight of the combined stream.

Thus, the other cracker feed streams may be present in the combined stream in an amount of at least 20, or at least 25, or at least 30, or at least 35, or at least 40, or at least 45, or at least 50, or at least 55, or at least 60, or at least 65, or at least 70, or at least 75, or at least 80, or at least 85, or at least 90, in each case weight percent and/or not more than 99, or not more than 95, or not more than 90, or not more than 85, or not more than 80, or not more than 75, or not more than 70, or not more than 65, or not more than 60, or not more than 55, or not more than 50, or not more than 45, or not more than 40, in each case weight percent based on the total weight of the combined stream. Unless otherwise noted herein, the properties of the cracker feed stream as described below apply to a cracker feed stream prior to (or absent) combination with the stream comprising r-pyoil, as well as to a combined cracker stream including both another cracker feed and a r-pyoil feed.

Turning back to FIG. 10, the cracker feed stream 160 may be introduced into a furnace coil 752 at or near the inlet of the convection section 746. The cracker feed stream 160 may then pass through at least a portion of the furnace coil 752a in the convection section 746, and dilution steam 162 may be added at some point in order to control the temperature and cracking severity in the radiant section 748.

The amount of steam added may depend on the furnace operating conditions, including feed type and desired product distribution, but can be added to achieve a steam-to-hydrocarbon ratio in the range of from 0.1 to 1.0, 0.15 to 0.9, 0.2 to 0.8, 0.3 to 0.75, or 0.4 to 0.6. The steam to hydrocarbon ratio may be at least 0.25:1, at least 0.27:1, at least 0.30:1, at least 0.32:1, at least 0.35:1, at least 0.37:1, at least 0.40:1, at least 0.42:1, at least 0.45:1, at least 0.47:1, at least 0.50:1, at least 0.52:1, at least 0.55:1, at least 0.57:1, at least 0.60:1, at least 0.62:1, at least 0.65:1 and/or not more than 0.80:1, not more than 0.75:1, not more than 0.72:1, not more than 0.70:1, not more than 0.67:1, not more than 0.65:1, not more than 0.62:1, not more than 0.60:1, not more than 0.57:1, not more than 0.55:1, not more than 0.52:1, not more than 0.50:1.

In one embodiment or in combination with any of the mentioned embodiments, the steam 162 may be produced using separate boiler feed water/steam tubes heated in the convection section of the same furnace (not shown in FIG. 10). Steam may be added to the cracker feed stream 160 (or any intermediate cracker feed stream within the furnace) when the cracker feed stream 160 has a vapor fraction of 0.60 to 0.95, or 0.65 to 0.90, or 0.70 to 0.90.

The heated cracker stream, which usually has a temperature of at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case ° C. and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case ° C., or in the range of from 500 to 710° C., 620 to 740° C., 560 to 670° C., or 510 to 650° C., may then pass from the convection section of the furnace to the radiant section via the cross-over section. The at least a portion of feed stream 160 (e.g., the r-pyoil, when used) may be added to the cracker stream at the cross-over section 750.

The cracker feed stream then passes through the radiant section 748, wherein the stream is thermally cracked to form lighter hydrocarbons, including olefins such as ethylene, propylene, and/or butadiene. The residence time of the cracker feed stream in the radiant section 748 can be at least 0.1, or at least 0.15, or at least 0.2, or at least 0.25, or at least 0.3, or at least 0.35, or at least 0.4, or at least 0.45, in each case seconds and/or not more than 2, or not more than 1.75, or not more than 1.5, or not more than 1.25, or not more than 1, or not more than 0.9, or not more than 0.8, or not more than 0.75, or not more than 0.7, or not more than 0.65, or not more than 0.6, or not more than 0.5, in each case seconds.

The temperature at the inlet of the furnace coil is at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case ° C. and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case ° C., or in the range of from 550 to 710° C., 560 to 680° C., or 590 to 650° C., or 580 to 750° C., 620 to 720° C., or 650 to 710° C.

The coil outlet temperature can be at least 640, or at least 650, or at least 660, or at least 670, or at least 680, or at least 690, or at least 700, or at least 720, or at least 730, or at least 740, or at least 750, or at least 760, or at least 770, or at least 780, or at least 790, or at least 800, or at least 810, or at least 820, in each case ° C. and/or not more than 1000, or not more than 990, or not more than 980, or not more than 970, or not more than 960, or not more than 950, or not more than 940, or not more than 930, or not more than 920, or not more than 910, or not more than 900, or not more than 890, or not more than 880, or not more than 875, or not more than 870, or not more than 860, or not more than 850, or not more than 840, or not more than 830, in each case ° C., in the range of from 730 to 900° C., 750 to 875° C., or 750 to 850° C.

In one embodiment or in combination with any of the mentioned embodiments, the mass velocity of the cracker stream through the radiant coil is in the range of 60 to 165 kilograms per second (kg/s) per square meter (m2) of cross-sectional area (kg/s/m2), 70 to 110 (kg/s/m2), or 80 to 100 (kg/s/m2). When steam is present, the mass velocity is based on the total flow of hydrocarbon and steam.

In one embodiment or in combination with any of the mentioned embodiments, the burners 756 in the radiant zone 748 provide an average heat flux into the coil in the range of from 60 to 160 kW/m2 or 70 to 145 kW/m2 or 75 to 130 kW/m2. The maximum (hottest) coil surface temperature is in the range of 1035 to 1150° C. or 1060 to 1180° C. The pressure at the inlet of the furnace coil in the radiant section 748 is in the range of 1.5 to 8 bar absolute (bara), or 2.5 to 7 bara, while the outlet pressure of the furnace coil 752b in the radiant section 748 is in the range of from 15 to 40 psia, or 15 to 30 psia. The pressure drop across the furnace coil 752b in the radiant section 748 can be from 1.5 to 5 bara, or 1.75 to 3.5 bara, or 1.5 to 3 bara, or 1.5 to 3.5 bara.

In one embodiment or in combination with any of the mentioned embodiments, the yield of olefin—ethylene, propylene, butadiene, or combinations thereof—can be at least 15, or at least 20, or at least 25, or at least 30, or at least 35, or at least 40, or at least 45, or at least 50, or at least 55, or at least 60, or at least 65, or at least 70, or at least 75, or at least 80, in each case percent. As used herein, the term "yield" refers to the mass of product produced from the feedstock/mass of feedstock×100%. The olefin-containing effluent stream 119 comprises at least about 30, or at least 40, or at least 50, or at least 60, or at least 70, or at least 75, or at least 80, or at least 85, or at least 90, or at least 95, or at least 97, or at least 99, in each case weight percent of ethylene, propylene, or ethylene and propylene, based on the total weight of the effluent stream.

In one embodiment or in combination with any of the mentioned embodiments, the olefin-containing effluent stream 119 can comprise at least 10, at least 15, at least 20, at least 25, at least 30, at least 35, at least 40, at least 45, at least 50, at least 55, at least 60, at least 65, at least 70, at least 75, at least 80, at least 85, or at least 90 weight percent of C2 to C4 olefins. The stream may comprise predominantly ethylene, predominantly propylene, or predominantly ethylene and propylene, based on the total weight of the olefin-containing stream. The weight ratio of ethylene-to-propylene in the olefin-containing effluent stream can be at least 0.2:1, at least 0.3:1, at least 0.4:1, at least 0.5:1, at least 0.6:1, at least 0.7:1, at least 0.8:1, at least 0.9:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, or at least 2:1 and/or not more than 3:1, 2.9:1, 2.8:1, 2.7:1, 2.5:1, 2.3:1, 2.2:1, 2.1:1, 2:1, 1.7:1, 1.5:1, or 1.25:1.

In one embodiment or in combination with any of the mentioned embodiments, the cracked olefin-containing effluent stream 119 may include relatively minor amounts of aromatics and other heavy components. For example, the olefin-containing effluent stream may include at least 0.5, at least 1, at least 2, or at least 2.5 weight percent and/or not more than about 20, not more than 19, not more than 18, not more than 17, not more than 16, not more than 15, not more than 14, not more than 13, not more than 12, not more than 11, not more than 10, not more than 9, not more than 8, not more than 7, not more than 6, not more than 5, not more than 4, not more than 3, not more than 2, or not more than 1 weight percent of aromatics, based on the total weight of the stream.

The olefin-containing effluent may have an olefin-to-aromatic ratio, by weight, of at least 1.25:1, at least 1.5:1, at least 2:1, at least 3.1, at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 21:1, at least 22:1, at least 23:1, at least 24:1, at least 25:1, at least 26:1, at least 27:1, at least 28:1, at least 29:1, or at least 30:1 and/or not more than 100:1, not more than 90:1, not more than 85:1, not more than 80:1, not more than 75:1, not more than 70:1, not more than 65:1, not more than 60:1, not more than 55:1, not more than 50:1, not more than 45:1, not more than 40:1, not more than 35:1, not more than 30:1, not more than 25:1, not more than 20:1, not more than 15:1, not more than 10:1, not more than 5:1, not more than 4:1, or not more than 3:1. As used herein, "olefin-to-aromatic ratio" is the ratio of total weight of C2 and C3 olefins to the total weight of aromatics, as defined previously. In one embodiment or in combination with any of the mentioned embodiments, the effluent stream can have an olefin-to-aromatic ratio of at least 2.5:1, at least 2.75:1, at least 3.5:1, at least 4.5:1, at least 5.5:1, at least 6.5:1, at least 7.5:1, at least 8.5:1, at least 9.5:1, at least 10.5:1, at least 11.5:1, at least 12.5:1, or at least 13:5:1.

Additionally, or in the alternative, the olefin-containing effluent stream can have an olefin-to-C6+ ratio of at least 1.5:1, at least 1.75:1, at least 2:1, at least 2.25:1, at least 2.5:1, at least 2.75:1, at least 3:1, at least 3.25:1, at least 3.5:1, at least 3.75:1, at least 4:1, at least 4.25:1, at least 4.5:1, at least 4.75:1, at least 5:1, at least 5.25:1, at least 5.5:1, at least 5.75:1, at least 6:1, at least 6.25:1, at least 6.5:1, at least 6.75:1, at least 7:1, at least 7.25:1, at least 7.5:1, at least 7.75:1, at least 8:1, at least 8.25:1, at least 8.5:1, at least 8.75:1, or at least 9:1.

The olefin-containing stream may also include trace amounts of aromatics. For example, the composition may have a benzene content of at least 0.25, at least 0.3, at least 0.4, at least 0.5 weight percent and/or not more than about 2, 1.7, 1.6, 1.5 weight percent. Additionally, or in the alternative, the composition may have a toluene content of at least 0.005, at least 0.010, at least 0.015, or at least 0.020 and/or not more than 0.5, not more than 0.4, not more than 0.3, or not more than 0.2 weight percent. Both percentages are based on the total weight of the composition. Alternatively, or in addition, the effluent can have a benzene content of at least 0.2, at least 0.3, at least 0.4, at least 0.5, or at least 0.55 and/or not more than about 2, 1.9, 1.8, 1.7, or 1.6 weight percent and/or a toluene content of at least 0.01, at least 0.05, or at least 0.10 and/or not more than 0.5, not more than 0.4, not more than 0.3, or not more than 0.2 weight percent.

In one embodiment or in combination with any of the mentioned embodiments, the olefin-containing effluent stream may comprise acetylene. The amount of acetylene can be at least 2000 ppm, at least 5000 ppm, at least 8000 ppm, or at least 10,000 ppm based on the total weight of the effluent stream from the furnace. It may also be not more than 50,000 ppm, not more than 40,000 ppm, not more than 30,000 ppm, or not more than 25,000 ppm.

In one embodiment or in combination with any of the mentioned embodiments, the olefin-containing effluent stream may comprise methyl acetylene and propadiene (MAPD). The amount of MAPD may be at least 2 ppm, at least 5 ppm, at least 10 ppm, at least 20 pm, at least 50 ppm, at least 100 ppm, at least 500 ppm, at least 1000 ppm, at least 5000 ppm, or at least 10,000 ppm, based on the total weight of the effluent stream. It may also be not more than 50,000 ppm, not more than 40,000 ppm, or not more than 30,000 ppm.

In some embodiments, the separation zone of the cracker facility may be divided into a treatment section and a fractionation section. As used herein, the term "treatment section" is the portion of the separation zone of the cracker facility used to cool, treat, and compress the olefin-containing stream (which may include an olefin-containing effluent from the cracker furnace) in preparation for its fractionation in the fractionation section. The treatment section may extend from the furnace outlet to the inlet of the first fractionation column of the fractionation zone.

As used herein, the term "fractionation" refers to the separation of mixtures into their pure or purified components. Examples of equipment used to accomplish fractionation can include, but are not limited to, distillation columns, flash columns, extraction vessels, stripper columns, rectification columns, membrane units, adsorption columns or vessels, absorption columns or vessels, and combinations thereof. In the cracker facility, the fractionation section may be configured to separate an olefin-containing stream removed from the treatment section to form a variety of purified olefin and/or alkane streams. In one embodiment or in combination with any of the mentioned embodiments, the fractionation section may be configured to separate a stream comprising an olefin-containing effluent from the cracker furnace and/or a stream of r-pyrolysis gas.

Figure 11A:
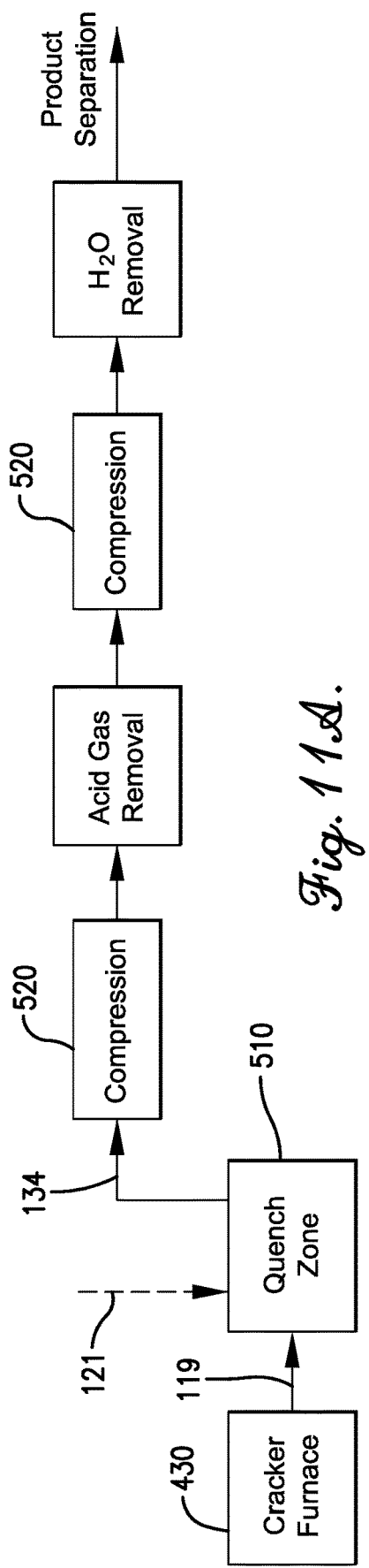
FIG. 11a depicts an exemplary system for pre-treating a stream of furnace effluent from a cracking facility prior to separation.
Figure 11B:
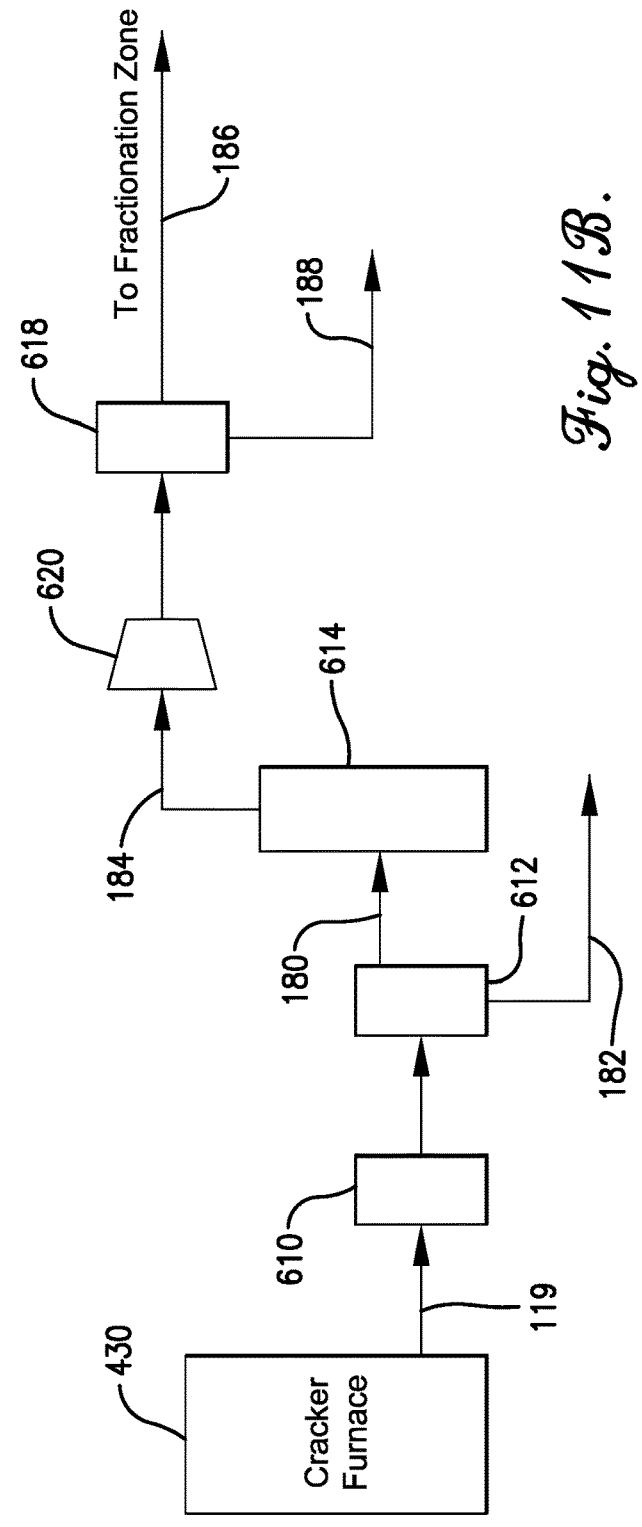

Turning now to FIG. 11a, a block diagram illustrating the main elements of a treatment section of the separation zone in the cracker facility are shown. Additionally, FIG. 11b provides a schematic diagram of several of the steps in the quench and compression zones depicted in FIG. 11a.

Turning first to FIG. 11a, when present, the olefin-containing effluent stream 119 from the cracking furnace 430 can be cooled rapidly (e.g., quenched) in order to prevent production of large amounts of undesirable byproducts and to minimize fouling in downstream equipment. In one embodiment or in combination with any of the mentioned embodiments, the temperature of the effluent stream 119 from the furnace can be reduced by 35 to 485° C., 35 to 375° C., or 90 to 550° C. to a temperature of 500 to 760° C. The cooling step can be performed immediately after the effluent stream leaves the furnace 430 such as, for example, within 1 to 30, 5 to 20, or 5 to 15 milliseconds. Overall, the cooling step can reduce the temperature of the olefin-containing effluent stream 119 by at least 25, at least 50, at least 75, at least 100, at least 125, at least 150, at least 175, at least 200, at least 225, or at least 250° C. and/or not more than 700, not more than 650, not more than 600, not more than 550, not more than 500, not more than 450, or not more than 400° C.

In one embodiment or in combination with any of the mentioned embodiments, the quenching step can be performed via indirect heat exchange with high-pressure water or steam in a heat exchanger, while, in other embodiments, the quench step is carried out by directly contacting the effluent with a quench liquid in stream 121 in a quench tower (separator with or without column internals). The temperature of the quench liquid stream 121 can be at least 65, or at least 80, or at least 90, or at least 100, in each case ° C. and/or not more than 210, or not more than 180, or not more than 165, or not more than 150, or not more than 135, in each case ° C.

When a quench liquid stream 121 is used, the contacting may occur in a quench tower of a quench zone 510 and a liquid stream may be removed from the quench tower comprising gasoline and other similar boiling-range hydrocarbon components. In some cases, quench liquid stream 121 may be used in quench zone 510 when the cracker feed is predominantly liquid, and a heat exchanger (not shown) may be used in the quench zone 510 when the cracker feed is predominantly vapor.

As shown in FIG. 11b, in one embodiment or in combination with any of the mentioned embodiments, the quench zone 510 may include at least one fractionator 612 (shown in FIG. 11b) for separating out at least a portion of the liquid phase of cooled olefin-containing effluent removed from the transfer line exchanger (TLE) 610 at the furnace outlet. The fractionator 612 may be configured to separate the partially cooled olefin-containing effluent into an overhead vapor stream 180 enriched in C6 and lighter, in C7 and lighter, or in C8 and lighter components, and a bottoms liquid stream 182 enriched in C7 and heavier, in C8 and heavier, or in C9 and heavier components (referred to in FIG. 11b as py-tar). The resulting overhead vapor stream 180 may then be introduced into a quench tower 614, wherein the stream may be further cooled via contact with a quench liquid, as discussed previously. The bottoms liquid stream 182 from the fractionator 612, also referred to as py-tar, may be sent for further processing, transportation, storage, and/or use.

Referring again to FIGS. 11a and 11b, the resulting cooled effluent stream from the quench tower 614 can then be separated in a knock out drum (not shown in FIGS. 11a and 11b), so that the resulting vapor may be compressed in a gas compressor 620 having, for example, between 1 and 10, 2 and 8, or 2 and 6 compression stages, each with optional inter-stage cooling and liquid removal. The pressure of the gas stream at the outlet of the first set of compression stages is in the range of from 19 to 59 psig (1.3 to 4.0 barg), 21 to 49 psig (1.4 to 3.3 barg), or 24 to 46 psig (1.6 to 2.7 barg).

In one embodiment or in combination with any of the mentioned embodiments, the system may further include at least one additional separator (not shown in FIG. 11b) for further separating at least a portion of the heavy component-containing liquids stream removed from one or more knock out drums located before or in between the compression stages of the gas compressor (shown in FIG. 11b as a single knock out drum 618). Although shown in FIG. 11b as including only a single compression stage and knock out drum, it should be understood that the compression system includes multiple compression stages with knock out drums before each stage or set of stages. The knockout drum can be upstream of one or more of the first, second, third, fourth, fifth, sixth, or seventh compression stage of the gas compressor 620. The liquids stream from the knockout drum or drums 188 may comprise condensate such as aqueous condensate and/or organic condensate.

The liquid stream 188, when present, from each of these knock out drums can be combined with one another (and, optionally, with all or a portion of the bottoms stream from the gasoline fractionator in stream 182) to form a combined stream. Alternatively, the liquid stream 188 may originate from a single vessel.

Additionally, all or a portion of the heavy fraction removed from the vapor-liquid separator in line 182 may be further separated in another separator (not shown in FIG. 11*b*) into at least an overhead vapor stream and a bottoms liquid stream. The liquid fraction removed from the bottom of the separator 612 may comprise predominantly C4 and heavier, C5 and heavier, or C6 and heavier hydrocarbons and can include or be used to form a recycle content gasoline composition (r-pyrolysis gasoline).

In some cases, the liquid stream in line 182 can comprise r-pyrolysis gasoline in an amount of at least 1, at least 2, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95 weight percent and/or not more than 99, not more than 97, not more than 95, not more than 90, not more than 85, not more than 80, not more than 75, not more than 70, not more than 65, not more than 60, not more than 55, not more than 50, not more than 45, not more than 40, or not more than 35 weight percent, based on the total weight of the stream 182. In an embodiment or in combination with any embodiment mentioned herein, at least a portion of the r-pyrolysis gasoline stream 182 may be further separated into a light fraction and heavy fraction in yet another fractionation column (not shown in FIG. 11*b*), and one or both may be used in downstream processes, such as, for example, in forming resins for use in adhesives, fuel, polymers, plasticizers, or combinations thereof.

Figure 12:
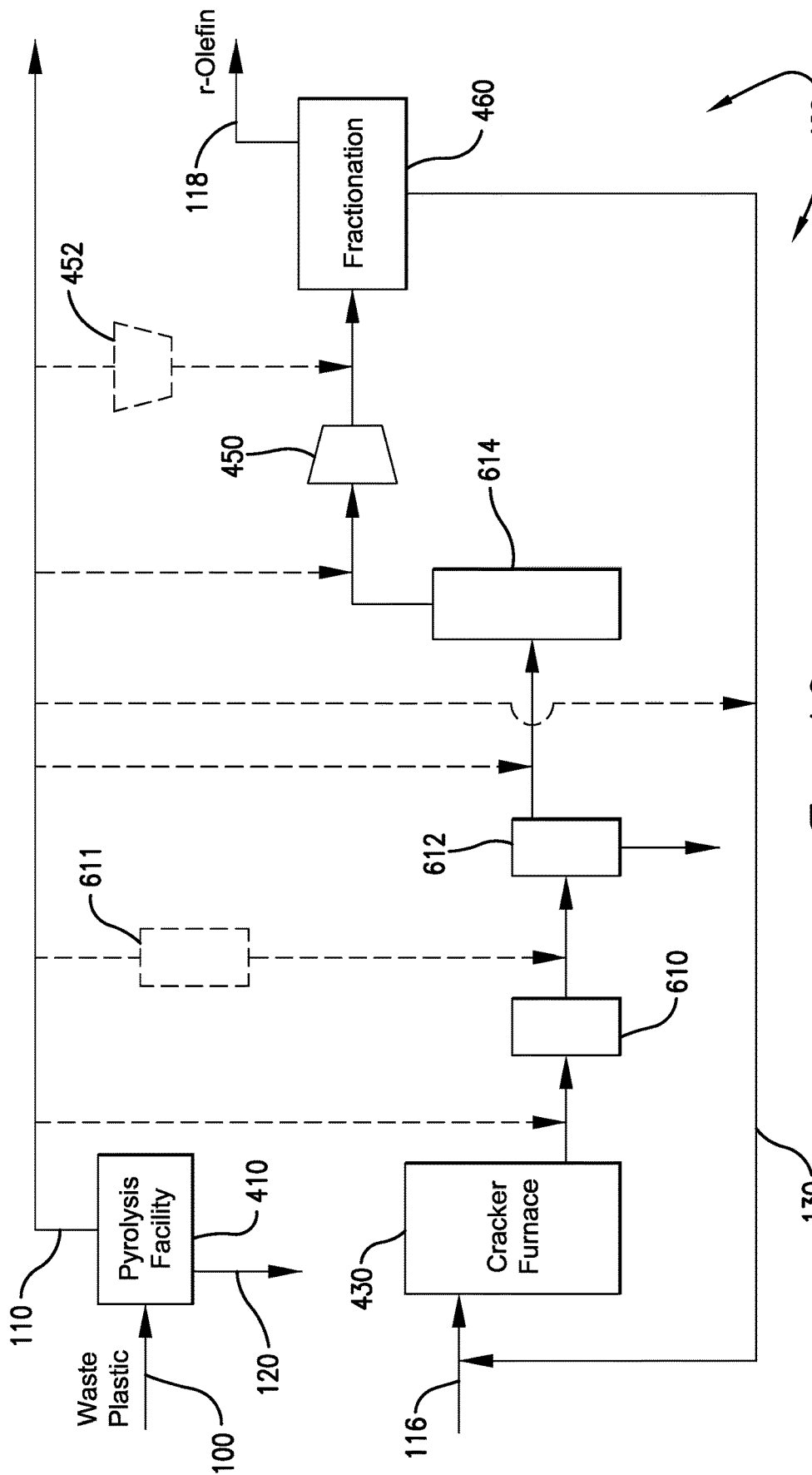
FIG. 12 depicts exemplary locations for introducing pyrolysis gas into a cracker facility downstream of a cracking furnace.

Turning now to FIG. 12, one embodiment of a chemical recycling facility including a pyrolysis facility 410 and a cracker facility 420 is provided, particularly illustrating various locations downstream of the cracker furnace 430 where a stream comprising r-pyrolysis gas 110 could be introduced into the cracker facility 420. In general, as shown in FIG. 12, the r-pyrolysis gas stream 110 may be introduced into the cracker facility at a location downstream of the cracker furnace outlet. In one embodiment or in combination with any of the mentioned embodiments, the location may be upstream of the fractionation section (e.g., upstream of the inlet to the first vessel or column in the fractionation section).

As shown in FIG. 12, a stream comprising waste plastic 100 can be introduced into a pyrolysis facility 410, wherein it may be pyrolyzed to form a stream of r-pyrolysis gas 110 and a stream of r-pyoil 112. The pyrolysis facility 410 can be any pyrolysis facility suitable for processing waste plastic or streams derived from waste plastic and can include one or more of the features or properties described herein.

In some embodiments, the pyrolysis facility 410 may be part of a larger chemical recycling facility that can include one or more upstream facilities. For example, the larger chemical recycling facility may be configured to accept mixed plastic waste, which may be sorted in a pre-processing facility to provide a stream of PET-enriched waste plastic and a stream of PO-enriched waste plastic. At least a portion of the mixed plastic waste, the PET-enriched waste plastic, and/or the PO-enriched plastic may be introduced into the pyrolysis facility 410 in or as feed stream 100.

In one embodiment or in combination with any of the mentioned embodiments, the PET-enriched stream is enriched in concentration of PET relative to the concentration of PET in the MPW stream, or the PET-depleted stream, or both, on an undiluted solids dry basis. For example, if the PET-enriched stream is diluted with liquid or other solids after separation, the enrichment would be on the basis of a concentration in the undiluted PET-enriched stream, and on a dry basis. In one embodiment or in combination with any of the mentioned embodiments, the PET-enriched stream has a percent PET enrichment relative to the MPW stream, the PET-depleted stream, or both that is at least 10%, at least 20, at least 40, at least 50, at least 60, at least 80, at least 100, at least 125, at least 150, at least 175, at least 200, at least 225, at least 250, at least 300, at least 350, at least 400, at least 500, at least 600, at least 700, at least 800, at least 900, or at least 1000% as determined by the formula:

$$\% \ PETenrichment = \frac{PETe - PETm}{PETm} \times 100$$

and $$\% \ PETenrichment = \frac{PETe - PETd}{PETd} \times 100$$

where PETe is the concentration of PET in the PET-enriched stream on an undiluted dry weight basis; and PETm is the concentration of PET in the MPW stream on a dry weight basis, and PETd is the concentration of PET in the PET-depleted stream on a dry weight basis, In one embodiment or in combination with any of the mentioned embodiments, the PET-enriched stream is also enriched in halogens, such as fluorine (F), chlorine (Cl), bromine (Br), iodine (I), and astatine (At), and/or halogen-containing compounds, such as PVC, relative to the concentration of halogens in the MPW stream, or the PET-depleted stream, or both In one embodiment or in combination with any of the mentioned embodiments, the PET-enriched stream has a percent PVC enrichment relative to the MPW stream that is at least 1%, at least 3, at least 5, at least 7, at least 10, at least 15, at least 20, at least 40, at least 50, at least 60, at least 80, at least 100, at least 125, at least 150, at least 175, at least 200, at least 225, at least 250, at least 300, at least 350, at least 400, at least 500, % as determined by the formula:

$$\% \ PVCenrichment = \frac{PVCe - PVCm}{PVCm} \times 100$$

and $$\% \ PVCenrichment = \frac{PVCe - PVCd}{PVCd} \times 100$$

where PVCe is the concentration of PVC in the PET-enriched stream on an undiluted dry weight basis; and PVCm is the concentration of PVC in the MPW stream on an undiluted dry weight basis, and where PVCd is the concentration of PVC in the PET-depleted stream on an undiluted dry weight basis; and Due to the separation of polyolefins from the PET, the PET-depleted stream is enriched in polyolefins relative to the concentration of polyolefins in the MPW feed, or the PET-enriched stream, or both, on an undiluted solids dry basis. In one embodiment or in combination with any of the mentioned embodiments, the PET-depleted stream has a percent polyolefin enrichment relative to the MPW stream or relative to the PET-enriched stream or both that is at least 10%, at least 20, at least 40, at least 50, at least 60, at least 80, at least 100, at least 125, at least 150, at least 175, at least 200, at least 225, at least 250, at least 300, at least 350, at least 400, at least 500, at least 600, at least 700, at least 800, at least 900, or at least 1000% as determined by the formula:

$$\% \, POenrichment = \frac{POd - POm}{POm} \times 100$$

and $$\% \, POenrichment = \frac{POd - POe}{POe} \times 100$$

where POd is the concentration of polyolefins in the PET-depleted stream on an undiluted dry weight basis; and POm is the concentration of PO in the MPW stream on a dry weight basis, and POe is the concentration of PO in the PET-enriched stream.

In one embodiment or in combination with any other embodiments, the PET-depleted stream is also depleted in halogens, such as fluorine (F), chlorine (Cl), bromine (Br), iodine (I), and astatine (At), and/or halogen-containing compounds, such as PVC, relative to the concentration of halogens in the MPW stream, the PET-enriched stream, or both. In one embodiment or in combination with any of the mentioned embodiments, the PET-depleted stream has a percent PVC depletion, relative to the MPW stream or the PET-enriched stream, that is at least 1%, at least 3, at least 5, at least 7, at least 10, at least 15, at least 20, at least 25, at least 30, at least 35, at least 40, at least 50, at least 60, at least 65, at least 70, at least 75, at least 80, at least 85, at least 90% as determined by the formula:

$$\% \, PVCdepeltion = \frac{PVCm - PVCd}{PVCm} \times 100$$

and $$\% \, PVCdepletion = \frac{PVCe - PVCd}{PVCe} \times 100$$

where PVCm is the concentration of PVC in the MPW stream on an undiluted dry weight basis;

PVCd is the concentration of PVC in the PET-depleted stream on an undiluted dry weight basis; and PVCe is the concentration of PVC in the PET-enriched stream on an undiluted dry weight.

In one embodiment or in combination with any other embodiments, the PET-depleted stream is also depleted in PET, relative to the concentration of PET in the MPW stream, the PET-enriched stream, or both. In one embodiment or in combination with any of the mentioned embodiments, the PET-depleted stream has a percent PET depletion, relative to the MPW stream or the PET-enriched stream, that is at least 1%, at least 3, at least 5, at least 7, at least 10, at least 15, at least 20, at least 25, at least 30, at least 35, at least 40, at least 50, at least 60, at least 65, at least 70, at least 75, at least 80, at least 85, at least 90% as determined by the formula:

$$\% \, PETdepeltion = \frac{PETm - PETd}{PETm} \times 100$$

and $$\% \, PETdepletion = \frac{PETe - PETd}{PETe} \times 1.00$$

where PETm is the concentration of PET in the MPW stream on an undiluted dry weight basis;

PETd is the concentration of PET in the PET-depleted stream on an undiluted dry weight basis; and PETe is the concentration of PET in the PET-enriched stream on an undiluted dry weight.

In one embodiment or in combination with any of the mentioned embodiments, the PET-enriched stream 20 is depleted in nylons, relative to the PET-depleted stream 30. The PET-enriched stream 20 can be depleted in nylon atoms by at least 10%, or at least 25%, or at least 40%, or at least 50%, or at least 60%, or at least 70%, or at least 80%, or at least 85%, or at least 90%, or at least 95%, or at least 97%, or at least 98, in each case relative to the nylon atom concentration in the PET depleted stream 30, calculated on the basis of weight percent of nitrogen atoms in the individual streams. The sampling method can include taking a random sample from each stream, optionally taking 2 samples from each stream each 24 hour period for two weeks, and dried to a moisture content of less than 10 wt. %. The formula to carry out such a calculation is as set forth in Formula 1:

$$\% \text{ nitrogen atom depletion in } ePETstream = \frac{wt. \, \% \, NdPET - wt \, \% \, NePET}{wtwt \, \% \, NdPET} \times 100$$

where:

wt % N is weight percent of nylon atoms in a stream dPET is the PET depleted stream and ePET is the PET enriched stream The PET-enriched stream 20 can be depleted in the concentration of nylon atoms, relative to the MPW 10 stream, in the same amounts as stated above using the same formula, substituting wt % NMPW (weight percent of nylon atoms in the MPW stream) for the wt % NePET in Formula 1.

In one embodiment or in combination with any of the mentioned embodiments, the PET-depleted stream 30 is enriched in the concentration of nylon atoms, relative to the PET-enriched stream 20. The PET-depleted stream 30 can be enriched in concentration of nylon atoms by at least 10%, or at least 25%, or at least 50%, or at least 75%, or at least 100%, or at least 150%, or at least 200%, or at least 250%, or at least 300%, or at least 350%, or at least 400%, or at least 450%, or at least 500%, or at least 600%, or at least 700%, or at least 800%, or at least 1000%, in each case relative to the nylon atom concentration in the PET-enriched stream 20, calculated on the basis of weight percent of nitrogen atoms in the individual streams. The sampling method can include taking a random sample from each stream, optionally taking 2 samples from each stream each 24 hour period for two weeks. The formula to carry out such a calculation is according to Formula 2:

$$\% \, Nenrichment \text{ in } dPETstream = \frac{wt. \, \% \, NdPET - wt \, \% \, NePET}{wtwt \, \% \, NePET} \times 100$$

where:

wt % N is weight percent of nylon atoms in a stream dPET is the PET depleted stream and ePET is the PET enriched stream The PET-depleted stream 30 can be enriched in the concentration of nylon atoms, relative to the MPW 10 stream, at least 10%, or at least 25%, or at least 40%, or at least 50%, or at least 60%, or at least 70%, or at least 80%, or at least 85%, or at least 90%, in each case relative to the nylon atom concentration in the MPW stream 10, using the same formula 2, substituting wt % NMPW (weight percent of nylon atoms in the MPW stream) for the wt % NePET in Formula 2.

The percentage enrichment or depletion in any of the above embodiments can be an average over 1 week, or over 3 days, or over 1 day, and the measurements can be conducted to reasonably correlate the samples taken at the exits of the process to MPW bulk from which the sample of MPW is taking into account the residence time of the MPW to flow from entry to exit. For example, if the average residence time of the MPW is 2 minutes, then the outlet sample would be taken two minutes after the input sample, so that the sample correlate to one another.

In one embodiment or in combination with any of the mentioned embodiments, at least a portion of the PET-enriched waste plastic and/or at least a portion of the PO-enriched waste plastic may be sent to another chemical recycling facility and one or more streams from that chemical recycling facility may be introduced into the pyrolysis facility as or with the feed. Examples of other chemical recycling facilities can include, but are not limited to, solvolysis facilities, partial oxidation (PDX) gasification facilities, solidification facilities, and combinations thereof.

Additionally, or in the alternative, at least one stream from the pyrolysis facility 410 may be introduced into one or more of the solvolysis facilities, partial oxidation (PDX) gasification facilities, and solidification facilities as or as part of the feed to that facility. The stream introduced into one or more of these facilities can comprise r-pyoil, r-pyrolysis gas, or combinations thereof.

Turning back to FIG. 12, a stream of r-pyrolysis gas 110 can be introduced into one or more locations in a cracker facility 420. In one embodiment or in combination with any of the mentioned embodiments, at least a portion of the r-pyrolysis gas stream 110 can be introduced into a location within the cracker facility 420 that is upstream of a compressor 450 within the treatment section. When introduced upstream of the compressor 450, the r-pyrolysis gas may optionally be combined with an olefin-containing effluent stream withdrawn from the cracker furnace 430. The combined stream may be introduced into a compressor, a heat exchanger, a vessel such as a caustic scrubber or combinations thereof.

In one embodiment or in combination with any of the mentioned embodiments, the compressor 450 in the treatment section of the pyrolysis facility can be a multi-stage compressor having, for example, at least 2, at least 3, at least 4, at least 5, at least 6, at least 7, at least 8, at least 9, or at least 10 stages and/or not more than 15, not more than 14, not more than 13, not more than 12, not more than 11, not more than 10, not more than 9, not more than 8, not more than 7, not more than 6, or not more than 5 compression stages.

At least a portion of the r-pyrolysis gas stream 110 can be introduced at a location upstream of one or more compression stages and/or downstream of at least one compression stage. In one embodiment or in combination with any of the mentioned embodiments, at least a portion of the r-pyrolysis gas stream 110 may be introduced at a location upstream of the last stage of the compressor. In one embodiment or in combination with any of the mentioned embodiments, at least a portion of the r-pyrolysis gas stream can be introduced at a location between stages 1-3, at a location between stages 3-5, and/or at a location between stages 5-7 of a multi-stage compressor. In one or more other embodiments, at least a portion of the r-pyrolysis gas stream 110 may be introduced at a location downstream of the outlet of the compressor 450 and, optionally, may be compressed in a separate compressor 452 prior to being introduced into the cracker facility.

In one embodiment or in combination with any of the mentioned embodiments, at least a portion of the r-pyrolysis gas stream 110 can be introduced into a location downstream of a heat exchanger 610 and/or downstream of at least one fractionator or vessel. For example, at least a portion of the r-pyrolysis gas can be introduced upstream of the quench column 614 and/or gasoline fractionator 612, while, in other embodiments, at least a portion of the r-pyrolysis gas can be introduced downstream of the quench column 614 and/or gasoline fractionator 612.

In one embodiment or in combination with any of the mentioned embodiments, at least a portion of the r-pyrolysis gas stream 110 can be introduced into the cracker facility immediately at the outlet of the cracker furnace 430 including, for example, upstream of the outlet heat exchanger 610 (e.g., transfer line exchanger or TLE). Alternatively, or in addition, at least a portion of the r-pyrolysis gas stream 110 can be introduced into the cracker facility 420 downstream of the furnace outlet exchanger 610 and/or may optionally have passed through a separate heat exchanger 611 prior to introduction into the cracker facility 420.

In one embodiment or in combination with any of the mentioned embodiments, at least a portion of the r-pyrolysis gas stream 110 introduced at the location within the cracker facility 420 can have a temperature of at least 300, at least 350, at least 400, at least 450, at least 500, at least 550 and/or not more than about 700, not more than 650, not more than 600, not more than 550, not more than 500, not more than 450° C. Alternatively, or in addition, at least a portion of the r-pyrolysis gas stream introduced into a location of the cracker facility 420 can have a temperature of at least 100, at least 150, at least 200 and/or not more than 350, not more than 300, not more than 250° C.

At least a portion of the r-pyrolysis gas stream 110 introduced into a location of the cracker facility 420 can have a temperature of at least 500, at least 550, at least 600, at least 650, at least 700, at least 750° C. and/or not more than about 1000, not more than 950, not more than 900, not more than 850, not more than 800° C. In one embodiment or in combination with any of the mentioned embodiments, at least a portion of the r-pyrolysis gas stream 110 introduced into a location of the cracker facility 420 can have a temperature of at least 25, at least 50, at least 75 and/or not more than 150, not more than 100, not more than 75° C.

In one embodiment or in combination with any of the mentioned embodiments, at least a portion of the r-pyrolysis gas stream 110 introduced at the location within the cracker facility 420 can have a pressure of at least 25 (1.73 barg), at least 50 (3.5 barg), at least 75 (5.2 barg) and/or not more than 100 (6.89 barg), not more than 75 (5.1 barg), not more than 50 (3.45 barg), all in psig. Additionally, or in the alternative, the pressure of at least a portion of the r-pyrolysis gas stream 110 introduced into the location upstream of a compressor 450 can be not more than 350 (24.1 barg), not more than 300 (20.67 barg), not more than 275 (18.9 barg), not more than 250 (17.2 barg), not more than 225 (15.5 barg), not more than 200 (13.78 barg), not more than 175 (12.1 barg), not more than 150 (10.3 barg), or not more than 125 (8.6 barg), not more than 100 (6.89 barg), not more than 75 (5.2 barg), not more than 50 (3.5 barg), not more than 25 (1.73 barg), not more than 10 (0.69 barg), all in psig or at atmospheric pressure.

In one embodiment or in combination with any of the mentioned embodiments, at least a portion of the r-pyrolysis gas stream 110 can have a pressure of at least 450 (31 barg), 500 (34.5 barg), 550 (37.9 barg) and/or not more than about 650 (44.8 barg), not more than 600 (41.3 barg), not more than 550 (37.9 barg), all in psig At least a portion of the r-pyrolysis gas stream 110 can have a pressure of not more than 500 (34.5 barg), not more than 450 (31.0 barg), not more than 400 (27.6 barg), not more than 350 (24.1 barg), not more than 300 (20.7 barg), not more than 250 (17.2 barg), not more than 200 (13.8 barg), not more than 150 (10.3 barg), or not more than 100 (6.89 barg), all in psig.

As shown in FIG. 12, the r-pyrolysis gas stream 110 may also be combined with a portion of the recycle alkane stream 130 withdrawn from the fractionation section 460 and returned to the inlet of the cracker furnace 430. The recycle alkane stream 130 may be enriched in at least one alkane, such as ethane or propane, and all or a portion may be returned to the inlet of the cracker furnace 430 for additional processing.

Figure 13:
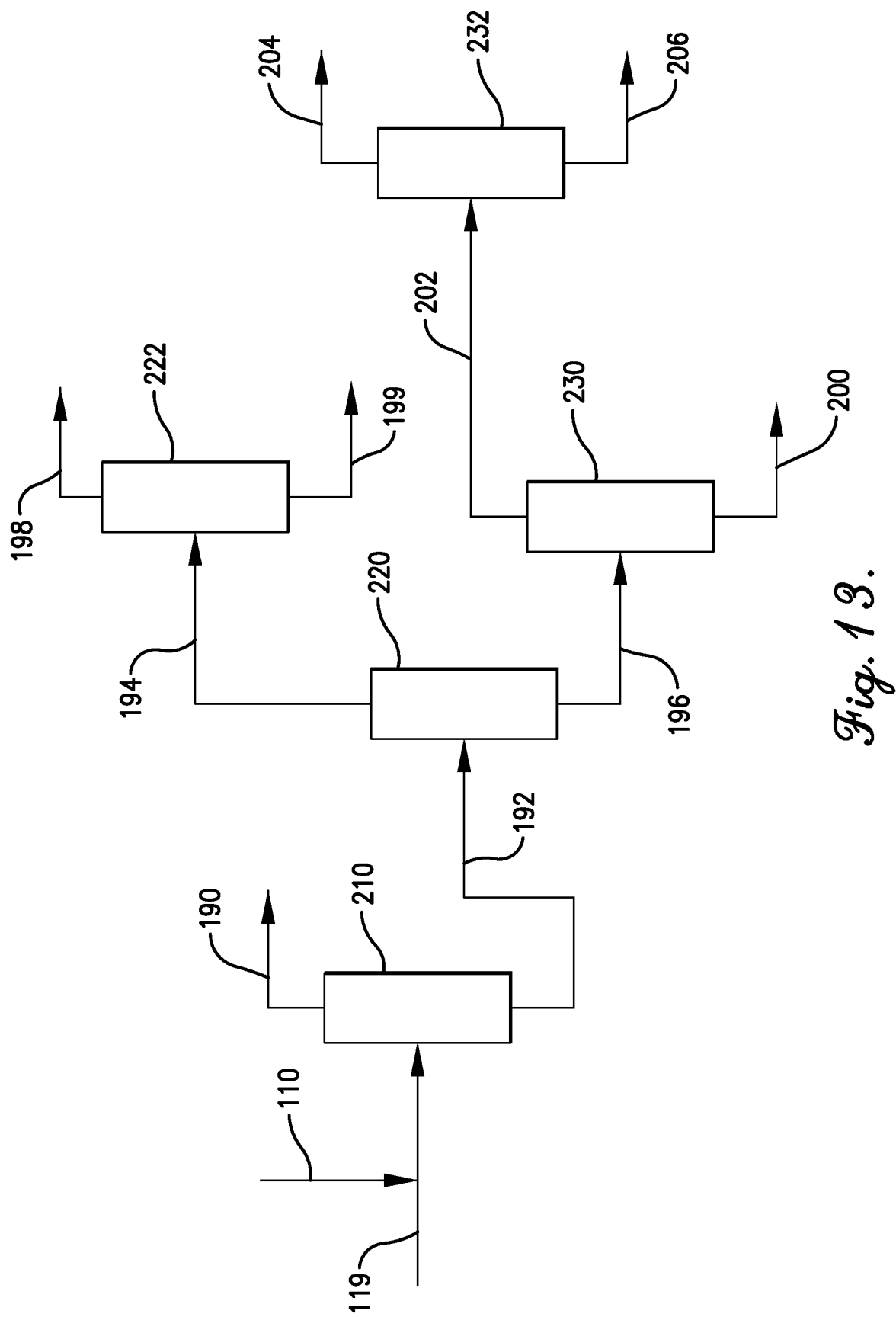
FIG. 13 depicts an exemplary configuration for a separation zone in a cracker facility.
Figure 14:
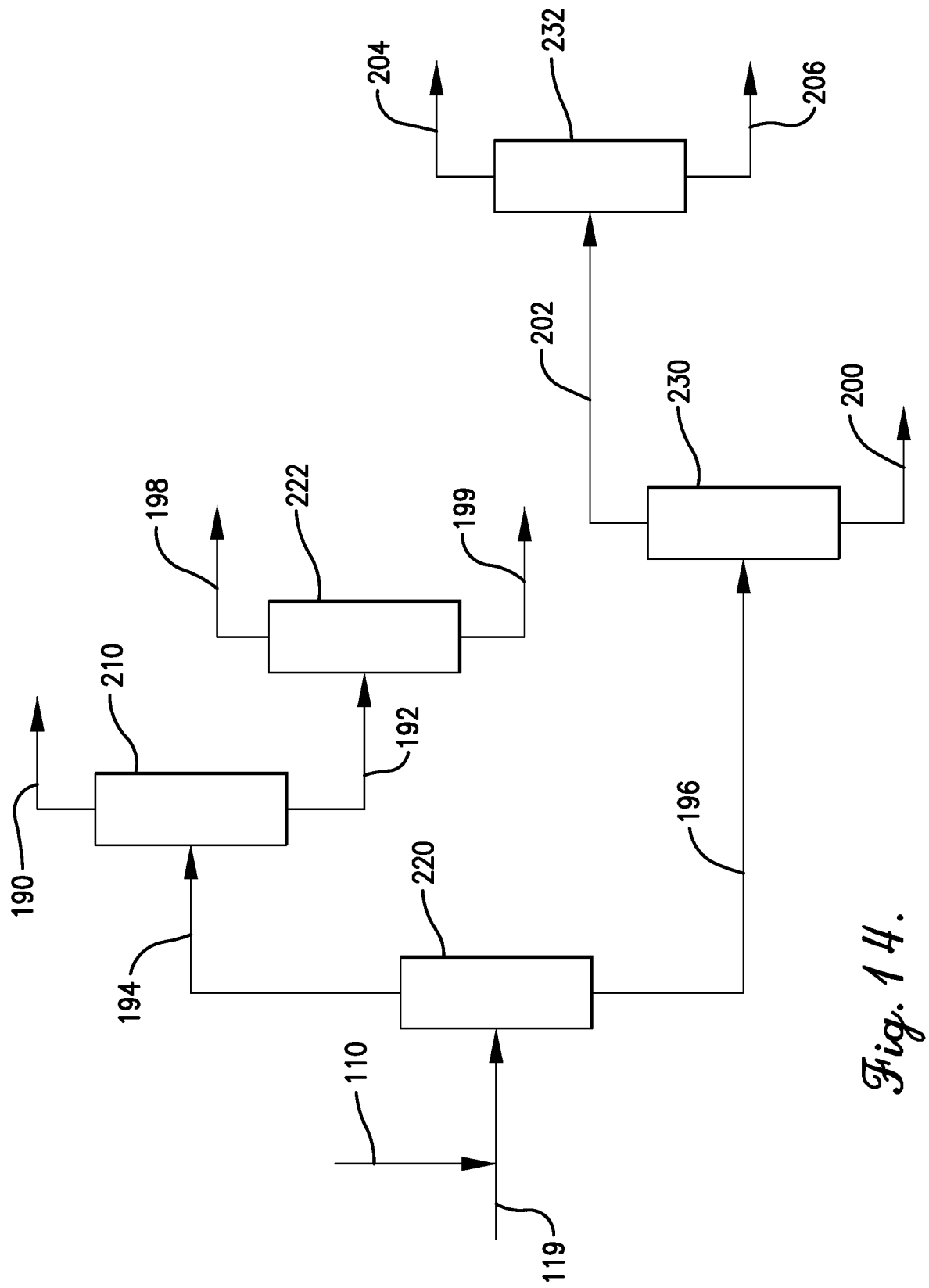
FIG. 14 depicts another exemplary configuration for a separation zone in a cracker facility.
Figure 15:
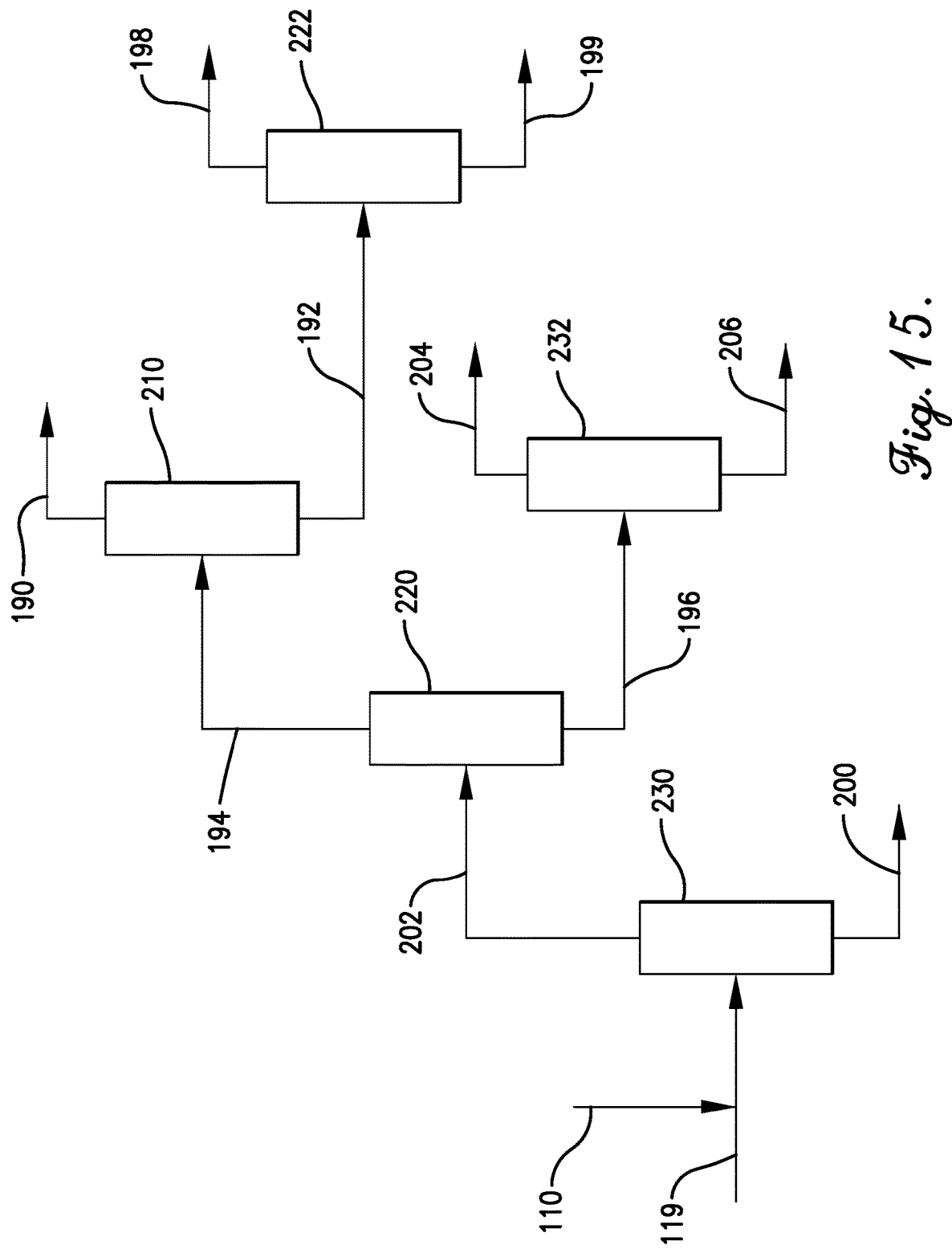
FIG. 15 depicts yet another exemplary configuration for a separation zone in a cracker facility.

Turning now to FIGS. 13-15, schematic depictions of the main steps of the fractionation section 460 for separating the olefin-containing stream 119 exiting the quench zone is provided.

In one embodiment or in combination with any of the mentioned embodiments, the feed stream 119 to the initial column of the fractionation section 460 of the cracker facility may comprise at least a portion of the olefin-containing effluent 119 from the quench zone (downstream of the furnace) and may also comprise at least a portion of a r-pyrolysis gas stream 110.

In one embodiment or in combination with any of the mentioned embodiments, the feed stream to the first column comprises at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95 and/or not more than 75, not more than 70, not more than 65, not more than 60, not more than 55, not more than 50, not more than 45, not more than 40, not more than 35, not more than 30, not more than 25, or not more than 20 weight percent of olefins, based on the total weight of the stream. The olefins can comprise predominantly propylene and/or predominantly ethylene.

The feed stream comprises at least about 5, at least 10, at least 15, at least 20, at least 25, at least 30, at least 35, at least 40, at least 45, at least 50 and/or not more than 75, not more than 70, not more than 65, not more than 60, not more than 55, not more than 50, not more than 45, not more than 40, or not more than 35 weight percent of ethylene, based on the total weight of the stream. The feed stream can comprise at least about 5, at least 10, at least 15, at least 20, at least 25, at least 30, at least 35, at least 40, at least 45, at least 50 and/or not more than 75, not more than 70, not more than 65, not more than 60, not more than 55, not more than 50, not more than 45, not more than 40, or not more than 35 weight percent of propylene, based on the total weight of the stream.

In one embodiment or in combination with any of the mentioned embodiments, the feed stream comprises at least 5, at least 10, at least 15, at least 20, or at least 25 and/or not more than 60, not more than 55, not more than 50, not more than 45, not more than 40, not more than 35, not more than 30, not more than 25, or not more than 20 weight percent of ethane, based on the total weight of the stream. The weight ratio of ethylene to ethane in the feed stream can be greater than 1:1, greater than 1.01:1, greater than 1.05:1, greater than 1.10:1, greater than 1.15:1, greater than 1.2:1.

In one embodiment or in combination with any of the mentioned embodiments, the feed stream comprises at least about 5, at least 10, at least 15, at least 20, at least 25 and/or not more than 60, not more than 55, not more than 50, not more than 45, not more than 40, not more than 35, not more than 30, not more than 25, or not more than 20 weight percent of propane, based on the total weight of the stream. In one embodiment or in combination with any of the mentioned embodiments, the weight ratio of propylene to propane in the feed stream can be greater than 1:1, at least 1.01:1, at least 1.05:1, at least 1.10:1, at least 1.15:1, or at least 1.2:1.

In one embodiment or in combination with any of the mentioned embodiments, feed stream comprises at least about 5, at least 10, at least 15, at least 20, at least 25 and/or not more than 60, not more than 55, not more than 50, not more than 45, not more than 40, or not more than 35) weight percent of propane, based on the total weight of the stream.

In one embodiment or in combination with any of the mentioned embodiments, the feed stream to the first column of the fractionation section comprises at least 5, at least 10, at least 15, at least 20, at least 25, at least 30, at least 35, at least 40, at least 45, at least 50, at least 55 and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, or not more than 10 weight percent of methane and lighter components, based on the total weight of the stream. The feed stream comprises at least 5, at least 10, at least 15, at least 20, at least 25, at least 30, at least 35, at least 40, at least 45, at least 50, at least 55 and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, or not more than 10 weight percent of C2 and heavier components, based on the total weight of the stream.

In one embodiment or in combination with any of the mentioned embodiments, the feed stream to the first column of the fractionation section comprises at least 5, at least 10, at least 15, at least 20, at least 25, at least 30, at least 35, at least 40, at least 45, at least 50, at least 55 and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, or not more than 10 weight percent of C2 and lighter components, based on the total weight of the stream.

The feed stream can comprise at least 5, at least 10, at least 15, at least 20, at least 25, at least 30, at least 35, at least 40, at least 45, at least 50, at least 55 and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, or not more than 10 weight percent of C3 and heavier components, based on the total weight of the stream.

In one embodiment or in combination with any of the mentioned embodiments, the feed stream to the first column of the fractionation section can comprise at least 5, at least 10, at least 15, at least 20, at least 25, at least 30, at least 35, at least 40, at least 45, at least 50, at least 55 and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, or not more than 10 weight percent of C3 and lighter components, based on the total weight of the stream. The feed stream comprises at least 5, at least 10, at least 15, at least 20, at least 25, at least 30, at least 35, at least 40, at least 45, at least 50, at least 55 and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, or not more than 10 weight percent of C4 and heavier components, based on the total weight of the stream.

In one embodiment or in combination with any of the mentioned embodiments, the feed stream can have not more than about 5, not more than 3, not more than 2, not more than 1, not more than 0.5, not more than 0.1, not more than 0.05, or not more than 0.01 weight percent aromatics based on the total weight of the stream. In some cases, the feed stream comprises at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95 percent less aromatics that if the column feed stream did not include r-pyrolysis gas, all other conditions being the same.

The feed stream can comprise not more than 1, not more than 0.75, not more than 0.50, not more than 0.25, or not more than 0.10 ppm of water, based on the total weight of the stream. The feed stream can comprise not more than 1500, not more than 1250, not more than 1000, not more than 750, not more than 500, not more than 250, not more than 100, not more than 75, not more than 50, or not more than 25 ppm of benzene, based on the total weight of the stream.

In one embodiment or in combination with any of the mentioned embodiments, the feed stream to the first column of the fractionation section can have a vapor fraction of at least 0.90, at least 0.92, at least 0.95, at least 0.97, or at least 0.99. The feed stream can be a compressed gas, or it can be a pressurized liquid when introduced into the column. The feed stream to the column can have a pressure of at least 150 (10.3 barg), at least 200 (13.8 barg), at least 250 (17.2 barg), at least 300 (20.7 barg), at least 350 (24.1 barg), at least 400 (27.6 barg), or at least 450 (31.0 barg) and/or not more than 1000 (68.9 barg), not more than 950 (65.5 barg), not more than 900 (62.0 barg), not more than 850 (58.6 barg), not more than 800 (55.1 barg), not more than 750 (51.7 barg), not more than 700 (48.2 barg), not more than 650 (44.7 barg), not more than 600 (41.3 barg), not more than 550 (37.8 barg), not more than 500 (34.5 barg), not more than 450 (31 barg), not more than 400 (27.6 barg), or not more than 350 (24.1 barg), all in psig.

The combined stream, which may include at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95 weight percent and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, not more than 10, or not more than 5 weight percent of the olefin-containing stream or the r-pyrolysis gas stream, may then be introduced into a dealkanizer.

As used herein, the term "dealkanizer" refers to a fractionator for separating a feed stream into an overhead stream enriched in a target alkane and a bottoms stream depleted in the target alkane. For example, a demethanizer is a fractionator for separating a feed stream into an overhead stream enriched in methane and a bottoms stream depleted in methane. Examples of a dealkanizer suitable for use in embodiments of the present technology can include but are not limited to a demethanizer (target alkane is methane), deethanizer (target alkane is ethane), depropanizers (target alkane is propane), and debutanizers (target alkane is butane). One or more dealkanizers may be used in combination to provide product streams of the desirable composition.

In one embodiment or in combination with any of the mentioned embodiments, the feed to the dealkanizer may comprise at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95 weight percent and/or not more than 99, not more than 95, not more than 90, not more than 85, not more than 80, not more than 75, not more than 70, not more than 65, not more than 60, not more than 55, not more than 50, not more than 45, not more than 40, not more than 35, not more than 30, not more than 25, not more than 20, not more than 15, not more than 10, or not more than 5 weight percent of olefins, based on the total weight of the feed stream.

In some cases, at least a portion or a majority of the olefin may end up in the overhead stream, while, in some cases, at least a portion or a majority of the olefin may end up in the bottoms stream. In one embodiment or in combination with any of the mentioned embodiments, at least one of the bottoms stream and the overhead stream from the dealkanizer may comprise at least 5, at least 10, at least 15, at least 20, at least 25, at least 30, at least 35, at least 40, at least 45, at least 50, or at least 55 weight percent and/or not more than 70, not more than 65, not more than 60, not more than 55, not more than 50, not more than 45, not more than 40, not more than 35, not more than 30, not more than 25, not more than 20, not more than 15, not more than 10, or not more than 5 weight percent of olefins, based on the total weight of the overhead or bottoms stream.

Separation zone 440 can have any configuration suitable for separating out desirable components from the feed stream and providing one or more streams of olefin and paraffin product streams. FIGS. 13-15 provide schematic representations of several possible configurations. In particular, FIG. 13 illustrates a separation zone having a demethanizer first, FIG. 14 illustrates a separation zone having a deethanizer first, and FIG. 15 illustrates a separation zone having a depropanizer first. Common elements of these configurations, as well as operating conditions for each, are discussed in further detail below.

In one embodiment or in combination with any of the mentioned embodiments, the overhead stream 190 from a demethanizer 210 can comprise not more than 35, not more than 30, not more than 25, not more than 20, not more than 15, not more than 10, not more than 5, not more than 2, or not more than 1 weight percent of olefins, based on the total weight of the overhead stream 190. The bottoms stream 192 from a demethanizer 210 may comprise at least 5, at least 10, at least 15, at least 20, at least 25, at least 30, at least 35, at least 40, or at least 45 weight percent and/or not more than 85, not more than 80, not more than 75, not more than 70, not more than 65, not more than 60, not more than 55, not more than 50, not more than 45, or not more than 40 weight percent of olefins, based on the total weight of the bottoms stream 192. The olefins in the bottoms stream 192 can comprise at least 45, at least 50, at least 55, at least 60, at least 65, at least 70, at least 75, at least 80, at least 85, at least 90, or at least 95 weight percent of ethylene and propylene, based on the total weight of olefins in the bottoms stream 192.

In one embodiment or in combination with any of the mentioned embodiments, the overhead stream 194 from a deethanizer 220 can comprise at least 5, at least 10, at least 15, at least 20, at least 25, at least 30, at least 35, at least 40, or at least 45 weight percent and/or not more than 85, not more than 80, not more than 75, not more than 70, not more than 65, not more than 60, not more than 55, not more than 50, not more than 45, or not more than 40 weight percent of olefins, based on the total weight of the overhead stream 194. The olefins in the overhead stream 194 can comprise at least 45, at least 50, at least 55, at least 60, at least 65, at least 70, at least 75, or at least 80 and/or not more than 99, not more than 95, not more than 90, not more than 85, not more than 80, or not more than 75 weight percent of ethylene, based on the total weight of olefin in the overhead stream 194.

In one embodiment or in combination with any of the mentioned embodiments, the bottoms stream 196 from a deethanizer 220 may comprise at least 5, at least 10, at least 15, at least 20, at least 25, at least 30, at least 35, at least 40, or at least 45 weight percent and/or not more than 85, not more than 80, not more than 75, not more than 70, not more than 65, not more than 60, not more than 55, not more than 50, not more than 45, or not more than 40 weight percent of olefins based on the total weight of the bottoms stream 196. The olefin in the bottoms stream 196 can comprise at least 45, at least 50, at least 55, at least 60, at least 65, at least 70, at least 75, or at least 80 and/or not more than 99, not more than 95, not more than 90, not more than 85, not more than 80, or not more than 75 weight percent of propylene, based on the total weight of olefin in the bottoms stream 196.

In one embodiment or in combination with any of the mentioned embodiments, the bottoms stream 200 from a depropanizer 230 can comprise not more than 35, not more than 30, not more than 25, not more than 20, not more than 15, not more than 10, not more than 5, not more than 2, or not more than 1 weight percent of olefins, based on the total weight of the bottoms stream 200. The overhead stream 202 from a depropanizer 230 may comprise at least 5, at least 10, at least 15, at least 20, at least 25, at least 30, at least 35, at least 40, or at least 45 weight percent and/or not more than 85, not more than 80, not more than 75, not more than 70, not more than 65, not more than 60, not more than 55, not more than 50, not more than 45, or not more than 40 weight percent of olefins, based on the total weight of the overhead stream 202. The olefins in the overhead stream 202 can comprise at least 45, at least 50, at least 55, at least 60, at least 65, at least 70, at least 75, at least 80, at least 85, at least 90, or at least 95 weight percent of ethylene and propylene, based on the total weight of olefins in the overhead stream 202.

In one embodiment or in combination with any of the mentioned embodiments, the fractionation zone of the cracker facility may comprise at least one olefin-alkane fractionator for separating a target olefin from a stream comprising the target olefin and an alkane of corresponding hydrocarbon number. For example, the olefin-alkane fractionator may be an ethylene-ethane fractionator (or ethylene splitter or ethylene fractionator) configured to provide an overhead stream enriched in ethylene and a bottoms stream depleted in ethylene. With an ethylene splitter, the bottoms stream may be enriched in ethane and the overhead stream depleted in ethylene.

Similarly, when the olefin-alkane fractionator is configured to separate propylene (a propylene-propane fractionator, a propylene splitter, or a propylene fractionator), the overhead stream may be enriched in propylene (and the bottoms stream depleted in propylene) and the bottoms stream may be enriched in propane (and the overhead stream depleted in propane).

Referring initially to FIGS. 13-15, an olefin-containing feed stream 119 from the quench section (not shown in FIGS. 13-15) may be introduced into an initial column in the fractionation zone or train. In one embodiment or in combination with any of the mentioned embodiments, the initial column of the fractionation train may be a demethanizer as shown in FIG. 13, a deethanizer as shown in FIG. 14, or a depropanizer FIG. 15, or it could be another column such as a debutanizer.

When the column is a demethanizer (FIG. 13) methane and lighter ($CO$, $CO_2$, $H_2$) components are separated from the ethane and heavier components. The demethanizer 210 can be operated at a temperature of at least −145, or at least −142, or at least −140, or at least −135, in each case ° C. and/or not more than −120, not more than −125, not more than −130, not more than −135° C. The bottoms stream 192 from the demethanizer column 210, which includes at least 50, or at least 55, or at least 60, or at least 65, or at least 70, or at least 75, or at least 80, or at least 85, or at least 90, or at least 95 or at least 99, in each case percent of the total amount of ethane and heavier components introduced into the column 210, is then introduced into a deethanizer column 220, wherein the C2 and lighter components are separated from the C3 and heavier components by fractional distillation.

The deethanizer 220 can be operated with an overhead temperature of at least −35, or at least −30, or at least −25, or at least −20, in each case ° C. and/or not more than −5, not more than −10, not more than −15, not more than −20° C., and an overhead pressure of at least 3, or at least 5, or at least 7, or at least 8, or at least 10, in each case barg and/or not more than 20, or not more than 18, or not more than 17, or not more than 15, or not more than 14, or not more than 13, in each case barg. The deethanizer column 220 recovers at least 60, or at least 65, or at least 70, or at least 75, or at least 80, or at least 85, or at least 90, or at least 95, or at least 97, or at least 99, in each case percent of the total amount of C2 and lighter components introduced into the column 220 in the overhead stream.

In one embodiment or in combination with any of the mentioned embodiments, the overhead stream 194 removed from the deethanizer column 220 comprises at least 50, or at least 55, or at least 60, or at least 65, or at least 70, or at least 75, or at least 80, or at least 85, or at least 90, or at least 95, in each case weight percent of ethane and ethylene, based on the total weight of the overhead stream 194.

As shown in FIG. 13, the C2 and lighter overhead stream from the deethanizer 220 may further separated in an ethane-ethylene fractionator column 222 (ethylene fractionator). In the ethane-ethylene fractionator column 222, an ethylene and lighter component stream 198 can be withdrawn from the overhead of the column or as a side stream from the top half of the column, while the ethane and any residual heavier components can be removed in the bottoms stream 199.

The ethylene fractionator 222 may be operated at an overhead temperature of at least −45, or at least −40, or at least −35, or at least −30, or at least −25, or at least −20, in each case ° C. and/or not more than −15, or not more than −20, or not more than −25, in each case ° C., and an overhead pressure of at least 10, or at least 12, or at least 15, in each case barg and/or not more than 25, not more than 22, not more than 20 barg. The overhead stream 198, which is enriched in ethylene, can include at least 70, or at least 75, or at least 80, or at least 85, or at least 90, or at least 95, or at least 97, or at least 98, or at least 99, in each case weight percent ethylene, based on the total weight of the stream 198 and may be sent to downstream processing unit for further processing, storage, or sale. The overhead ethylene stream 198 may comprise a r-ethylene composition or stream. In one embodiment or in combination with any of the mentioned embodiments, the r-ethylene stream may be used to make one or more petrochemicals.

The bottoms stream 199 from the ethane-ethylene fractionator 222 may include at least 40, or at least 45, or at least 50, or at least 55, or at least 60, or at least 65, or at least 70, or at least 75, or at least 80, or at least 85, or at least 90, or at least 95, or at least 98, in each case weight percent ethane, based on the total weight of the bottoms stream 199. All or a portion of the recovered ethane may be recycled to the cracker furnace as additional feedstock, alone or in combination with the cracker feed stream, as discussed previously.

The liquid bottoms stream 196 withdrawn from the deethanizer column 220, which may be enriched in C3 and heavier components, may be separated in a depropanizer 230, as shown in FIG. 13. In the depropanizer 230, C3 and lighter components are removed as an overhead vapor stream 202, while C4 and heavier components may exit the column in the liquid bottoms stream 200. The depropanizer 230 can be operated with an overhead temperature of at least 20, or at least 35, or at least 40, in each case ° C. and/or not more than 70, not more than 65, not more than 60, not more than 55° C., and an overhead pressure of at least 10, or at least 12, or at least 15, in each case barg and/or not more than 20, or not more than 17, or not more than 15, in each case barg.

The depropanizer column 230 recovers at least 60, or at least 65, or at least 70, or at least 75, or at least 80, or at least 85, or at least 90, or at least 95, or at least 97, or at least 99, in each case percent of the total amount of C3 and lighter components introduced into the column 230 in the overhead stream 202. In one embodiment or in combination with any of the mentioned embodiments, the overhead stream 202 removed from the depropanizer column 230 comprises at least or at least 50, or at least 55, or at least 60, or at least 65, or at least 70, or at least 75, or at least 80, or at least 85, or at least 90, or at least 95, or at least 98, in each case weight percent of propane and propylene, based on the total weight of the overhead stream 202.

The overhead stream 202 from the depropanizer 230 is introduced into a propane-propylene fractionator 232 (propylene fractionator), wherein the propylene and any lighter components are removed in the overhead stream 204, while the propane and any heavier components exit the column in the bottoms stream 206. The propylene fractionator 232 may be operated at an overhead temperature of at least 20, or at least 25, or at least 30, or at least 35, in each case ° C. and/or not more than 55, not more than 50, not more than 45, not more than 40° C., and an overhead pressure of at least 12, or at least 15, or at least 17, or at least 20, in each case barg and/or not more than 20, or not more than 17, or not more than 15, or not more than 12, in each case barg.

The overhead stream 204, which is enriched in propylene, can include at least 70, or at least 75, or at least 80, or at least 85, or at least 90, or at least 95, or at least 97, or at least 98, or at least 99, in each case weight percent propylene, based on the total weight of the stream 204 and may be sent to downstream processing unit for further processing, storage, or sale. The overhead propylene stream 204 produced during the cracking of a cracker feedstock containing r-pyoil is a r-propylene composition or stream. The stream may be used to make one or more petrochemicals.

The bottoms stream 206 from the propane-propylene fractionator 232 may include at least 40, or at least 45, or at least 50, or at least 55, or at least 60, or at least 65, or at least 70, or at least 75, or at least 80, or at least 85, or at least 90, or at least 95, or at least 98, in each case weight percent propane, based on the total weight of the bottoms stream 206. All or a portion of the recovered propane may be recycled to the cracker furnace as additional feedstock, alone or in combination with r-pyoil, as discussed previously.

In one embodiment or in combination with any of the mentioned embodiments, the bottoms stream 200 from the depropanizer column 230 may be sent to a debutanizer column for separating C4 components, including butenes, butanes and butadienes, from C5+ components. The debutanizer (when present) can be operated with an overhead temperature of at least 20, or at least 25, or at least 30, or at least 35, or at least 40, in each case ° C. and/or not more than 60, or not more than 65, or not more than 60, or not more than 55, or not more than 50, in each case ° C. and an overhead pressure of at least 2, or at least 3, or at least 4, or at least 5, in each case barg and/or not more than 8, or not more than 6, or not more than 4, or not more than 2, in each case barg. The debutanizer column recovers at least 60, or at least 65, or at least 70, or at least 75, or at least 80, or at least 85, or at least 90, or at least 95, or at least 97, or at least 99, in each case percent of the total amount of C4 and lighter components introduced into the column in the overhead stream.

In one embodiment or in combination with any of the mentioned embodiments, the overhead stream removed from the debutanizer column comprises at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent of butadiene, based on the total weight of the overhead stream. The overhead stream produced during the cracking of a cracker feedstock can be an r-butadiene composition or stream. The bottoms stream from the debutanizer includes mainly C5 and heavier components, in an amount of at least 50, or at least 60, or at least 70, or at least 80, or at least 90, or at least 95 weight percent, based on the total weight of the stream. The debutanizer bottoms stream may be sent for further separation, processing, storage, sale or use.

The overhead stream from the debutanizer, or the C4s, can be subjected to any conventional separation methods such as extraction or distillation processes to recover a more concentrated stream of butadiene.

As shown in FIGS. 13-15, at least a portion of the r-pyrolysis gas stream 110 can be combined with the olefin-containing effluent stream 119 introduced into the first fractionation column. In one embodiment or in combination with any of the mentioned embodiments, the feed stream to the first fractionation column can comprise at least 5, at least 10, at least 15, at least 20, at least 25, at least 30, at least 35, at least 40, at least 45, at least 50, at least 55, at least 60, at least 65, or at least 70 weight percent and/or not more than about 99, not more than 95, not more than 90, not more than 85, not more than 80, not more than 75, not more than 70, not more than 65, not more than 60, not more than 55, not more than 50, not more than 45, not more than 40, or not more than 35 weight percent of r-pyrolysis gas. The remaining feed, when present, can comprise olefin-containing effluent 119 from one or more cracker furnaces as discussed in detail previously.

In one embodiment or in combination with any of the mentioned embodiments, the capacity and/or efficiency of one or more of the distillation columns in the fractionation zone including, for example, the demethanizer, the deethanizer or ethylene splitter (or fractionator), the depropanizer or propylene splitter (or fractionator), and/or the debutanizer, may be increased as a result the introduction of r-pyrolysis gas into the cracker facility.

For example, one embodiment or in combination with any of the mentioned embodiments, a column feed stream including a r-pyrolysis gas may be introduced into a fractionation column, examples of which include the demethanizer, deethanizer, and depropanizer. The column feed that includes r-pyrolysis gas can comprise C2 to C4 olefins, and it may comprise predominantly propylene and/or ethylene. The feed stream to the fractionation column may include ethylene and/or propylene in an amount of at least 5, at least 10, at least 15, at least 20, at least 25, at least 30, at least 35, at least 40, at least 45, at least 50, at least 55, at least 60, at least 65, at least 70, at least 75, or at least 80 and/or not more than 99, not more than 95, not more than 90, not more than 85, not more than 80, not more than 75, not more than 70, not more than 65, not more than 60, not more than 55, not more than 50, not more than 45, not more than 40, or not more than 35 weight percent, based on the total weight of the feed stream. The feed stream may include methane and lighter components in an amount of at least 1, at least 2, at least 5, at least 10, at least 15, or at least 20 and/or not more than 50, not more than 45, not more than 40, not more than 35, not more than 30, not more than 25, not more than 20, or not more than 15 weight percent, based on the total weight of the feed stream.

In one embodiment or in combination with any of the mentioned embodiments, the feed stream introduced into the deethanizer 220 may be separated into a light overhead stream 194 enriched in C2 and lighter components and a heavier bottoms stream 196 depleted C2 and lighter components (or enriched in C3 and heavier components). The C2 enriched overhead stream 194 can comprise at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C2 and lighter components present in the feed stream, while the C2 depleted bottoms stream 196, which can include predominantly C3 and heavier components, comprises at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C3 and heavier components present in the feed stream.

The overhead stream 194 can include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of the C3 and heavier components present in the column feed stream, while the bottoms stream 196 from the deethanizer 220 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C3 and heavier components present in the feed stream.

The bottoms stream 196 can include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of the C2 and lighter components present in the column feed stream, while the overhead stream 194 from the deethanizer 220 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C2 and lighter components present in the feed stream.

The overhead stream 194 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C2 and lighter components, based on the total weight of the overhead stream 194, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C3 and heavier components, based on the total weight of the overhead stream 194.

The bottoms stream 196 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C3 and heavier components, based on the total weight of the bottoms stream 196, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C2 and lighter components, based on the total weight of the bottoms stream 196.

In one embodiment or in combination with any of the mentioned embodiments, the feed stream introduced into the deethanizer 220 may be separated into a light overhead stream enriched in C2 and lighter components and a heavier bottoms stream depleted C2 and lighter components (or enriched in C3 and heavier components). The C2 enriched overhead stream can comprise at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C2 and lighter components present in the feed stream, while the C2 depleted bottoms stream, which can include predominantly C3 and heavier components, comprises at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C3 and heavier components present in the feed stream.

The overhead stream 194 can include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of the C3 and heavier components present in the column feed stream, while the bottoms stream 196 from the deethanizer 220 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of ethylene and heavier components present in the feed stream.

The bottoms stream 196 can include at least 0.01, at least 0.05, at least 0.10, at least 0.50, at least 1, at least 1.5, at least 2, at least 5, at least 8, or at least 10 weight percent and/or not more than 10, 8, 5, 3, 2, or 1 weight percent of the C2 and lighter components present in the column feed stream, while the overhead stream 194 from the deethanizer can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C2 and lighter components present in the feed stream.

The overhead stream 194 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C2 and lighter components, based on the total weight of the overhead stream, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C3 and heavier components, based on the total weight of the overhead stream 194.

The bottoms stream 196 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, 85, 80, 75, or 70 weight percent of C3 and heavier components, based on the total weight of the bottoms stream 196, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C2 and lighter components, based on the total weight of the bottoms stream 196.

In one embodiment or in combination with any of the mentioned embodiments, the feed stream introduced into the demethanizer column 210 may be separated into a light overhead stream 190 enriched in C1 and lighter components and a heavier bottoms stream 192 depleted C1 and lighter components (or enriched in C2 and heavier components).

In one embodiment or in combination with any of the mentioned embodiments, the C1 enriched overhead stream 190 can comprise at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C1 and lighter components present in the feed stream, while the C1 depleted bottoms stream 192, which can include predominantly C2 and heavier components, comprises at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C2 and heavier components present in the feed stream.

The overhead stream 190 can include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of the C2 and heavier components present in the column feed stream, while the bottoms stream 192 from the demethanizer 210 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of ethylene and heavier components present in the feed stream.

The bottoms stream 192 can include at least 0.01, at least 0.05, at least 0.10, at least 0.50, at least 1, at least 1.5, at least 2, at least 5, at least 8, or at least 10 weight percent and/or not more than 10, 8, 5, 3, 2, or 1 weight percent of the C1 and lighter components present in the column feed stream, while the overhead stream 190 from the demethanizer 210 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C1 and lighter components present in the feed stream.

The overhead stream 190 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C1 and lighter components, based on the total weight of the overhead stream 190, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C2 and heavier components, based on the total weight of the overhead stream 190.

The bottoms stream 192 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C2 and heavier components, based on the total weight of the bottoms stream 192, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C1 and lighter components, based on the total weight of the bottoms stream 192.

In one embodiment or in combination with any of the mentioned embodiments, the feed stream introduced into the depropanizer 230 may be separated into a light overhead stream 202 enriched in C3 and lighter components and a heavier bottoms stream 200 depleted C3 and lighter components (or enriched in C4 and heavier components). The C3 enriched overhead stream 202 can comprise at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C3 and lighter components present in the feed stream, while the C3 depleted bottoms stream 200, which can include predominantly C4 and heavier components, comprises at least 20, at least 25, at least 30, at least 35, at least 40, at least 45, at least 50, at least 55, at least 60, at least 65, at least 70, at least 75, at least 80, at least 85, at least 90, at least 92, at least 95, at least 97, or at least 99 weight percent of the total weight of C4 and heavier components present in the feed stream.

The overhead stream 202 can include at least 0.01, at least 0.05, at least 0.10, at least 0.50, at least 1, at least 1.5, at least 2, at least 5, at least 8, or at least 10 weight percent and/or not more than 10, 8, 5, 3, 2, or 1 weight percent of the C4 and heavier components present in the column feed stream, while the bottoms stream 200 from the depropanizer 230 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of ethylene and heavier components present in the feed stream.

The bottoms stream 200 can include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of the C3 and lighter components present in the column feed stream, while the overhead stream 202 from the depropanizer 230 can include at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C3 and lighter components present in the feed stream.

The overhead stream 202 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C3 and lighter components, based on the total weight of the overhead stream 202, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C4 and heavier components, based on the total weight of the overhead stream 202.

The bottoms stream 200 may comprise at least 5, at least 10, at least 15, at least 20, at least 25, at least 30, at least 35, at least 40, at least 45, at least 50, at least 55, at least 60, at least 65, or at least 70 weight percent and/or not more than 99, not more than 95, not more than 90, not more than 85, not more than 80, not more than 75, or not more than 70 weight percent of C4 and heavier components, based on the total weight of the bottoms stream 200, and may include at least 0.01, at least 0.05, at least 0.10, at least 0.50, at least 1, at least 1.5, at least 2, at least 5, at least 8, or at least 10 weight percent and/or not more than 10, not more than 8, not more than 5, not more than 3, not more than 2, or not more than 1 weight percent of C3 and lighter components, based on the total weight of the bottoms stream 200.

In one embodiment or in combination with any of the mentioned embodiments, introduction of the r-pyrolysis gas stream 110 into the fractionation zone of a cracker facility may improve the operation one or more columns in the fractionation zone. For example, at least one of the olefin fractionators (e.g., the ethylene splitter 222 and/or propylene splitter 232) may operate more efficiently as compared to when these columns are fed streams that include only a stream of cracked effluent from the cracker furnace. Such efficiency may include, for example, better separation and/or increased capacity.

In one embodiment or in combination with any of the mentioned embodiments, a feed stream including r-pyrolysis gas 110 may be introduced into an olefin fractionator, wherein it may be separated into an overhead stream enriched in at least one olefin and a bottoms stream depleted in at least one olefin. For example, when the olefin fractionator is an ethylene fractionator 222, the overhead stream 198 may be enriched in ethylene and the bottoms stream 199 depleted in ethylene and enriched in ethane. Similarly, when the olefin fractionator is a propylene fractionator 232, the overhead stream 204 may be enriched in propylene and the bottoms steam 206 depleted in propylene and enriched in propane.

In one embodiment or in combination with any of the mentioned embodiments, the overhead stream 198, 204 enriched in olefin may comprise at least 50, at least 55, at least 60, at least 65, at least 70, at least 75, at least 80, at least 85, or at least 90 weight percent of olefin, based on the total weight of the stream. The olefin may comprise predominantly ethylene, predominantly propylene, or it may include combinations thereof. The overhead stream 198 may comprise at least 60, at least 65, at least 70, at least 75, at least 80, at least 85, or at least 90 weight percent ethylene, based on the total weight of olefin in the stream. The overhead stream 204 may comprise at least 60, at least 65, at least 70, at least 75, at least 80, at least 85, or at least 90 weight percent propylene, based on the total weight of olefin in the stream.

In one embodiment or in combination with any of the mentioned embodiments, the total amount of ethylene in the overhead stream 198 from the olefin fractionator (ethylene fractionator 222) can be at least 60, at least 65, at least 70, at least 75, at least 80, at least 85, at least 90, at least 95, at least 97, or at least 99 weight percent, based on the total weight of the stream. Additionally, or in the alternative, the overhead stream 198 from the olefin fractionator 222 may comprise not more than about 25, not more than 20, not more than 15, not more than 10, not more than 8, not more than 5, not more than 3, not more than 2, not more than 1, not more than 0.5 weight percent of ethane, based on the total weight of the stream.

In one embodiment or in combination with any of the mentioned embodiments, the total amount of propylene in the overhead stream 202 from the olefin fractionator (propylene fractionator 232) can be at least 60, at least 65, at least 70, at least 75, at least 80, at least 85, at least 90, at least 95, at least 97, or at least 99 weight percent, based on the total weight of the stream. Additionally, or in the alternative, the overhead stream 202 from the olefin fractionator 232 may comprise not more than about 25, not more than 20, not more than 15, not more than 10, not more than 8, not more than 5, not more than 3, not more than 2, not more than 1, not more than 0.5 weight percent of ethane, based on the total weight of the stream.

In one embodiment or in combination with any of the mentioned embodiments, the overhead stream 198, 204 from the olefin fractionator 222, 232 comprises at least 60, at least 65, at least 70, at least 75, at least 80, at least 85, at least 90, or at least 95 weight percent of the total amount of olefin introduced into the fractionator 222, 232, while the bottoms stream 199, 206 from the olefin fractionator 222, 232 comprise not more than about 35, not more than 30, not more than 25, not more than 20, not more than 15, not more than 10, not more than 5, not more than 2, or not more than 1 weight percent of the olefin introduced into the fractionator.

When the feed to the fractionator comprises r-pyrolysis gas in an amount as described previously, one or more of the following may be met—
 the mole ratio of said at least one olefin to its corresponding alkane in said column feed stream is at least 0.1% higher than if said column feed stream did not include said r-pyrolysis gas but had the same mass flow rate;
 the mass flow rate of a corresponding alkane of said at least one olefin in said overhead stream is at least 0.1% lower than if said column feed stream did not include said r-pyrolysis gas but had the same mass flow rate;
 the reflux ratio used during said separating is at least 0.1% lower than the reflux ratio used if said column feed stream did not include said r-pyrolysis gas but had the same mass flow rate;
 the pressure drop across the column is at least 0.1% lower than if the column feed stream did not include said r-pyrolysis gas but had the same mass flow rate;
 the mass flow rate of liquid within the column is at least 0.1 wt % lower than if the column feed stream did not include said r-pyrolysis gas but had the same mass flow rate; and
 the energy input into said column is at least 0.1% lower than if the column feed stream did not include said r-pyrolysis gas but had the same mass flow rate.

In one embodiment or in combination with any of the mentioned embodiments, at least two, three, four, five, or all of the above may be true.

In one embodiment or in combination with any of the mentioned embodiments, the mole ratio of said at least one olefin to its corresponding alkane in said column feed stream is at least 0.5, at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99% higher than if said column feed stream did not include said r-pyrolysis gas but had the same mass flow rate.

In one embodiment or in combination with any of the mentioned embodiments, the mass flow rate of a corresponding alkane of said at least one olefin in said overhead stream is at least 0.5, at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99%% lower than if said column feed stream did not include said r-pyrolysis gas but had the same mass flow rate.

In one embodiment or in combination with any of the mentioned embodiments, the reflux ratio used during said separating is at least 0.5, at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99% lower than the reflux ratio used if said column feed stream did not include said r-pyrolysis gas but had the same mass flow rate.

In one embodiment or in combination with any of the mentioned embodiments, the pressure drop across the column is at least 0.5, at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 99% lower than if the column feed stream did not include said r-pyrolysis gas but had the same mass flow rate.

In one embodiment or in combination with any of the mentioned embodiments, the mass flow rate of liquid within the column is at least 0.1 wt % lower than if the column feed stream did not include said r-pyrolysis gas but had the same mass flow rate.

In one embodiment or in combination with any of the mentioned embodiments, the energy input into said column is at least 0.1% lower than if the column feed stream did not include said r-pyrolysis gas but had the same mass flow rate.

Figure 16:
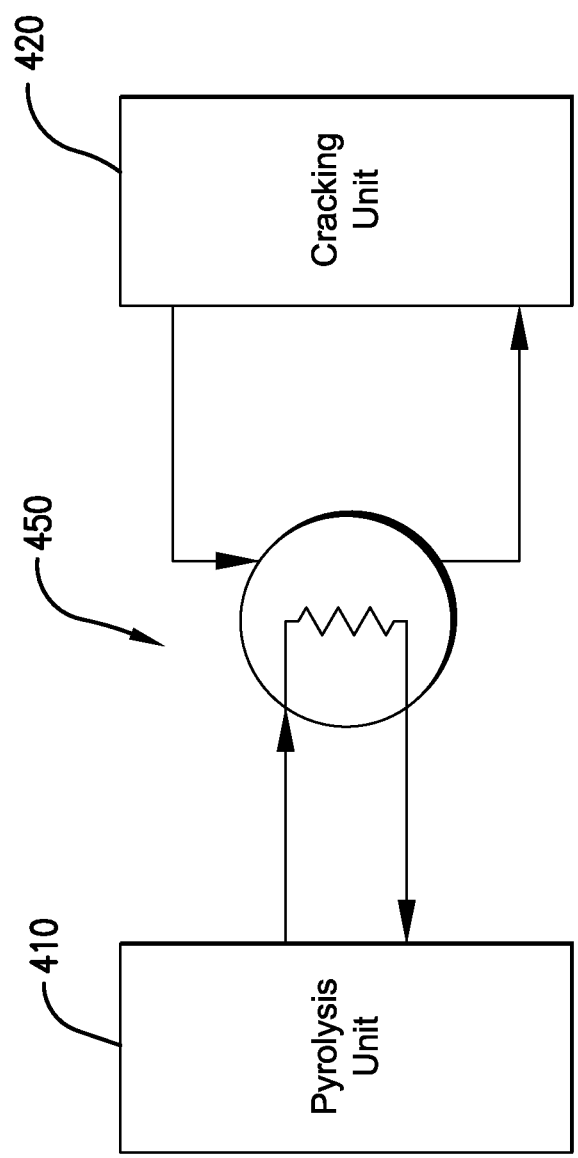
FIG. 16 depicts an exemplary system for heat integration between a pyrolysis facility and a cracker facility.

When a pyrolysis facility and cracking facility are located near one another, at least a portion of the two processes may be energy integrated such that energy from at least one piece of equipment or process stream in one unit may be transferred to another piece of equipment or process stream in the other unit. In one embodiment or in combination with any of the mentioned embodiments, the energy exchange may occur in an energy exchange zone 480 configured to transfer heat or energy between the pyrolysis unit 410 and the cracking unit 420. A schematic diagram generally illustrating this is provided in FIG. 16.

Any suitable structure for exchanging energy or heat between the pyrolysis unit 410 and the cracking unit 420 can be used in the energy exchange zone 480. For example, the energy exchange zone 480 may include equipment for performing direct energy exchange or indirect energy exchange, and/or one or more types of heat exchangers, including direct heat exchangers, indirect heat exchangers, and combinations thereof. When the energy exchange performed in the energy exchange zone 480 comprises heat exchange, one or more process streams from one of the units may be used to heat one or more process streams from the other unit. Examples of process streams include, but are not limited to, feed streams, product streams, intermediate streams, as well as utility streams like steam, cooling water, boiler feed water, and streams of heat transfer media. The energy exchange zone may include a single exchanger for exchanging heat between the two units or streams, or two or more exchangers operated in parallel or series.

In one embodiment or in combination with any of the mentioned embodiments, the warmed stream from which the heat is transferred can originate from the pyrolysis unit 410 and can, for example, be selected from the group consisting of the effluent from the pyrolysis furnace, the pyrolysis oil, or the pyrolysis gas streams. Alternatively, the warmed stream can originate from the cracking unit 420 and can, for example, be selected from the group consisting of the olefin-containing effluent withdrawn from the furnace, compressor intermediate streams (between compression zones), or column overhead streams.

In one embodiment or in combination with any of the mentioned embodiments, the cooled stream to which the heat is transferred can originate from the pyrolysis unit 410 and can, for example, be selected from the group consisting of the pyrolysis feed or intermediate stream. Alternatively, the cooled stream to which the heat or energy is transferred can originate from the cracking unit 420. Examples of such streams can include the feed to the cracking furnace, column bottoms streams, and column feed streams.

In one embodiment or in combination with any of the mentioned embodiments, the stream being warmed or cooled can be a utility stream such as, for example, cooling water, boiler feed water, steam, or plant air, which itself may be heated in one unit and then used to heat a stream (cooled) in another unit. In some cases, one stream can be used as fuel so that, when combusted, the energy may be directly or indirectly provided to a stream or streams in the other unit.

In one embodiment or in combination with any of the mentioned embodiments, the energy exchange zone 480 may be configured to permit energy transfer between at least a portion of the r-pyrolysis gas stream and at least one heat transfer stream within the heat exchange zone. Such heat transfer streams may include water (to make steam), steam (to make superheated steam), a heat transfer medium, and/or another process stream from the pyrolysis and/or cracker facilities. Multiple heat transfer steps can be performed to cool the r-pyrolysis gas to a target temperature, and each heat transfer step can include energy transfer between the same or different streams.

In one embodiment or in combination with any of the mentioned embodiments, the r-pyrolysis gas exiting the energy exchange zone 480 can be introduced into one or more locations of the separation zone of the cracker facility 420 downstream of the cracker furnace as discussed in detail previously.

EXAMPLES

Examples 1-7

Pyrolysis Unit

The pyrolysis unit was comprised of a 1 L quartz round bottom flask containing three necks. One neck was fitted with an open-ended quartz dip tube connected by a stainless-steel adapter to a gas inlet. A K-type thermocouple was also inserted through the dip tube, subsurface into the reaction mixture. In addition to monitoring reaction temperature, this dip tube was used to introduce gas feeds, such as nitrogen, hydrogen, or steam, subsurface into the pyrolysis mixture and to ensure adequate mixing during the pyrolysis experiments. Another neck was fitted with a glass distillation head. The distillation head was topped with a thermowell and J-type thermocouple. The outlet of the distillation head was fitted to a vertically hung condenser containing a 50/50 mixture of glycol and water as the cooling medium. This condenser was maintained at 60° C. The outlet of the condenser was fitted to a glass gas separation tube. The liquid outlet of this tube was fitted to a graduated product tank, while the gas outlet of this tube was connected to two dry ice traps in series. Any non-condensable vapors exited the dry ice traps and were collected in TEDLAR® (commercially available from DuPont) gas sample bags for analysis.

Analytical

Analysis of the reaction feed components and products was done by gas chromatography. All percentages are by weight unless specified otherwise. Liquid samples were analyzed on an Agilent 7890A using a Restek RTX-1 column (30 meters×320 micron ID, 0.5 micron film thickness) over a temperature range of 35° C. to 300° C. and a flame ionization detector. Gas samples were analyzed on an Agilent 8890 gas chromatograph. This GC was configured to analyze refinery gas up to $C_6$ with $H_2S$ content. The system used four valves, three detectors, 2 packed columns, 3 micro-packed columns, and 2 capillary columns. The columns used were the following: (1) 2 ft×1/16 in, 1 mm i.d. HayeSep A 80/100 mesh UltiMetal Plus 41 mm; (2) 1.7 m×1/16 in, 1 mm i.d. HayeSep A 80/100 mesh UltiMetal Plus 41 mm; (3) 2 m×1/16 in, 1 mm i.d. MolSieve 13×80/100 mesh UltiMetal Plus 41 mm; (4) 3 ft×1/8 in, 2.1 mm i.d. HayeSep Q 80/100 mesh in UltiMetal Plus; (5) 8 ft×1/8 in, 2.1 mm i.d. Molecular Sieve 5A 60/80 mesh in UltiMetal Plus; (6) 2 m×0.32 mm, 5 μm thickness DB-1 (123-1015, cut); and (7) 25 m×0.32 mm, 8 μm thickness HP-AL/S (19091P-S12). The FID channel was configured to analyze the hydrocarbons with the capillary columns from $C_1$ to $C_5$, while $C_6/C_{6+}$ components were backflushed and measured as one peak at the beginning of the analysis. The first channel (reference gas He) was configured to analyze fixed gases (such as $CO_2$, CO, $O_2$, $N_2$, and $H_2S$). This channel was run isothermally, with all micro-packed columns installed inside a valve oven. The second TCD channel (third detector, reference gas $N_2$) analyzed hydrogen through regular packed columns. The analyses from both chromatographs were combined based on the mass of each stream (gas and liquid where present) to provide an overall assay for the reactor.

Chromatographic separation of the gas phase samples in the experimental cracking unit was achieved using an Agilent 8890 GC equipped with a 14-port valve (V1), a 10-port (V2) and two 6-port valves (V3 and V4) in a valve oven, one flame ionization detector (FID), two thermal conductivity detectors (TCD), and the following columns: (1) Column 1: 2'×1/16", 1 mm i.d. HayeSep A 80/100 mesh; (2) Column 2:1.7 m×1/16 in, 1 mm i.d. HayeSep A 80/100 mesh; (3) Column 3:2 m×1/16 in, 1 mm i.d. MolSieve 13×80/100 mesh; (4) Column 4: 3 Ft×1/8 in, 2.1 mm i.d. HayeSep Q 80/100 mesh; (5) Column 5: 8 ft×1/8 in, 2.1 mm i.d. Molecular Sieve 5A 60/80 mesh; (6) Column 6: 2 m×0.32 mm, 5 μm DB-1 (cut from 30 m column); and (7) Column 7: 25 m×0.32 mm, 8 μm HP-AL/S.

The valves and Columns 1, 2 and 3 were installed in a large valve box. This was kept at a constant temperature of 70° C. The permanent gas channel consisted of V2 and V4 and a TCD and used a helium carrier at a flow rate of 12 mL/min. The hydrocarbons channel consisted of V1 and V3 and the FID and used a helium carrier at a rate of 4 mL/min. The hydrogen channel consisted of V1 and the side mounted TCD and used an argon carrier at 22 mL/min. The sample was flushed through a sample loop and the flow was stopped immediately before sample collection began.

Permanent Gases (Hydrogen, Oxygen, Nitrogen, Carbon Monoxide, Carbon Dioxide)

The injection began with V2 on and V4 off. The gas components were distributed through Columns 1 and 2, with the permanent gases eluting to Column 2 and all the other components remaining in Column 1. After 2.5 min, V2 was turned off, allowing $H_2$, $N_2$, and $O_2$ to migrate to Column 3, and at the same time allowing all compounds heavier than $C_3$ to backflush. At 1.6 min, V4 was turned on isolating the gasses in Column 3 and allowing the remaining gases still in Column 2 to be measured by the TCD. At 8.8 minutes, Valve 4 was turned off thereby allowing the light gases trapped in Column 3 to elute.

Hydrocarbons

The injection began with V3 off and V1 on, the hydrocarbons were backflushed onto Column 6, V1 was on during this time. Hydrocarbons lighter than $C_6$ continued to migrate to Column 7. At 0.5 min, V3 turned on, allowing all $C_6$ and heavier compounds to elute together followed by the rest of the hydrocarbons through the FID for quantification.

Hydrogen

The injection began with V1 on and the sample elutes onto Column 4. Hydrogen continued to migrate to Column 5. At 0.45 min, V1 was turned off and every component heavier than hydrogen was backflushed off Column 4. Hydrogen was analyzed by the side TCD.

The initial temperature was 60° C. and held for 1 min, then ramped to 80° C. at a rate of 20° C./min, finally ramped to 190° C. at a rate of 30° C./min and held for 7 min. The inlet temperature was 250° C. and the split ratio was 80:1.

The liquid phase samples, including Pyoil examples described below were analyzed on an Agilent 7890A equipped with a split injector and a flame ionization detector. The stationary phase was a Restek RTX-1 column 30 m×320 µm and had a film thickness of 0.5 µm. The carrier gas was hydrogen at a flow of 2 mL/min. The injection volume was 1 µL, the injector temperate was 250° C., and the split ratio was 50:1. Retention times were confirmed by mass spectrometry where possible.

Example 1—Pyrolysis of HDPE in the Presence of H-ZSM-5

A sample of H-ZSM-5 zeolite with an Si:Al ratio of 50:1 (Valfor CP™) was obtained from PQ Corp. 200 g of HDPE pellets obtained from Westlake Chemical Company were loaded into the pyrolyzation flask of the pyrolyzation unit. 20 g (10% by weight) of zeolite was added. The entire apparatus was purged with $N_2$ and heated to 175° C. and held for 1 h to allow the polymer to melt. The reactor temperature setting was increased to 400° C., but the mixture reached reflux at 250° C. After only 1 h, pyoil ceased to evolve and 53.8 g of py oil was collected. The flask contained only 20 g of spent catalyst, indicating a conversion of 100%. The resultant pyoil was composed of lighter hydrocarbons mostly containing a carbon number from 3 to 11. TABLE 1 provides additional details regarding the formulations of the resulting pyoil and pygas.

Example 2—Pyrolysis of PP in the Presence of H-ZSM-5

The process of Example 1 was repeated except with 195 g of shredded polypropylene obtained from Aldrich Chemical Co as a 0.125" sheet. 19 g of HZSM-5 from PQ Corp. was added and used as the catalyst. The PP was melted at 220° C. and pyrolysis occurred at 275° C. After 1.5 h, 78.3 g of pyoil was obtained and only spent catalyst remained in the flask, thereby indicating 100% conversion. TABLE 1 provides additional details regarding the formulations of the resulting pyoil and pygas.

Example 3—Pyrolysis of HDPE in the Presence of H-ZSM-5 (2 wt %)

The process of Example 1 was repeated except with 100 g of HDPE and 2 g of HZSM-5. Pyrolysis was complete in about 1 h and conversion was 90%. TABLE 1 provides additional details regarding the formulations of the resulting pyoil and pygas.

Example 4—Pyrolysis of Mixed Post-Consumer Plastics with H-ZSM-5

The process of Example 1 was repeated except with a mixture of polyolefins obtained from post-consumer sources and 2 g of HZSM-5. The mixture was comprised of 69 percent high density polyethylene, 16 percent low density polyethylene, and 16 percent polypropylene. 2.0 g of H-ZSM-5 was then added. The reaction mixture was heated to 200° C. and held for 1 h to melt the plastics. The heating was increased to 250° C. and held for 2 h. 67.5 g of pyoil was then collected, which had a resultant density of 0.7011 g/mL. After pyrolysis was complete, the reaction flask held 6.6 g char, equivalent to 95% conversion. TABLE 1 provides additional details regarding the formulations of the resulting pyoil and pygas.

Example 5—Pyrolysis of HDPE in the Presence of NaY Zeolite

A sample of NaY Zeolite was obtained from PQ Corp. 100 g of HDPE pellets and 2 g of NaY Zeolite were subjected to pyrolysis in the $N_2$ purged unit described above. The pellets were brought to 200° C. and held for 1 h to melt. The temperature of the pyrolysis was increased until reflux was obtained at 380° C. Temperature was maintained for 2 h and the reactor cooled. 51.4 g of pyoil was collected in the collection flask. 29.4 g of wax and spent catalyst remained in the flask, indicating an overall conversion of 73%. TABLE 1 provides additional details regarding the formulations of the resulting pyoil and pygas.

Example 6—Pyrolysis of PP in the Presence of NaY Zeolite 200 g of Eastoflex P1001 amorphous polypropylene was obtained from Eastman Chemical Company and loaded into the pyrolysis apparatus described above. 7.5 g (3.6 weight %) of NaY Zeolite was then added. The apparatus was sealed and purged with $N_2$. The pellets were melted at 180° C. over the course of 1 h. The temperature was increased to 265° C., at which point pyoil began to collect in the receiver flask. The pyrolysis was maintained for 2.5 h and the residue cooled. TABLE 1 provides additional details regarding the formulations of the resulting pyoil and pygas.

Example 7—Pyrolysis of HDPE in the Presence of Amberlyst 15

The process of Example 1 was repeated except with 10 g of Amberlyst 15, an acidic polystyrene based ion-exchange resin produced by Dow Chemical Company. Pyrolysis occurred when the melted plastic reached 380° C. Pyoil was collected for 3 hours. After the reaction was completed, 83.1 g of pyoil was collected. 68.7 g of char and spent catalyst remained corresponding to 70% conversion. TABLE 1 provides additional details regarding the formulations of the resulting pyoil and pygas.

TABLE 1

| | Example | | | | | | |
|---|---|---|---|---|---|---|---|
| | 1 | 2 | 3 | 4 | 5 | 6 | 7 |
| Plastic | HDPE | PP | HDPE | HDPE LDPE PP | HDPE | PP | HDPE |
| Pyoil Yield | 26% | 40% | 54% | ~68% | ~51% | ~57% | ~42% |
| Pygas Yield | 74% | 60% | 36% | ~28% | ~21% | ~24% | ~29% |
| Pyrolysis Residue Yield | 0% | 0% | 10% | ~4.6% | ~27.3% | ~18.3% | ~29.3% |
| Pyoil Alkanes (wt %) | 15% | 14% | 48% | 43% | 53% | 44% | 61% |
| Pyoil Olefins (wt %) | 21% | 31% | 44% | 44% | 31% | 33% | 31% |
| Pyoil Aromatics (wt %) | 25% | 42% | 1.2% | 12% | 5% | 13% | 5.7% |
| Pygas $C_2$ (mol %) | 9.5% | 9.6% | 5.4% | 7.2% | 18% | 1% | 13% |
| Pygas $C_3$ (mol %) | 39% | 63% | 70% | 55% | 41% | 24% | 34% |
| Pygas $C_4$ (mol %) | N/A | 14% | 15.9% | 22.2% | 23.2% | 48.3% | 23.1% |
| Pygas $C_5$ (mol %) | N/A | 1.89% | 1.55% | 4.71% | 4.36% | 16.83% | 10.52% |
| Pygas $H_2$ (mol %) | 7.3% | 8.6% | 1.4% | 4.7% | 4.1% | 0.0% | 4.0% |
| Pygas $CH_4$ (mol %) | 2.1% | 1.9% | 0.3% | 1.0% | 6.2% | 0.0% | 8.5% |
| Pygas Ethane (mol %) | 2.8% | 2.4% | 0.6% | 1.7% | 12.4% | 0.9% | 9.4% |
| Pygas Ethylene (mol %) | 6.8% | 7.2% | 4.8% | 5.5% | 5.2% | 0.0% | 4.0% |
| Pygas Propane (mol %) | 21.6% | 45.4% | 23.9% | 38.9% | 14.7% | 1.9% | 10.8% |
| Pygas Propylene (mol %) | 17.7% | 17.5% | 46.4% | 17.2% | 25.9% | 21.5% | 22.9% |
| Pygas i-Butane (mol %) | 15.5% | 7.7% | 3.2% | 11.0% | 6.2% | 0.9% | 5.4% |
| Pygas n-Butane (mol %) | 3.2% | 0.0% | 0.0% | 0.0% | 0.0% | 0.0% | 0.0% |
| Pygas t-2-Butene(mol %) | 2.5% | 1.2% | 10.0% | 2.0% | 7.4% | 4.7% | 4.9% |
| Pygas 1-Butene(mol %) | 9.0% | 4.1% | 2.5% | 7.0% | 6.0% | 35.5% | 10.8% |
| Pygas i-Butylene (mol %) | 1.5% | 1.0% | 0.0% | 2.0% | 3.1% | 5.6% | 1.3% |
| Pygas c-2-Butene (mol %) | 0.5% | 0.0% | 0.1% | 0.0% | 0.0% | 0.0% | 0.0% |
| Pygas i-Pentane (mol %) | 2.5% | 0.9% | 0.4% | 2.0% | 0.9% | 1.9% | 8.5% |
| Pygas n-Pentane (mol %) | 0.2% | 0.0% | 0.0% | 0.0% | 0.5% | 0.0% | 0.0% |
| Pygas 1,3-Butadiene (mol %) | 0.3% | 0.1% | 0.2% | 0.2% | 0.3% | 0.9% | 0.4% |
| Pygas Methyl Acetylene (mol %) | 1.9% | 0.3% | 2.9% | 1.2% | 2.2% | 3.7% | 2.2% |
| Pygas Cyclopentadiene (mol %) | 0.1% | 0.1% | 0.2% | 0.0% | 0.2% | 0.9% | 0.0% |
| Pygas t-2-Pentene (mol %) | 1.9% | 0.6% | 0.7% | 1.5% | 1.4% | 9.3% | 0.9% |
| Pygas 2-Methyl-2-Butene (mol %) | 0.8% | 0.3% | 0.3% | 0.7% | 0.9% | 4.7% | 0.4% |
| Pygas 1-Penene (mol %) | 0.2% | 0.1% | 0.0% | 0.2% | 0.7% | 0.9% | 0.4% |
| Pygas $C_{6+}$ (mol %) | 4.0% | 0.8% | 2.1% | 3.0% | 1.7% | 6.5% | 4.9% |
| Pygas $CO_2$ (mol %) | 0.0% | 0.0% | 0.0% | 0.0% | 0.0% | 0.0% | 0.0% |

As shown above, the use of an HZSM-5 type zeolite significantly reduced the temperature at which reflux was reached in the pyrolysis vessel. As can be seen in Example 1, the carbon distribution in pyoil from HDPE, catalyzed by 10 weight % of the zeolite, is comprised of significantly lower mass materials. In other words, it appears that more pygas is generated in the presence of HZSM-5. Interestingly, the result pyoil, both from HDPE and PP, as shown in Examples 1 and 2, contain higher concentrations of aromatics. The use of HZSM-5 in the pyrolysis of mixed postconsumer polyolefins resulted in higher conversion in Example 4, (but less pygas as compared to straight HDPE or PP).

NaY zeolite, a synthetic zeolite with a Faujasite type crystal structure containing Na impurities, was also investigated as a catalyst. In the case of HDPE, pyrolysis does not occur until 380° C. and takes 2 h to reach a conversion of 73%. Selectivity to pyoil vs pygas at a 2% loading remains around 50%. NaY fails as a catalyst at higher loading as well (10% vs 2%) resulting in "bumping" in the pyrolysis unit and plugging of the lines with partially melted plastic and wax. This is not unexpected—the "H" form of the catalyst would be significantly more acidic and a better catalyst especially for polyethylenes. Lower temperature pyrolysis is achieved with 100% polypropylene at a loading of 3.5%. 57% of the original material is converted to pyoil with a very low carbon distribution (Example 6).

Amberlyst 15, a highly acidic polystyrene based ion-exchange resin, did not demonstrate catalytic activity towards pyrolysis of HDPE.

Prophetic Examples 2A-7A

Additionally, computer simulations were performed using the pygas and pyrolysis residue compositions from Examples 2-7 in order to predict syngas formulations that could be produced from these compositions after being fed to a partial oxidation (PDX) gasifier.

For the pygas, it was assumed that only the pygas and oxygen were fed into a PDX reactor without any other feeds, such as natural gas or other hydrocarbons. The predictive model simulated the PDX reactor being operated at a temperature of 1,200° C. and a pressure of 400 psig, along with a $H_2/CO$ ratio of 0.97.

The syngas formulations predicted from the pygas formulations via the predictive modeling are provided below in TABLE 2. It should be noted that the following syngas properties are based on molar fractions of the syngas (dry basis) at the PDX reactor exit. In addition, TABLE 2 also provides the estimated SCF of syngas produced per pound of plastic present in the initial pyrolysis feed.

TABLE 2

| Sample | $H_2$ | CO | $CO_2$ | Syngas (SCF/lb - Plastic) |
|---|---|---|---|---|
| Example 2 | 0.463 | 0.478 | 0.059 | 35.0 |
| Example 3 | 0.453 | 0.467 | 0.081 | 19.9 |
| Example 4 | 0.460 | 0.474 | 0.066 | 15.9 |
| Example 5 | 0.457 | 0.472 | 0.071 | 12.2 |
| Example 6 | 0.444 | 0.458 | 0.098 | 13.2 |
| Example 7 | 0.457 | 0.471 | 0.072 | 16.4 |

In addition, syngas formulations simulated using the pyrolysis residues from Examples 3-7 were further modeled as being subjected to partial oxidation in a coal slurry fed gasifier. The simulation was performed assuming that only the pyrolysis residue was fed into the coal slurry fed gasifier (69% solids in water) and with operating conditions including a temperature greater than 1300° C. and a nominal pressure of 1000 psig. It was also assumed that all the pyrolysis residue has a similar composition and, based on previous measurements, has a 1.1:1 C:H elemental ratio and exhibits a BTU value of 8,220 BTU/lb. Furthermore, it was assumed that there was is appreciable oxygen left in the residue.

The Dulong equation used in the simulation estimates the amount of inert materials and the resulting higher heating value (HHV) and lower heating value (LHV) of the pyrolysis residue. The simulation is performed under the assumption that each of the pyrolysis residues used in Examples 3-7 includes 49.3 weight percent of carbon, 3.7 weight percent of hydrogen, and 47 weight percent of inert materials and exhibits an HHV of 8,568 BTU/lb and an LHV of 8,218 BTU/lb.

The syngas formulations predicted by the simulation using the pyrolysis residues are provided below in TABLE 3. It should be noted that the following syngas properties are based on molar fractions of the syngas (dry basis) at the gasifier exit. In addition, TABLE 3 also provides the estimated standard cubic feet (SCF) of syngas produced per pound of plastic present in the initial pyrolysis feed.

TABLE 3

| Sample | $H_2$ | CO | $CO_2$ | Syngas (SCF/lb - Plastic) |
|---|---|---|---|---|
| Example 3 | 0.360 | 0.460 | 0.180 | 1.9 |
| Example 4 | 0.360 | 0.460 | 0.180 | 0.8 |
| Example 5 | 0.360 | 0.460 | 0.180 | 4.9 |
| Example 6 | 0.360 | 0.460 | 0.180 | 3.3 |
| Example 7 | 0.360 | 0.460 | 0.180 | 5.3 |

Example 8 Pyrolysis and Separation of PVC Containing Mixed Plastics

Pyrolysis Unit: the pyrolysis unit was comprised of a 1 L quartz round bottom flask containing three necks. One neck was fitted with an open-ended quartz dip tube connected by stainless steel adapter to a gas inlet. A K-type thermocouple was inserted through the dip tube, subsurface into the reaction mixture. In addition to monitoring reaction temperature, the dip tube was used to introduce gas feeds (e.g., nitrogen, hydrogen, or steam) subsurface into the pyrolysis mixture and to ensure adequate mixing during the pyrolysis experiments. Another neck was fitted with a glass distillation head. The distillation head was topped with a thermowell and J-type thermocouple. The outlet of the distillation head was fitted to a vertically hung condenser containing a 50/50 mixture of glycol and water as a cooling medium and was maintained at 60° C. The outlet of the condenser was fitted to a glass gas separation tube, with the gas outlet connected to two dry ice traps in series. Non-condensable vapors exiting the dry ice traps were collected in TEDLAR® gas sample bags for analysis. Liquids condensed in the vertically hung condenser were collected in a graduated product tank.

Analytical: analysis of reaction feed components and products was done by gas chromatography as described above. All percentages were by weight unless specified otherwise.

Example 8A: Pyrolysis of Post-Consumer Mixed Polyolefins Under Nitrogen

A mixture of post-consumer polyolefins was subjected to thermal pyrolysis using the apparatus described above. The pyrolysis flask was charged with a 52 g mixture comprised of 77% polypropylene and 23% LDPE and then purged with $N_2$. The mixture was heated to 200° C. and held for 1 h to allow the polymers to melt and then the temperature was increased to 400° C. After 3 h of pyrolysis at 400° C., 18.5 g of pyoil was collected and 20.6 g of unconverted residue remained in the unit. The pyoil was comprised of hydrocarbons with chain lengths between $C_4$ and $C_{22}$. The mixture contained 71% alkanes, 15% olefins, and 5% aromatics. 9% of the mixture was unidentified. Table 23 contains the reaction data for the examples. TABLE 4 provides additional details regarding the formulations of the resulting pyoil and pygas.

Example 8B: Pyrolysis of Post-Consumer Mixed Plastics Under Nitrogen

The reaction of Example 8-A was repeated with 104 g of post-consumer plastic comprised of 52% HDPE, 30% PP, and 18% LDPE. After 3 h at 400° C., 36.6 g of pyoil was collected and 57 g of residue remained. TABLE 4 provides additional details regarding the formulations of the resulting pyoil and pygas.

Comparative Example 8C: Pyrolysis of Post-Consumer Mixed Plastics with PVC

The reaction of Example 8-A was repeated with a 96.9 g mixture of post-consumer plastics containing 58% PP, 34% LDPE, and 8% PVC. The mixture was melted at 200° C. and held for 1 h. Pyrolysis was conducted at 400° C. for 2 h. At the end of the pyrolysis, 55.9 g of pyoil was collected and 26.8 g of residue remained in the flask. Analysis for chlorides reveled the mixture contained 4500 ppm Cl. TABLE 4 provides additional details regarding the formulations of the resulting pyoil and pygas.

Example 8D: Pyrolysis of PVC-Containing Mixed Plastics with KOH Scrubber

A scrubber containing a 20% aqueous solution of KOH was connected to the vent line between the warm condenser and the pyrolysis oil collection vessel. The outlet of the scrubber was connected to two dry ice traps in series. A plastic mixture composed of 58% PP, 34% LDPE, and 8% PVC was added to the quartz pyrolysis vessel and heated to 250° C. The plastic melted and began to evolve gases containing chlorides. The reaction mixture was held at 250° C. for 2 h and then the scrubber was removed from the unit and the dry ice traps reconnected to the vapor line. The reaction mixture was increased to 400° C. and held for 2 h.

At the end of the pyrolysis, 46.6 g of pyoil was collected (51.3% conversion) and 13.8 g of char remained in the flask (85% total conversion). The resultant pyoil had a chloride content of 520 ppm. TABLE 4 provides additional details regarding the formulations of the resulting pyoil and pygas.

TABLE 4

| | Example | | | |
|---|---|---|---|---|
| | 8A | 8B | 8C | 8D |
| Plastic | LDPE/PP | HDPE/ LDPE/PP | LDPE/ PP/PVC | LDPE/ PP/PVC |
| Pyoil Yield | ~36% | ~35% | ~58% | ~51% |
| Pygas Yield | ~25% | ~10% | ~15% | ~33% |
| Pyrolysis Residue Yield | ~39.6% | ~54.8% | ~27.7% | ~15.4% |
| Pyoil Alkanes (wt %) | 71% | 50% | 51% | 55% |
| Pyoil Olefins (wt %) | 15.1% | 27.7% | 15.5% | 34% |
| Pyoil Aromatics (wt %) | 4.8% | 4.9% | 4.0% | 4.4% |
| Pygas $C_2$ (mol %) | 12% | 24% | 18% | 14% |
| Pygas $C_3$ (mol %) | 42% | 46% | 34% | 28% |
| Pygas $C_4$ (mol %) | 7.9% | 19.4% | 22.4% | 19.1% |
| Pygas $C_5$ (mol %) | 30.3% | 4.6% | 9.7% | 7.6% |
| Pygas $H_2$ (mol %) | 0.0% | 4.5% | 2.6% | 3.0% |
| Pygas $CH_4$ (mol %) | 5.7% | 10.5% | 10.1% | 13.1% |
| Pygas Ethane (mol %) | 11.3% | 14.9% | 13.9% | 10.1% |
| Pygas Ethylene (mol %) | 0.0% | 5.6% | 4.5% | 3.9% |
| Pygas Propane (mol %) | 3.8% | 15.8% | 13.7% | 11.3% |
| Pygas Propylene (mol %) | 35.8% | 23.2% | 19.9% | 15.2% |
| Pygas i-Butane (mol %) | 0.0% | 5.6% | 0.4% | 5.7% |
| Pygas n-Butane (mol %) | 0.0% | 0.0% | 5.6% | 0.0% |
| Pygas t-2-Butene(mol %) | 1.9% | 5.8% | 1.1% | 5.4% |
| Pygas 1-Butene(mol %) | 7.5% | 7.3% | 5.1% | 15.2% |
| Pygas i-Butylene (mol %) | 0.0% | 0.7% | 8.8% | 0.6% |
| Pygas c-2-Butene (mol %) | 0.0% | 0.0% | 0.6% | 0.0% |
| Pygas i-Pentane (mol %) | 32.1% | 3.4% | 0.2% | 9.0% |
| Pygas n-Pentane (mol %) | 0.0% | 0.8% | 6.4% | 0.9% |
| Pygas 1,3-Butadiene (mol %) | 0.0% | 0.0% | 0.9% | 0.0% |
| Pygas Methyl Acetylene (mol %) | 1.9% | 0.4% | 0.2% | 1.2% |
| Pygas Cyclopentadiene (mol %) | 0.0% | 0.0% | 0.6% | 0.6% |
| Pygas t-2-Pentene (mol %) | 0.0% | 0.1% | 0.2% | 0.3% |
| Pygas 2-Methyl-2-Butene (mol %) | 0.0% | 0.1% | 1.5% | 0.3% |
| Pygas 1-Penene (mol %) | 0.0% | 0.1% | 0.4% | 0.3% |
| Pygas $C_{6+}$ (mol %) | 0.0% | 1.2% | 3.2% | 3.9% |
| Pygas $CO_2$ (mol %) | 0.0% | 0.0% | 0.0% | 0.0% |

A review of TABLE 4 reveals that the inclusion of PVC in the post-consumer plastics mix resulted in a higher conversion to pyoil and a higher overall conversion. It is believed the chloride group in the PVC chain may result in the polymer having a more kinetically favored degradation mechanism. The inclusion of PVC in the pyrolysis mixture also increased the amount of olefin generated with minimal effect on the aromatic content. With no pre-pyrolysis treatment, the resultant pyoil contained 4500 ppm of chlorides. Preheating at 250° C., in combination with a caustic scrubber, resulted in an order of magnitude reduction in the chloride content of the resultant pyoil. A higher conversion of plastic to pygas also resulted, reflective of the gas elution during the pretreatment process.

Additionally, a computer simulation was conducted using the pygas and pyrolysis residues from Examples 8A, 8B, and 8D as a feed to a partial oxidation gasifier in order to predict the syngas formulations that could be produced from these compositions.

For the pygas, it was assumed that only the pygas and oxygen were fed into the natural-gas PDX reactor without any other feeds, such as natural gas or other hydrocarbons, The simulation was performed with a PDX reactor temperature greater than 1100° C. and a nominal pressure of 400 psig. The simulation included a $H_2$/CO ratio of 0.97.

The syngas formulations predicted via the simulation from the pygas formulations via the predictive modeling are provided below in TABLE 5. It should be noted that the following syngas properties are based on molar fractions of the syngas (dry basis) at the PDX reactor exit. In addition, TABLE 5 also provides the estimated SCF of syngas produced per pound of plastic present in the initial pyrolysis feed.

TABLE 5

| Sample | $H_2$ | CO | $CO_2$ | Syngas (SCF/lb - Plastic) |
|---|---|---|---|---|
| Example 8A | 0.456 | 0.470 | 0.073 | 14.1 |
| Example 8B | 0.461 | 0.475 | 0.063 | 5.9 |
| Example 8D | 0.460 | 0.474 | 0.066 | 19.2 |

In addition, simulations were performed using the pyrolysis residues from Examples 3-7 as feed to a coal slurry fed gasifier. The predictive modeling assumes that only the pyrolysis residue is fed into the coal slurry fed gasifier (69% solids in water) and that the gasifier is operated at conditions including a temperature greater than 1300° C. and a nominal pressure of 1,000 psig. It was also assumed that all the pyrolysis residue streams have a similar composition and, in particular, that each has a 1.1:1 C:H elemental ratio and exhibited a BTU value of 8,220 BTU/lb.

Furthermore, it is assumed that there is no appreciable oxygen left in the residue. The Dulong equation is used to estimate the amount of inert materials and the resulting HHV and LHV of the pyrolysis residue. Thus, the simulation is performed assuming that each of the pyrolysis residues of Examples 3-7 comprised 49.3 weight percent of carbon, 3.7 weight percent of hydrogen, and 47 weight percent of inert materials and exhibited an HHV of 8,568 BTU/lb and an LHV of 8,218 BTU/lb.

The syngas formulations produced from the pyrolysis residues via the computer simulation are provided below in TABLE 6. It should be noted that the following syngas properties are based on molar fractions of the syngas (dry basis) at the gasifier exit. In addition, TABLE 6 also provides the estimated SCF of syngas produced per pound of plastic present in the initial pyrolysis feed.

TABLE 6

| Sample | $H_2$ | CO | $CO_2$ | Syngas (SCF/lb - Plastic) |
|---|---|---|---|---|
| Example 8A | 0.360 | 0.460 | 0.180 | 7.1 |
| Example 8B | 0.360 | 0.460 | 0.180 | 9.9 |
| Example 8D | 0.360 | 0.460 | 0.180 | 5.0 |

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.

As used herein, the phrase "at least a portion" includes at least a portion and up to and including the entire amount or time period.

As used herein, "downstream" means a target unit operation, vessel, or equipment that:
  a. is in fluid (liquid or gas) communication, or in piping communication, with an outlet stream from the radiant section of a cracker furnace, optionally through one or more intermediate unit operations, vessels, or equipment, or
  b. was in fluid (liquid or gas) communication, or in piping communication, with an outlet stream from the radiant section of a cracker furnace, optionally through one or more intermediate unit operations, vessels, or equipment, provided that the target unit operation, vessel, or equipment remains within the battery limits of the cracker facility (which includes the furnace and all associated downstream separation equipment).

As used herein, the term "predominantly" means more than 50 percent by weight. For example, a predominantly propane stream, composition, feedstock, or product is a stream, composition, feedstock, or product that contains more than 50 weight percent propane.

As used herein, the term "enriched" refers to having a concentration (on a dry weight basis) of a specific component that is greater than the concentration of that component in a reference material or stream.

As used herein, the term "depleted" refers to having a concentration (on a dry weight basis) of a specific component that is less than the concentration of that component in a reference material or stream.

"As used herein, the term "partial oxidation" refers to high temperature conversion of a carbon-containing feed into syngas (carbon monoxide, hydrogen, and carbon dioxide), where the conversion is carried out with an amount of oxygen that is less than the stoichiometric amount of oxygen needed for complete oxidation of carbon to $CO_2$. The feed to PDX gasification can include solids, liquids, and/or gases. A "partial oxidation gasification facility" is a facility that includes all equipment, lines, and controls necessary to carry out PDX gasification of waste plastic and feedstocks derived therefrom."

CLAIMS NOT LIMITED TO DISCLOSED EMBODIMENTS

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A method for making an olefin product, said method comprising: separating a feed stream comprising a recycle content pyrolysis gas (r-pyrolysis gas) in at least one fractionator downstream of a cracker furnace, wherein said r-pyrolysis gas has not been produced in said cracker furnace; wherein said r-pyrolysis gas is produced from mixed plastic waste; and wherein said cracking furnace produces said olefin product, and wherein said r-pyrolysis gas comprises: at least 20 and/or not more than 75 weight percent of ethylene and/or propylene, at least 5 and/or not more than 50 weight percent of ethane and/or propane, at least 5 and/or not more than 60 weight percent of methane, an ethylene to ethane weight ratio or propylene to propane weight ratio of at least 1:1 and/or not more than 3:1, and at least one of the following properties (i) through (ix):
  (i) C4 hydrocarbons in an amount of not more than 20 weight percent; (ii) hydrogen in an amount of not more than 10 weight percent; (iii) C3+ diolefins in an amount of not more than 10 weight percent; (iv) C4+ olefins in an amount of not more than 10 weight percent; (v) C4 paraffins in an amount of not more than 5 weight percent; (vi) halogens in an amount of not more than 1 ppm; (v) carbonyls in an amount of not more than 100 ppm; (vi) carbon dioxide in an amount of not more than 100 ppm; (vii) carbon monoxide in an amount of not more than 2500 ppm; (viii) arsine and/or phosphine in an amount of not more than 15 ppb; and (ix) sulfur-containing compounds in an amount of not more than 100 ppm, wherein each of the above quantities are in amounts by weight, based on the total weight of the composition.

2. The method of claim 1, wherein said feed stream comprises at least a portion of an olefin containing effluent stream withdrawn from said cracker furnace.

3. The method of claim 1, further comprising compressing a pyrolysis stream comprising said r-pyrolysis gas and introducing the compressed stream into said fractionator downstream of said furnace.

4. The method of claim 3, further comprising prior to compressing, combining said pyrolysis gas stream with an olefin-containing effluent stream from said cracker furnace, and compressing the combined stream.

5. The method of claim 1, further comprising, cooling an r-pyrolysis gas stream to form a cooled r-pyrolysis gas stream, wherein said feed stream comprises at least a portion of said cooled r-pyrolysis gas stream.

6. The method of claim 5, further comprising prior to cooling, combining said r-pyrolysis gas stream with an olefin-containing effluent stream from said cracker furnace, and cooling the combined stream.

7. The method of claim 1, wherein said fractionator is selected from the group consisting of a demethanizer, a deethanizer, and a depropanizer.

8. The method of claim 1, wherein said fractionator is selected from the group consisting of an ethane-ethylene splitter and a propane-propylene splitter.

9. The method of claim 1, wherein said feed stream comprises at least 5 and not more than 60 weight percent olefins, based on the total weight of said feed stream.

\* \* \* \* \*